US010844437B2

(12) United States Patent
Parry

(10) Patent No.: US 10,844,437 B2
(45) **Date of Patent: *Nov. 24, 2020**

(54) BIOMARKERS FOR RADIATION TREATMENT

(71) Applicant: Varian Medical Systems, Inc., Palo Alto, CA (US)

(72) Inventor: Renate Parry, Oakland, CA (US)

(73) Assignee: Varian Medical Systems, Inc., Palo Alto, CA (US)

( * ) Notice: Subject to any disclaimer, the term of this patent is extended or adjusted under 35 U.S.C. 154(b) by 226 days.

This patent is subject to a terminal disclaimer.

(21) Appl. No.: 15/913,633

(22) Filed: Mar. 6, 2018

(65) Prior Publication Data

US 2018/0305769 A1 Oct. 25, 2018

Related U.S. Application Data

(63) Continuation of application No. 14/777,209, filed as application No. PCT/US2014/029365 on Mar. 14, 2014, now Pat. No. 9,938,583.

(60) Provisional application No. 61/800,011, filed on Mar. 15, 2013.

(51) Int. Cl.

| | |
|---|---|
| ***G01N 33/573*** | (2006.01) |
| ***C12Q 1/6886*** | (2018.01) |
| ***A61K 31/337*** | (2006.01) |
| ***A61K 31/7115*** | (2006.01) |
| ***A61K 33/24*** | (2019.01) |
| ***A61K 39/395*** | (2006.01) |
| ***A61N 5/10*** | (2006.01) |
| ***G01N 33/574*** | (2006.01) |

(52) U.S. Cl.

CPC .......... *C12Q 1/6886* (2013.01); *A61K 31/337* (2013.01); *A61K 31/7115* (2013.01); *A61K 33/24* (2013.01); *A61K 39/3955* (2013.01); *A61N 5/1064* (2013.01); *G01N 33/57484* (2013.01); *A61N 2005/1098* (2013.01); *C12Q 2600/106* (2013.01); *C12Q 2600/158* (2013.01); *G01N 2333/4703* (2013.01); *G01N 2333/4712* (2013.01); *G01N 2333/70585* (2013.01); *G01N 2333/70596* (2013.01); *G01N 2333/90203* (2013.01); *G01N 2333/96494* (2013.01); *G01N 2400/40* (2013.01)

(58) Field of Classification Search

None

See application file for complete search history.

(56) References Cited

U.S. PATENT DOCUMENTS

| | | | |
|---|---|---|---|
| 9,938,583 | B2 | 4/2018 | Parry |
| 2010/0260667 | A1 | 10/2010 | Georges et al. |
| 2012/0010230 | A1 | 1/2012 | MacDougall et al. |
| 2012/0115165 | A1 | 5/2012 | Franzmann et al. |
| 2016/0024594 | A1 | 1/2016 | Parry |

FOREIGN PATENT DOCUMENTS

| | | |
|---|---|---|
| CN | 1193280 | 9/1998 |
| CN | 101993941 | 3/2011 |
| CN | 105209070 | 12/2015 |
| EP | 2968542 | 1/2016 |
| JP | 2007518709 | 7/2007 |
| JP | 2009513161 | 4/2009 |
| JP | 2016521141 | 7/2016 |
| WO | 2011109440 | 9/2011 |
| WO | 2011109572 | 9/2011 |
| WO | 2011127219 | 10/2011 |
| WO | 2012115885 | 8/2012 |
| WO | 2012131564 | 10/2012 |
| WO | 2014144804 | 9/2014 |

OTHER PUBLICATIONS

Zhou et al (Amer J Path 182:1248-1254, online published Feb. 8, 2013) provided in parent case (Year: 2013).*

Xiao et al (Clin Exp Metastasis 29:1-9, online published Sep. 28, 2011)provided in parent case (Year: 2011).*

Zhang et al (Can Res, 71:7155-67, 2011)provided in parent case (Year: 2011).*

U.S. Appl. No. 14/777,209, Corrected Notice of Allowability dated Mar. 7, 2018, 3 pages.

U.S. Appl. No. 14/777,209, Final Office Action dated Jun. 16, 2017, 13 pages.

U.S. Appl. No. 14/777,209, Non-Final Office Action dated Jan. 19, 2017, 14 pages.

U.S. Appl. No. 14/777,209, Notice of Allowance dated Nov. 27, 2017, 8 pages.

U.S. Appl. No. 14/777,209, Restriction Requirement dated Aug. 12, 2016, 9 pages.

Baumann et al., CD44: A Cancer Stem Cell-Related Biomarker with Predictive Potential for Radiotherapy, Clinical Cancer Research, vol. 16, No. 21, Sep. 22, 2010, pp. 5091-5093.

Choy et al., Preliminary Analysis of a Phase II Study of Paclitaxel, Carboplatin, and Hyperfractionated Radiation Therapy for Locally Advanced Inoperable Non-small Cell Lung Cancer, Semi Oncol, vol. 24, Suppl 12, Aug. 1997, pp. S12-21-S12-26.

Chun et al., Modified Partial Hyperfractionation in Radiotherapy for Bulky Uterine Cervical Cancer: Reduction of Overall Treatment Time, Intern J Radia Onco, vol. 47, Issue 4, Jul. 1, 2000, pp. 973-977.

(Continued)

*Primary Examiner* — Lei Yao

(74) *Attorney, Agent, or Firm* — Kilpatrick Townsend & Stockton LLP

(57) ABSTRACT

The methods described herein allow for the classification of patients into groups for receiving optimized radiation treatment based on patient specific biomarker signature. The biomarker signature includes markers that have been shown to correlate with TGF-B expression and to be associated with tumor aggressiveness, radioresistance and poor prognosis. The markers play a key role in the epithelial-mesenchymal transition. The methods described herein provide the dual benefits of anti-tumor efficacy plus normal tissue protection when combining TGF-B inhibitors with ionizing radiation to treat cancer patients.

17 Claims, 11 Drawing Sheets

Specification includes a Sequence Listing.

(56) References Cited

OTHER PUBLICATIONS

*Chinese Application No. 201480027690.8, Office Action dated Mar. 2, 2017, 12 pages (8 pages for the original document and 4 pages for the English translation).
Cui et al., Effects of Carbon Ion Beam on Putative Colon Cancer Stem Cells and Its Comparison with X-Rays, Cancer Research, vol. 71, No. 10, May 15, 2011, pp. 3676-3687.
Ducray et al., An ANOCEF Genomic and Transcriptomic Microarray Study of the Response to Radiotherapy or to Alkylating First-line Chemotherapy in Glioblastoma Patients, Molecular Cancer, Biomed Central, London, vol. 9, No. 1, Sep. 7, 2010, 16 pages.
European Application No. 14762902.6, Extended European Search Report dated Jul. 27, 2016, 11 pages.
*European Application No. 14762902.6, Office Action dated Oct. 2, 2017, 8 pages.
Goos et al., Abstract 5217: MMP9 Is a Prognostic Biomarker for Metastatic Colorectal Cancer, Cancer Research, Proceedings: AACR 102nd Annual Meeting, Apr. 15, 2011, 2 pages.
Japanese Application No. 2016-503075, Office Action dated Feb. 20, 2018, 10 pages.
Komaki et al., Vimentin (EMT Marker Protein) Score Predicts Resistance to Erlotinib and Radiation Therapy for Patients With Stage III Non-small Cell Lung Cancer on a Prospective Phase II Trial, International Journal of Radiation: Oncology Biology Physics, vol. 84, No. 3, 2012, pp. S24-S25.
Minoo et al., Characterization of Rectal, Proximal and Distal Colon Cancers Based on Clinicopathological, Molecular and Protein Profiles, International Journal of Oncology, vol. 37, No. 3, Sep. 1, 2010, pp. 707-718.
Oka et al., Adenocarcinoma of the Cervix Treated With Radiation Alone: Prognostic Significance of S-100 Protein and Vimentin Immunostaining, Obstetrics and Gynecology, vol. 79, No. 3, Mar. 1992, pp. 347-350.
*International Application No. PCT/US2014/029365, International Preliminary Report on Patentability dated Sep. 24, 2015, 6 pages.
International Application No. PCT/US2014/029365, International Search Report and Written Opinion dated Jul. 8, 2014, 11 pages.
Xiao et al., CD44 Is a Biomarker Associated With Human Prostate Cancer Radiation Sensitivity, Clinical & Experimental Metastasis, vol. 29, Issue 1, Jan. 2012, pp. 1-9.
Yaromina et al., Individualization of Cancer Treatment from Radiotherapy Perspective, Molecular Oncology, vol. 6, No. 2, Apr. 2012, pp. 211-221.
Zhang et al., Blockade of TGF-β Signaling by the TGFβR-I Kinase Inhibitor LY2109761 Enhances Radiation Response and Prolongs Survival in Glioblastoma, Can Res, vol. 71, No. 23, 2011, pp. 7155-7167.
Zhou et al., Radiation-Induced Lung Injury is Mitigated by Blockade of Gastrin-Releasing Peptide, Am J Pathol., vol. 182, No. 4, Apr. 2013, pp. 1248-1254.
Japan Application No. JP2016-503075, “Office Action”, dated Oct. 25, 2018, 3 pages.
Chinese Application No. 201480027690.8, Office Action dated Aug. 13, 2018, 11 pages (7 pages of the original document and 4 pages of the English translation).
Yu et al., Expressions of CD68 and c-Jun Proteins in Non-Small Cell Lung Cancer Tissue, Journal of Zhengzhou University (Medical Sciences), vol. 46, No. 6., Nov. 30, 2011, 4 pages.
Japan Application No. JP2016-503075, “Office Action”, dated Mar. 23, 2020, 5 pages.
Japan Application No. JP2019-031738, “Office Action”, dated Apr. 6, 2020, 2 pages.

* cited by examiner

BIOMARKERS FOR RADIATION TREATMENT

CROSS-REFERENCE TO RELATED PATENT APPLICATIONS

The present application is a continuation of, and claims the benefit and priority to U.S. application Ser. No. 14/777,209, filed Sep. 15, 2015, now U.S. Pat. No. 9,938,583, entitled "BIOMARKERS FOR RADIATION TREATMENT," which claims the benefit and priority of International Application No. PCT/US2014/029365, filed Mar. 14, 2014, entitled "BIOMARKERS FOR RADIATION TREATMENT," which claims benefit and priority under 35 U.S.C. § 119(e) to U.S. Provisional Application No. 61/800,011, filed Mar. 15, 2013, the entire contents of which are herein incorporated by reference for all purposes.

REFERENCE TO A "SEQUENCE LISTING" SUBMITTED AS ASCII TEXT FILE

The Sequence Listing written in file 088389-002920US-079276 SequenceListing.txt created on May 16, 2018, 126,732 bytes, machine format IBM-PC, MS-Windows operating system, in accordance with 37 C.F.R. §§ 1.821 to 1.825, is hereby incorporated by reference in its entirety for all purposes.

BACKGROUND OF THE INVENTION

No validated protein signature is available that has been proved to be sufficiently useful in the clinic to stratify patients into groups that may be treated differently with radiotherapy. Many factors determine the biology of tumors and as such impact prognosis and survival outcome of cancer patients. TGF-β is a pleiotropic cytokine that is important in normal tissue homeostasis, regulates inflammation and immune responses, and controls proliferation and differentiation. TGF-β appears to be key in promoting epithelial-mesenchymal-transition (EMT), a process that leads to increased motility and invasion. Due to these oncogenic properties of TGF-β, several TGF-β signalling inhibitors are in preclinical and clinical trials to treat cancer. Radiotherapy is a corner stone of cancer therapy. There is substantial evidence that TGF-β plays a key role in the response to ionizing radiation. TGF-β is activated in irradiated tissues and plays a pivotal role in development of radiation induced fibrosis.

BRIEF SUMMARY OF THE INVENTION

The disclosure provides biomarkers that are useful for diagnosing and treating tumors or cancer in a subject. The disclosure further provides methods of treating tumors in a subject having modified (i.e., increased or decreased) levels of one or more biomarkers described herein. In some embodiments, methods for treating tumors where the level of one or more biomarkers is increased and the level of another biomarker is decreased are described. The disclosure also provides methods of diagnosing or identifying subjects in need of treatment based on the expression levels of the biomarkers described herein. In some embodiments, the treatment comprises administering ionizing radiation to the subject.

In one embodiment, the treatment comprises administering an increased dose of ionizing radiation to the subject if the level of one or more biomarkers described herein is modified in the tumor environment, where the dose of ionizing radiation is increased as compared to the standard of care for a subject that does not have modified levels of the biomarker(s) in the tumor environment. Alternatively, the treatment can comprise administering the same or a similar dose of ionizing radiation as the standard of care in combination with a pharmaceutically effective amount of an anti-cancer agent. For example, in some embodiments, if the subject is already undergoing treatment with ionizing radiation, the amount of ionizing radiation administered to the tumor or subject is maintained at the current treatment dose and/or interval, and an anti-cancer agent is administered to the subject if the level of one or more biomarkers described herein is modified in the tumor environment.

In one aspect, the method comprises modifying the standard radiation treatment protocol if the level of a biomarker described herein is modified in the tumor environment. In some embodiments, the standard radiation treatment protocol is modified by increasing the dose of ionizing radiation administered to the tumor. In some embodiments, the standard radiation treatment protocol is modified by hypofractionation or hyperfractionation of the dose of ionizing radiation. In some embodiments, the standard radiation treatment protocol is modified by further administering an anti-cancer agent or TGF-beta inhibitor to the subject.

In some embodiments, the method comprises modifying the standard radiation treatment protocol if the level of a biomarker selected from the group consisting of CD44, MMP9, ALDH1A1, Vimentin, hyaluronan, beta-catenin, MFG-E8 and CD68 is modified in the tumor environment. The level of a biomarker is modified if the level is increased or decreased compared to the level of the biomarker in a normal (i.e., non-diseased) or control tissue.

In some embodiments, the method comprises modifying the standard radiation treatment protocol if the level of CD68 is increased in the tumor environment. In some embodiments, the method comprises modifying the standard radiation treatment protocol if the level of CD44 is increased in the tumor environment. In some embodiments, the method comprises modifying the standard radiation treatment protocol if the level of CD44 is increased and the level of MFG-E8 is decreased in the tumor environment.

In some embodiments, the standard radiation treatment protocol is modified by increasing the dose of ionizing radiation administered to the tumor. In some embodiments, the standard radiation treatment protocol is modified by hypofractionation. In some embodiments, standard radiation treatment protocol is modified by hyperfractionation.

In some embodiments, the treatment further comprises administering an anti-cancer agent to the subject. In some embodiments, the anti-cancer agent is a chemotherapeutic agent, radiosensitizer, or immune modulator. In some embodiments, the treatment further comprises administering a TGF-beta inhibitor to the subject. In some embodiments, the TGF-beta inhibitor is an antibody or a small molecule that neutralizes or inhibits TGF-beta function. In some embodiments, the TGF-beta inhibitor inhibits the production of TGF-beta.

In one embodiment, the method comprises:

(i) administering an increased dose of radiation to the subject, where the dose of radiation is increased compared to the dose administered to a subject that does not have elevated levels of CD68 in the tumor environment; or (ii) administering a dose of radiation to the subject that is similar to the dose administered to a subject that does not have elevated levels of CD68 in the tumor environment in combination with a pharmaceutically effective amount of an anti-cancer agent, thereby treating the tumor in the subject.

In one embodiment, the method comprises:

(i) administering an increased dose of radiation to the subject, where the dose of radiation is increased compared to the dose administered to a subject that does not have elevated levels of CD44 in the tumor environment; or (ii) administering a dose of radiation to the subject that is similar to the dose administered to a subject that does not have elevated levels of CD44 in the tumor environment in combination with a pharmaceutically effective amount of an anti-cancer agent, thereby treating the tumor in the subject.

In some embodiments, the disclosure provides a method for treating a tumor in a subject having increased levels of one or more biomarkers and decreased levels of another biomarker described herein. For example, in one embodiment, a method for treating a tumor in a subject having increased levels of CD44 and decreased levels of MFG-E8 in the tumor environment is described, the method comprising:

(i) administering an increased dose of radiation to the subject, where the dose of radiation is increased compared to the dose administered to a subject that does not have elevated levels of CD44 and decreased levels of MFG-E8 in the tumor environment; or (ii) administering a dose of radiation to the subject that is similar to the dose administered to a subject that does not have elevated levels of CD44 and decreased levels of MFG-E8 in the tumor environment in combination with a pharmaceutically effective amount of an anti-cancer agent, thereby treating the tumor in the subject.

In some embodiments, the increased dose of radiation is administered in a hyperfractionated mode. In some embodiments, the increased dose of radiation is administered in a hypofractionated mode.

In some embodiments, the anti-cancer agent is a chemotherapeutic agent, radiosensitizer, or immune modulator. In some embodiments, the anti-cancer agent is an antibody that neutralizes or inhibits TGF-beta function. In one embodiment, the anti-cancer agent is a small molecule that neutralizes or inhibits TGF-beta function. In some embodiments, the anti-cancer agent inhibits the production of TGF-beta.

In another aspect, the disclosure provides a method for treating a tumor in a subject in need thereof, the method comprising:

(a) determining an expression level of two or more biomarkers in a tumor sample from the subject, wherein the two or more biomarkers are selected from the group consisting of CD44, MMP9, ALDH1A1, Vimentin, hyaluronan, beta-catenin, MFG-E8, and CD68;

(b) comparing the expression level of the two or more biomarkers to an expression level in a normal tissue sample; and treating the tumor if the expression level of the two or more biomarkers is modified compared to the expression level in the normal tissue sample.

In another aspect, a method of identifying a subject as a candidate for treatment with ionizing radiation is disclosed, the method comprising:

(a) determining an expression level of two or more biomarkers in a tumor sample from the subject, wherein the one or more biomarkers are selected from the group consisting of CD44, MMP9, ALDH1A1, Vimentin, hyaluronan, beta-catenin, MFG-E8, and CD68; and (b) comparing the expression level of the two or more biomarkers to an expression level in a normal tissue sample;

wherein an expression level of the two or more biomarkers in the tumor sample that is modified compared to the expression level in the normal tissue sample identifies the subject as a candidate for treatment with ionizing radiation.

In another aspect, a method of treating a subject having a tumor is disclosed, the method comprising:

administering ionizing radiation to a subject that has been selected as having an expression level of two or more biomarkers in a tumor sample that is modified relative to an expression level in a normal tissue sample;

wherein the two or more biomarkers are selected from the group consisting of CD44, MMP9, ALDH1A1, Vimentin, hyaluronan, beta-catenin, MFG-E8, and CD68;

thereby treating the tumor in the subject.

In another aspect, a method for selecting a treatment for a subject having a tumor is disclosed, the method comprising:

(a) determining an expression level of two or more biomarkers in a tumor sample from the subject, wherein the two or more biomarkers are selected from the group consisting of CD44, MMP9, ALDH1A1, Vimentin, hyaluronan, beta-catenin, MFG-E8, and CD68;

(b) comparing the expression level of the two or more biomarkers to an expression level in a normal tissue sample; and selecting a treatment if the expression level of the two or more biomarkers is modified compared to the expression level in the normal tissue sample.

In the methods, the expression level of the two or more biomarkers is modified if the expression level of at least one of the biomarkers is increased, or if the expression level of at least one of the biomarkers is decreased, or if the expression level of at least one of the biomarkers is increased and the expression level of at least one of the biomarkers is decreased compared to the expression level in a normal tissue sample.

In the above aspects, the treatment comprises administering ionizing radiation to the tumor. In some embodiments, the treatment further comprises contacting the tumor with a radiosensitizer. In one embodiment, the treatment further comprises administering a compound that inhibits TGF-beta signaling to the subject.

In some embodiments, the tumor sample is a biopsy comprising tumor cells. In one embodiment, the tumor is a lung cancer tumor and the tumor sample comprises lung cancer cells. In some embodiments, the biomarker is a gene, an RNA, an extracellular matrix component, or a protein. In some embodiments, the expression level of the biomarker is determined by detecting the expression of an RNA and/or a protein. For example, the expression level can be detected by immunohistochemistry, ELISA, Western analysis, HPLC, proteomics, PCR, RT-PCR, Northern analysis, and/or nucleic acid or polypeptide microarrays.

In some embodiments, the normal tissue sample comprises non-tumor cells from the same tissue type as the tumor.

In some embodiments, the expression level of the two of more biomarkers is ranked or weighted. The expression level of each of CD44, MMP9, ALDH1A1, Vimentin, hyalurnan, beta-catenin, MFG-E8 and CD68 can be determined. In one embodiment, the expression level of at least one additional biomarker from the tumor sample is determined.

In some embodiments, an existing treatment and/or treatment plan is modified if the expression level of the two or more biomarkers is increased or decreased compared to the expression level of the same biomarker in the normal tissue sample. For example, the existing treatment and/or treatment plan can be modified to increase or decrease the effective dose of ionizing radiation administered to the tumor. The effective dose can be increased by increasing the amount of ionizing radiation administered to the tumor and/or contacting the tumor with a radiosensitizer.

In another aspect, a kit is provided, the kit comprising reagents capable of detecting the expression of a biomarker selected from the group consisting of CD44, MMP9, ALDH1A1, Vimentin, hyaluronan, beta-catenin, MFG-E8, and CD68.

In some embodiments, one or more of the steps of the methods described herein are carried out in vitro. For example, the expression level of the biomarkers described herein can be determined in vitro using immunohistochemistry techniques on tissue samples isolated from a subject. Thus, the step of determining the expression level of the biomarkers described herein does not require that the determining step be performed in vivo (i.e., in the subject). In certain embodiments, the expression level of the biomarkers described herein is ranked or weighted using software providing instructions to a computer.

In some aspects, the disclose provides a biomarker composition for use in a method for treating or diagnosing cancer or tumors. In some embodiments, a composition comprising a biomarker selected from CD44, MMP9, ALDH1A1, Vimentin, hyaluman, beta-catenin, MFG-E8 and/or CD68 for use in a method for treating tumors is provided. In some embodiments, the disclosure provides a biomarker in combination with ionizing radiation for use in a method for treating a tumor. For example, a composition comprising a biomarker selected from CD44, MMP9, ALDH1A1, Vimentin, hyalurnan, beta-catenin, MFG-E8 and/or CD68 in combination with ionizing radiation for use in a method for treating tumors in provided.

In some embodiments, the disclosure describes a composition comprising a biomarker selected from CD44, MMP9, ALDH1A1, Vimentin, hyalurnan, beta-catenin, MFG-E8 and/or CD68 for use in a method for treating tumors, the method comprising modifying the standard radiation treatment protocol if the level of a biomarker described herein is increased in the tumor environment. In some embodiments, the standard radiation treatment protocol is modified by increasing the dose of ionizing radiation administered to the tumor. In some embodiments, the standard radiation treatment protocol is modified by hypofractionation or hyperfractionation of the dose of ionizing radiation. In some embodiments, the standard radiation treatment protocol is modified by further administering an anti-cancer agent to the subject.

In some embodiments, the disclosure describes the use of a composition comprising a biomarker selected from CD44, MMP9, ALDH1A1, Vimentin, hyalurnan, beta-catenin, MFG-E8 and/or CD68 in a method for treating a tumor, the method comprising (i) administering an increased dose of radiation to the subject, where the dose of radiation is increased compared to the dose administered to a subject that does not have elevated levels of a biomarker selected from CD44, MMP9, ALDH1A1, Vimentin, hyalurnan, beta-catenin, MFG-E8 and/or CD68 in the tumor environment; or (ii) administering a dose of radiation to the subject that is similar to the dose administered to a subject that does not have elevated levels of a biomarker selected from CD44, MMP9, ALDH1A1, Vimentin, hyalurnan, beta-catenin, MFG-E8 and/or CD68 in the tumor environment in combination with a pharmaceutically effective amount of an anti-cancer agent.

In some embodiments, a composition comprising a biomarker selected from CD44, MMP9, ALDH1A1, Vimentin, hyalurnan, beta-catenin, MFG-E8 and/or CD68 for use in a diagnostic method practiced on the human or animal body is provided. In one embodiment, a composition comprising a biomarker selected from CD44, MMP9, ALDH1A1, Vimentin, hyalurnan, beta-catenin, MFG-E8 and/or CD68 for use in diagnosing or prognosing cancer or tumors is provided. For example, a composition comprising a biomarker selected from CD44, MMP9, ALDH1A1, Vimentin, hyalurnan, beta-catenin, MFG-E8 and/or CD68 for use in diagnosing tumors is provided, the use comprising:

(a) determining an expression level of a biomarker in a biological or tissue sample from the subject, wherein the biomarker is selected from the group consisting of CD44, MMP9, ALDH1A1, Vimentin, hyaluronan, beta-catenin, MFG-E8, and CD68; and (b) comparing the expression level of the biomarker(s) to an expression level in a normal biological or tissue sample;

wherein an expression level of the biomarker(s) in the biological or tissue sample that is increased or decreased compared to the expression level in the normal biological or tissue sample provides a diagnosis that the subject suffers from a tumor. The use can also provide a prognosis regarding the course of disease, or can be used to identify a subject as a candidate for treatment with ionizing radiation.

Definitions

The term "treating" refers to administering a treatment to a tumor or the subject diagnosed with a tumor. Examples of treatments include ionizing radiation, a chemotherapeutic treatment, or a combination of both. The treatment can also include a radiosensitizer. The term also includes selecting a treatment or treatment plan, and providing treatment options to a healthcare provider or the subject.

The term "ionizing radiation" refers to radiation comprising particles having enough kinetic energy to discharge an electron from an atom or molecule, thereby producing an ion. The term includes both directly ionizing radiation, such as that caused by atomic particles such as alpha particles (helium nuclei), beta particles (electrons), and protons, and indirectly ionizing radiation, such as photons, including gamma rays and x-rays. Examples of ionizing radiation used in radiation therapy include high energy x-rays, electron beams, and proton beams.

The term "tumor environment" or "tumor micro-environment" refers to the immediate small-scale environment of an organism or part of an organism, especially as a distinct part of a larger environment, for example, the immediate small-scale environment of the tumor. The term includes not only the tumor cells themselves, but associated blood-vessels (including endothelial cells and smooth muscle cells), immune system cells and secreted cytokines, epithelial cells, fibroblasts, connective tissue, and/or extracellular matrix that is associated with or surrounds the tumor. The term also refers to the cellular and extracellular environment in which the tumor is located.

The term "standard of care" or "standard radiation treatment protocol" in radiation therapy generally refers to the ionizing radiation dose and administration interval that is generally accepted in the medical field as appropriate treatment for a given tumor, based on the tumor type, size, tissue location, and various other biological parameters. The standard of care or standard treatment protocol varies and is dependent on several factors. For example, for radiation therapy of lung cancer, the standard of care includes multiple fractions (e.g., approximately 30 fractions of low dose radiation, or approximately 60 Gy over 6 weeks) or a smaller number of fractions (e.g., 1-5 fractions) of biologically active doses (e.g., 54 GY in 3 fractions for peripheral tumors, or 48-60 Gy in 4-8 fractions for central tumors) administered to the tumor.

The term "similar dose of ionizing radiation" refers to a dose of ionizing radiation that is identical to, nearly the same, or substantially the same as the effective dose administered to a tumor in another subject, or administered to a tumor in the same subject undergoing an existing course of treatment. The term encompasses the normal and expected variation in ionizing radiation doses delivered by a medical technician skilled in the art of administering ionizing radiation to a tumor in a subject. For example, the term encompasses variation in the effective dose administered to a tumor of less than 10%, less than 5%, or less than 1%. The subject can be a human or non-human animal, such as a companion animal (e.g., cat, dog) or farm animal (e.g., cow, horse, etc.).

The term "small molecule" refers to an organic compound having a molecular weight of less than about 900 daltons, or less than about 500 daltons. The term includes drugs having desired pharmacological properties, and includes compounds that can be taken orally or by injection. The term includes organic compounds that modulate the activity of TGF-beta and/or other molecules associated with enhancing or inhibiting an immune response.

DETAILED DESCRIPTION OF THE INVENTION

Figure 1:
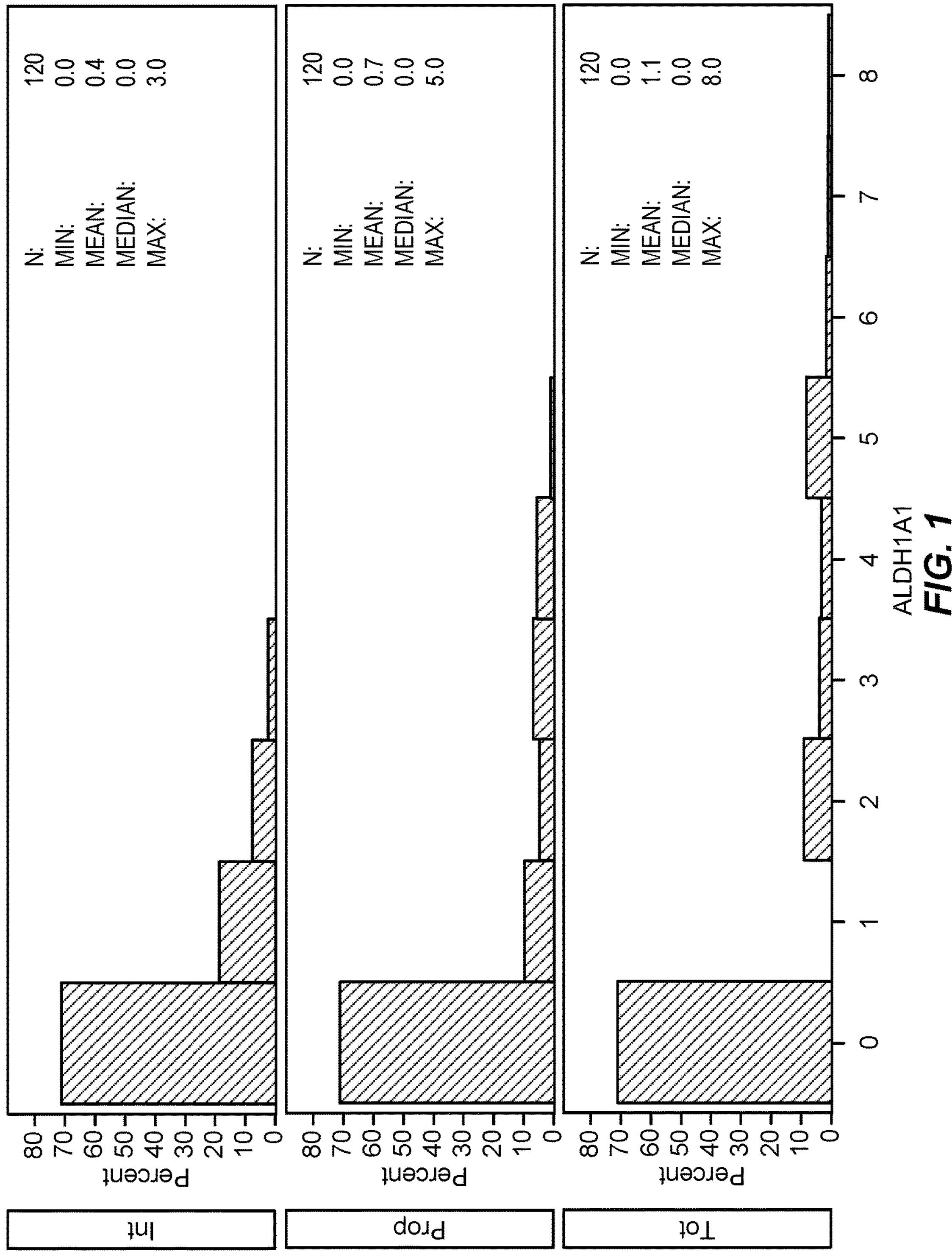
FIG. 1 shows the distribution of ALDH1A1 in biopsy samples from lung cancer patients.
Figure 2:
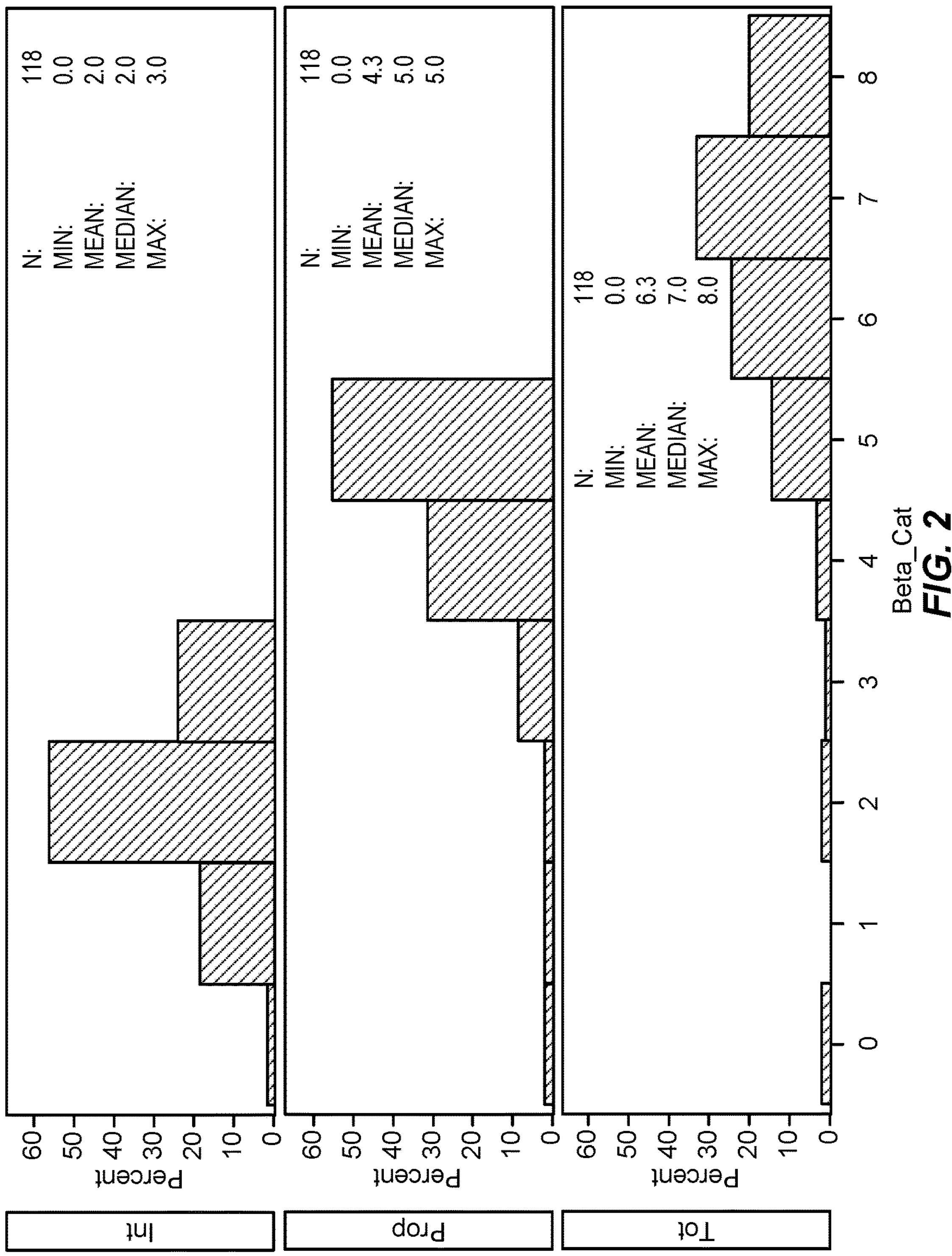
FIG. 2 shows the distribution of Beta-Cat in biopsy samples from lung cancer patients.
Figure 3:
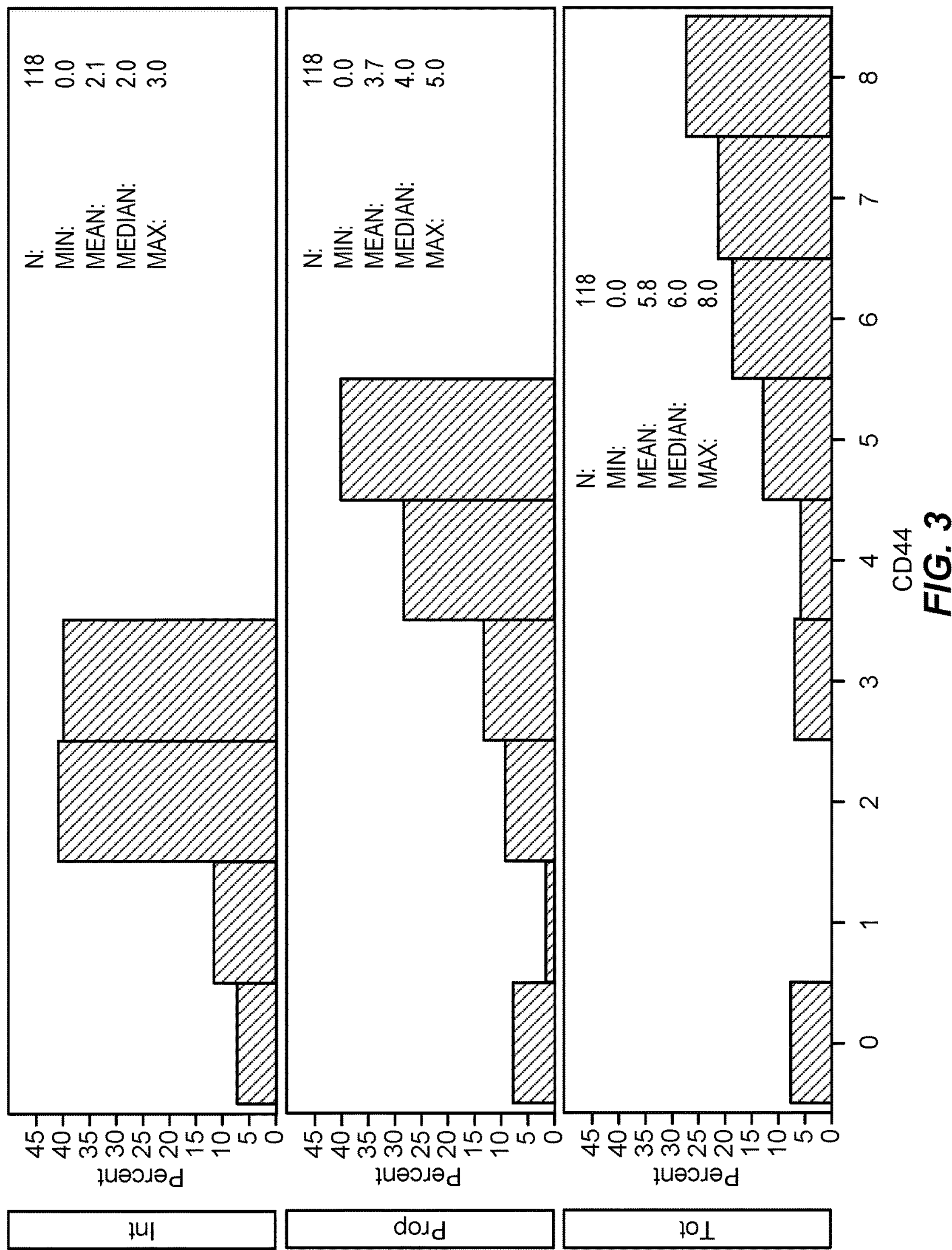
FIG. 3 shows the distribution of CD44 in biopsy samples from lung cancer patients.
Figure 4:
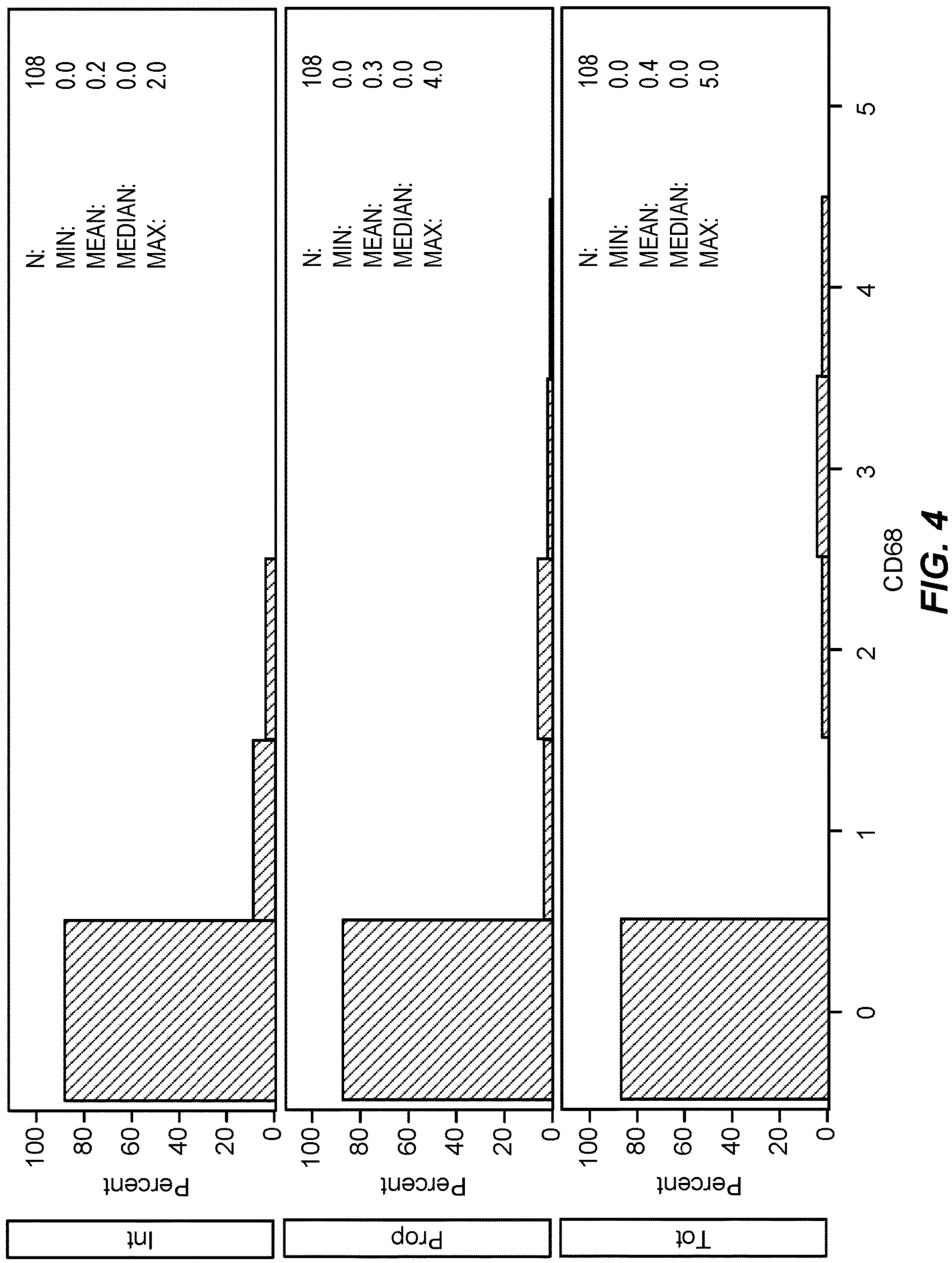
FIG. 4 shows the distribution of CD68 in biopsy samples from lung cancer patients.
Figure 5:
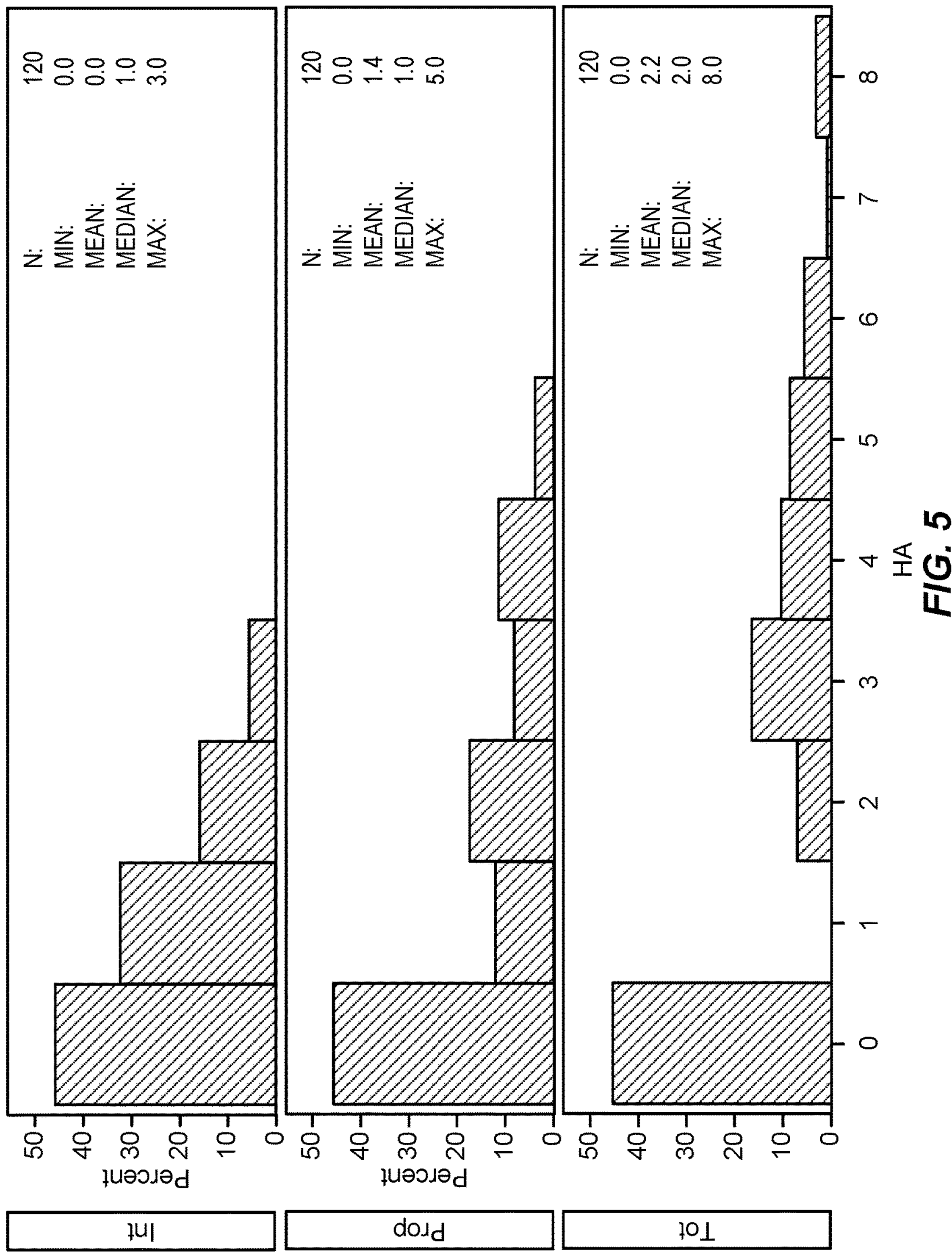
FIG. 5 shows the distribution of HA in biopsy samples from lung cancer patients.
Figure 6:
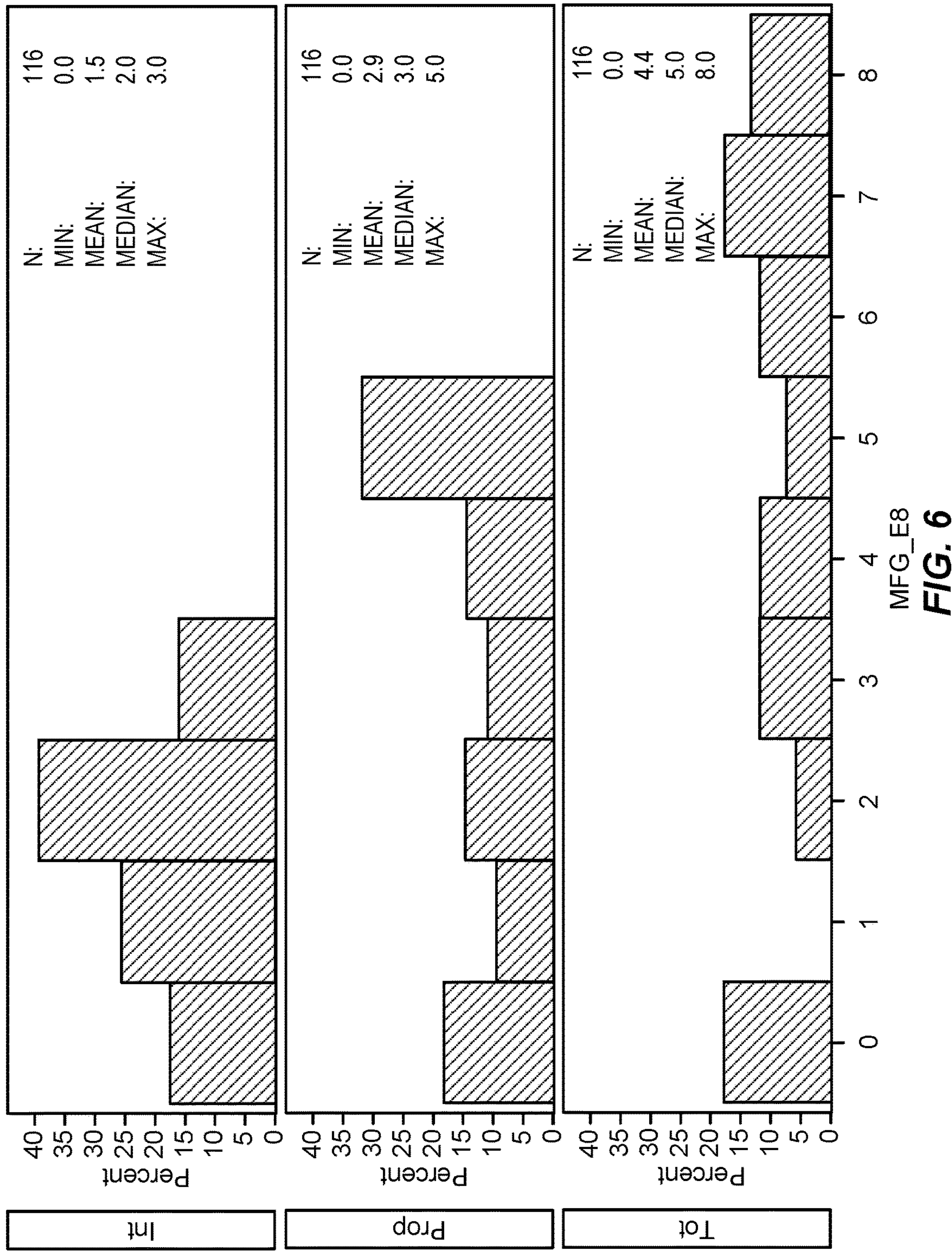
FIG. 6 shows the distribution of MFG-E8 in biopsy samples from lung cancer patients.
Figure 7:
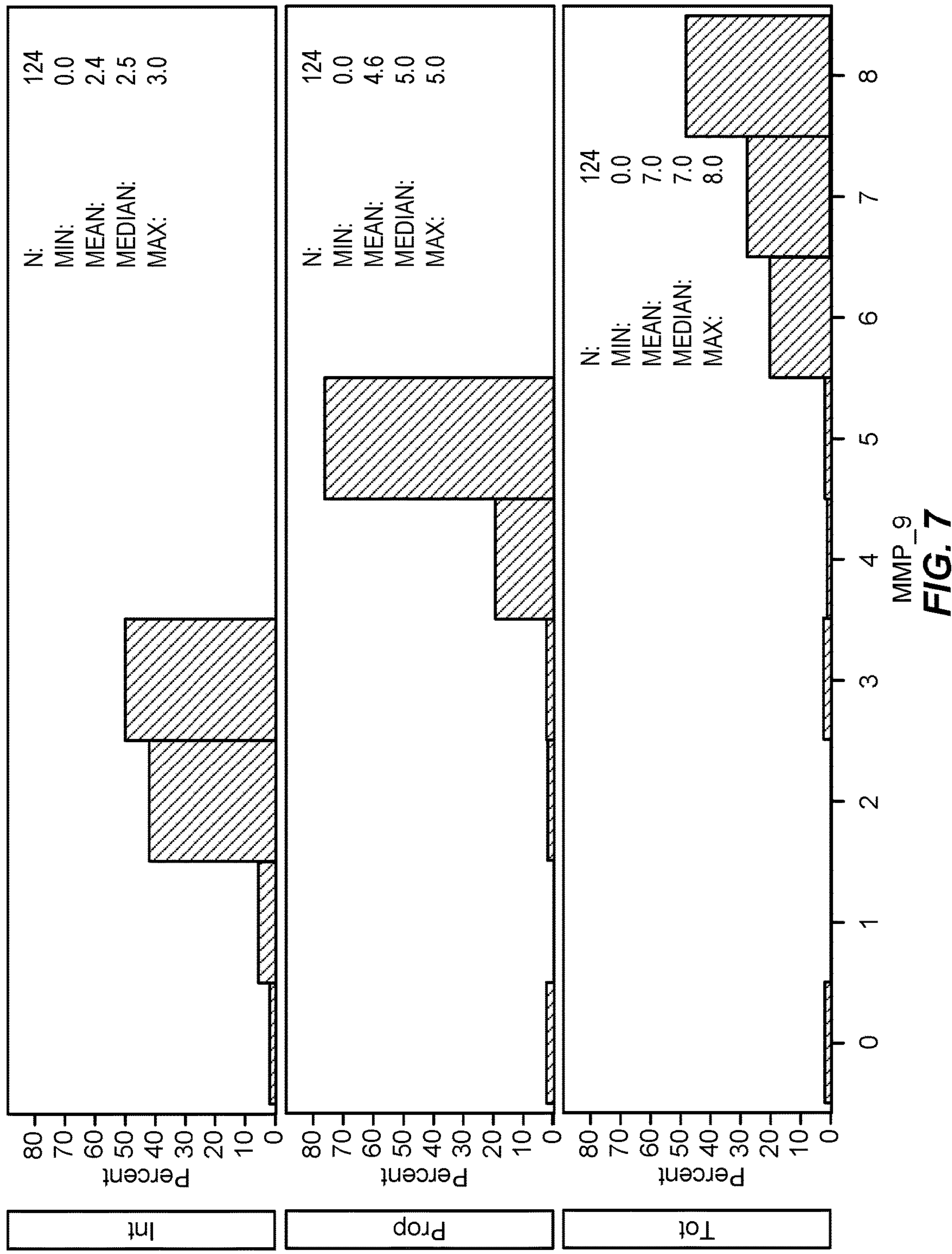
FIG. 7 shows the distribution of MMP9 in biopsy samples from lung cancer patients.
Figure 8:
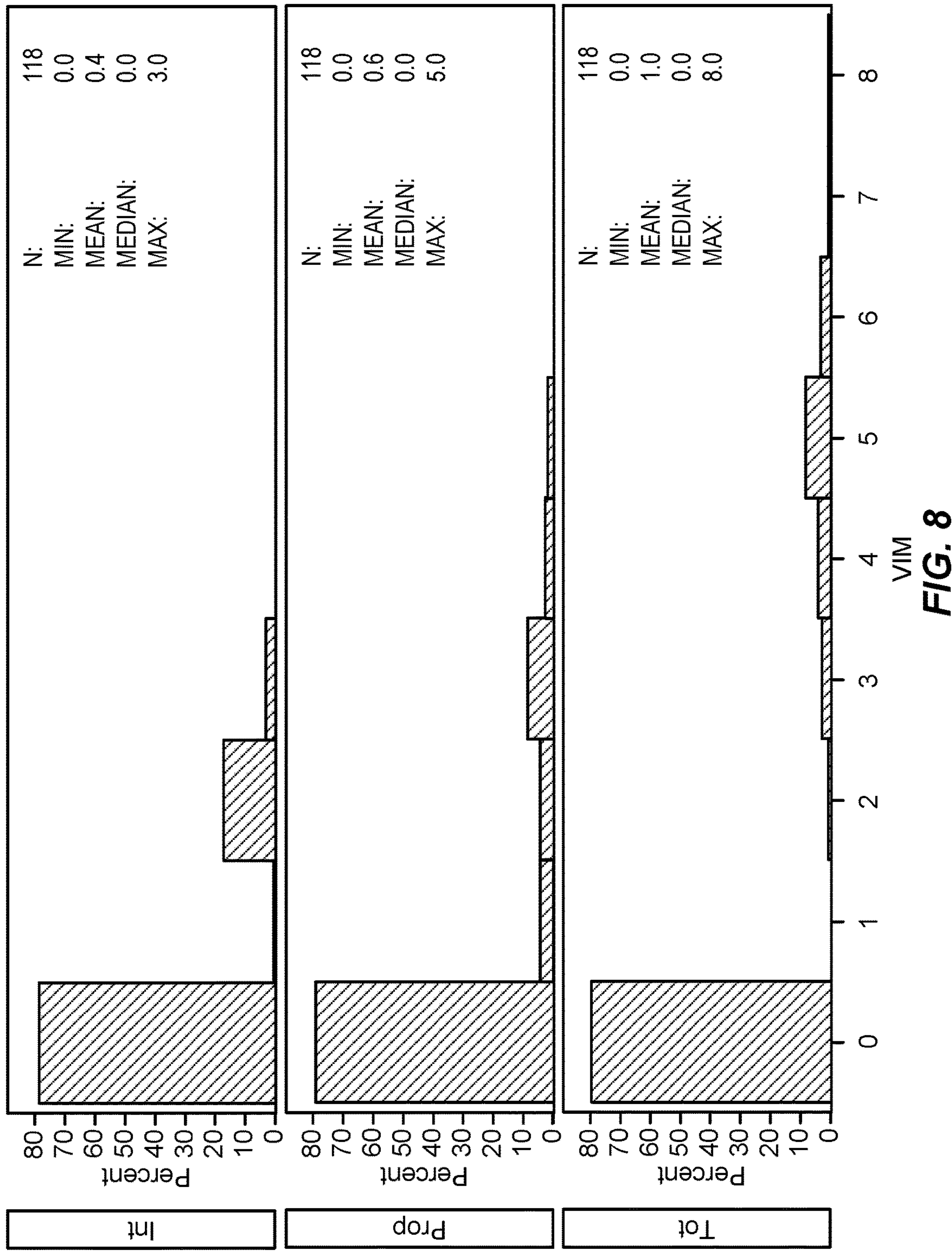
FIG. 8 shows the distribution of VIM in biopsy samples from lung cancer patients.

The methods described herein allow for the classification of patients into groups for receiving optimized radiation treatment based on patient specific biomarker signature. The biomarker signature includes markers that have been shown to correlate with TGF-β expression and to be associated with tumor aggressiveness, radioresistance and poor prognosis. The markers play a key role in the epithelial-mesenchymal transition. The methods described herein provide the dual benefits of anti-tumor efficacy+normal tissue protection when combining TGF-β inhibitors with ionizing radiation to treat cancer patients.

I. Methods

The present disclosure describes methods for treating a tumor in a subject by determining the expression levels of signature biomarkers in a tumor sample, comparing the expression levels in the tumor sample to the expression levels in a normal tissue sample, and treating the tumor if the expression levels in the tumor sample are different from those in the normal tissue sample. In some embodiments, the treatment is ionizing radiation. Thus, the biomarkers provide so called "companion diagnostics" for radiation therapy to treat tumors. The signature biomarkers can also be used to select the appropriate treatment when ionizing radiation is combined with therapeutic tumor treatments such as chemotherapy. Many of the signature biomarkers disclosed herein are associated with the TGF-β signalling pathway. Thus, in some embodiments, the therapeutic agent is an inhibitor of TGF-β or an inhibitor of a component of the TGF-β signalling pathway.

In one aspect, the method is for treating a tumor. The method comprises determining an expression level of two or more biomarkers in a tumor sample from the subject, wherein the two or more biomarkers are selected from the group consisting of CD44, MMP9, ALDH1A1, Vimentin, hyaluronan, beta-catenin, MFG-E8, and CD68. The expression levels of the two or more biomarkers in the tumor sample are compared to the expression levels of the two or more biomarkers in a normal tissue sample. If the expression levels of the two or more biomarkers in the tumor sample are different from the expression levels in the normal tissue sample, for example, increased or decreased relative to the normal tissue level, the tumor is treated.

Thus, in some embodiments, the method comprises (a) determining an expression level of two or more biomarkers in a tumor sample from the subject, wherein the two or more biomarkers are selected from the group consisting of CD44, MMP9, ALDH1A1, Vimentin, hyaluronan, beta-catenin, MFG-E8, and CD68; (b) comparing the expression level of the two or more biomarkers to an expression level in a normal tissue sample; and treating the tumor if the expression level of the two or more biomarkers is increased compared to the expression level in the normal tissue sample.

In some embodiments, the method comprises (a) determining an expression level of two or more biomarkers in a tumor sample from the subject, wherein the two or more biomarkers are selected from the group consisting of CD44, MMP9, ALDH1A1, Vimentin, hyaluronan, beta-catenin, and MFG-E8, and CD68; (b) comparing the expression level of the two or more biomarkers to an expression level in a normal tissue sample; and treating the tumor if the expression level of the two or more biomarkers is decreased compared to the expression level in the normal tissue sample.

In some embodiments, the method comprises determining an expression level of two or more biomarkers in a tumor sample from the subject, wherein the two or more biomarkers are selected from the group consisting of CD44, MMP9, ALDH1A1, Vimentin, hyaluronan, beta-catenin, MFG-E8, and CD68; and treating the tumor if the expression level of the two or more biomarkers is increased compared to the expression level in a normal tissue sample. In some embodiments, the method comprises determining an expression level of two or more biomarkers in a tumor sample from the subject, wherein the two or more biomarkers are selected from the group consisting of CD44, MMP9, ALDH1A1, Vimentin, hyaluronan, beta-catenin, MFG-E8, and CD68; and treating the u or if the expression level of the two or more biomarkers is decreased compared to the expression level in a normal tissue sample.

In some embodiments, the treatment comprises administering ionizing radiation to the tumor. Thus, in some embodiments, the treatment comprises increasing the effective dose of ionizing radiation if the expression level of the two or more biomarkers is increased compared to the expression level in a normal tissue sample. In some embodiments, the treatment comprises decreasing the effective dose of ionizing radiation if the expression level of the two or more biomarkers is decreased compared to the expression level in a normal tissue sample.

In a second aspect, the disclosure describes a method for identifying a subject as a candidate for treatment with ionizing radiation. The method comprises determining an expression level of two or more biomarkers in a tumor sample from the subject, wherein the two or more biomarkers are selected from the group consisting of CD44, MMP9, ALDH1A1, Vimentin, hyalurnan, beta-catenin, MFG-E8, and CD68. As above, the expression levels of the two or more biomarkers in the tumor sample are compared to the expression levels of the two or more biomarkers in a normal tissue sample. If the expression levels of the two or more biomarkers in the tumor sample are different from the expression levels in the normal tissue sample, for example, increased or decreased relative to the normal tissue level, the subject is identified as a candidate for treatment with ionizing radiation.

In some embodiments, the expression level of the two or more biomarkers is increased compared to the expression level in the normal tissue sample, and the subject is identified as a candidate for a first treatment with ionizing radiation. In other embodiments, the expression level of the two or more biomarkers is decreased compared to the expression level in the normal tissue sample, and the subject is identified as a candidate for a second treatment with ionizing radiation. The first and second treatments can be the same or different. In some embodiments, the first treatment comprises increasing the effective dose of ionizing radiation. In some embodiments, the second treatment comprises decreasing the effective dose of ionizing radiation.

In a third aspect, a method is provided for treating a subject having a tumor. The method comprises administering ionizing radiation to a subject that has been selected as having an expression level of two or more biomarkers in a tumor sample that is increased or decreased relative to the expression level of the two or more biomarkers in a normal tissue sample. In some embodiments, the two or more biomarkers are selected from the group consisting of CD44, MMP9, ALDH1A1, Vimentin, hyalurnan, beta-catenin, MFG-E8, and CD68.

In some embodiments, the method comprises administering ionizing radiation to a subject that has been selected as having an expression level of two or more biomarkers in a tumor sample that is increased relative to the expression level of the two or more biomarkers in a normal tissue sample. In some embodiments, the method comprises administering ionizing radiation to a subject that has been selected as having an expression level of two or more biomarkers in a tumor sample that is decreased relative to the expression level of the two or more biomarkers in a normal tissue sample. In some embodiments, the dose of ionizing radiation administered to the subject is increased if the expression level of two or more biomarkers in a tumor sample is increased relative to the expression level of the two or more biomarkers in a normal tissue sample. In some embodiments, the dose of ionizing radiation administered to the subject is decreased if the expression level of two or more biomarkers in a tumor sample is decreased relative to the expression level of the two or more biomarkers in a normal tissue sample.

In a fourth aspect, a method is described for selecting a treatment for a subject having a tumor. The method comprises determining an expression level of two or more biomarkers in a tumor sample from the subject, wherein the two or more biomarkers are selected from the group consisting of CD44, MMP9, ALDH1A1, Vimentin, hyaluronan, beta-catenin, MFG-E8, and CD68. As above, the expression levels of the two or more biomarkers in the tumor sample are compared to the expression levels of the two or more biomarkers in a normal tissue sample. If the expression levels of the two or more biomarkers in the tumor sample are different from the expression levels in the normal tissue sample, for example, increased or decreased relative to the normal tissue level, a treatment is selected for the subject having the tumor.

In another aspect, the biomarkers described herein can also or further be used to determine the prognosis of disease during or after treatment. For example, the expression levels of the biomarkers before and after ionizing radiation therapy can be compared. In some embodiments, if the expression levels of the biomarkers after radiation therapy decrease, then the prognosis is favorable. In some embodiments, if the expression levels of the biomarkers after radiation therapy increase, then the prognosis is unfavorable.

In another aspect, the biomarkers described herein can also or further be used to assess the responsiveness of a patient to a cancer treatment. For example, the expression levels of the biomarkers before and after ionizing radiation therapy can be compared. The method comprises determining an expression level of two or more biomarkers in a tumor sample obtained from the subject, wherein the two or more biomarkers are selected from the group consisting of CD44, MMP9, ALDH1A1, Vimentin, hyalurnan, beta-catenin, MFG-E8, and CD68. In some embodiments, if the expression levels of the biomarkers after radiation therapy decrease, then the patient has responded favorably. In some embodiments, if the expression levels of the biomarkers after radiation therapy increase, then the patient response was unfavorable. This information can be used to guide further therapy. Favorable treatments may be repeated or further increased. Unfavorable treatments can be modified or dropped.

In another aspect, a kit is provided. The kit comprises reagents capable of detecting expression of the biomarkers described herein. In some embodiments, the kit comprises reagents capable of detecting nucleic acid (e.g., RNA) expression of the biomarkers. For example, the kit can comprise oligonucleotide primers that are capable amplifying a nucleic acid expressed by the biomarker genes described herein. In some embodiments, the kit further comprises an oligonucleotide probe that hybridizes to a biomarker nucleic acid or an amplified biomarker nucleic acid, or a complement thereof. Methods of amplifying and detecting nucleic acids are well known in the art, and can comprise PCR, RT-PCR real-time PCR, and quantitative real-time PCR, Northern analysis, sequencing of expressed nucleic acids, and hybridization of expressed and/or amplified nucleic acids to microarrays. In some embodiments, the kit comprises reagents that are capable of detecting proteins expression by the biomarkers described herein. In some embodiments, the reagents are antibodies that specifically bind to biomarker proteins. Methods of detecting protein expression are well known in the art, and include immunoassays, ELISA, Western analysis, and proteomic techniques.

In some embodiments of any of the above aspects and embodiments, the differences in the expression levels of each of the biomarkers in the tumor sample are increased or decreased by at least 10%, 20%, 30%, 40%, 50%, 60%, 70%, 80%, 90% or more compared to the expression level in normal tissue. In some embodiments, the expression levels of each of the biomarkers in the tumor sample are increased or decreased by at least 1-fold, 2-fold, 3-fold, 4-fold, 5-fold, 6-fold, 7-fold, 8-fold, 9-fold, 10 fold or more relative to the expression level in normal tissue.

In some embodiments, the average and/or ranked expression level of all the biomarkers in the tumor sample is increased or decreased relative to the expression level in normal tissue. Thus, in some embodiments, the average and/or ranked expression level of all the biomarkers in the tumor sample is increased or decreased by at least 1.0%, 20%, 30%, 40%, 50%, 60%, 70%, 80%, 90% or more compared to the expression level in normal tissue. In some embodiments, the expression levels in normal tissue are normalized to a control or baseline level. It will be understood that the expression level can also be compared to the expression level in the tumor sample before, after or during a treatment, course of treatment, or treatment plan. Thus, in some embodiments, the expression levels of each of the biomarkers in the tumor sample are increased or decreased by at least 10%, 20%, 30%, 40%, 50%, 60%, 70%, 80%, 90%, or more compared to the expression level in the tumor sample before, during or after treatment.

Further, with regard to any of the above aspects and embodiments, the two or more biomarkers can comprise both CD44 and MMP9; both ALDH1A1 and Vimentin; both hyalurnan and beta-catenin; both CD44 and ALDH1A1; both Vimentin and beta-catenin; both CD44 and hyalurnan; both CD44 and beta-catenin; both CD44 and MFG-E8 or both CD44 and CD68; both MMP9 and hyalurnan; both MMP9 and beta-catenin; both MMP9 and MFG-E8, or both MMP9 and CD68; both ALDH1A1 and hyalurnan; both ALDH1A1 and beta-catenin; both ALDH1A1 and MFG-E8, or both ALDH1A1 and CD68; both Vimentin and MFG-E8; both hyalurnan and MFG-E8; both beta-catenin and MFG-E8, or both CD68 and MFG-E8.

Further, with regard to any of the above aspects and embodiments, the two or more biomarkers can comprise or consist of any combination of the biomarkers, for example any combination of three or more biomarkers, any combination of four or more biomarkers, any combination of five or more biomarkers, any combination of six or more biomarkers, and any combination of seven or more biomarkers. In one embodiment, the combination of biomarkers comprises or consists of CD44, MFG-E8, and CD68.

In another aspect, the expression level of at least one, two, three, four or more of the biomarkers described herein is determined.

In some embodiments, the treatment or selected treatment comprises administering ionizing radiation to the tumor. Thus, in some embodiments, the selected treatment comprises increasing the effective dose of ionizing radiation if the expression level of the two or more biomarkers is increased compared to the expression level in a normal tissue sample. In some embodiments, the selected treatment comprises decreasing the effective dose of ionizing radiation if the expression level of the two or more biomarkers is decreased compared to the expression level in a normal tissue sample. Exemplary radiotherapy treatments are further described herein. In all of the methods described herein, the treatment can further comprise contacting the tumor with a radiosensitizer. A radiosensitizer is any substance that makes tumor cells easier to kill with radiation therapy. Exemplary radiosensitizers include hypoxia radiosensitizers such as misonidazole, metronidazole, and trans-sodium crocetinate. Exemplary radiosensitizers also include DNA damage response inhibitors such as Poly (ADP) ribose polymerase (PARD) inhibitors. In all of the methods described herein, the treatment can further comprise contacting the tumor and/or the tumor environment with an immune modulator. Exemplary immune modulators include agents (antibodies or small molecules) involved in priming and activation of the immune systems, and include agents targeting CTLA4, B7 (B7-1 or B7-2), PD-L1/PD-L2, or PD-1, or agents targeting the binding interactions between CTLA4 and B7-1/B7-2, or PD-1 and PD-L1/PD-L2. Agents targeting CTLA4, B7 (B7-1 or B7-2), PD-L1/PD-L2, and PD-1 include antibodies that specifically bind these molecules, such as monoclonal antibodies. In some embodiments, the agent is an antibody that specifically binds to LAG 3, TIM1, TIM3, MFG-E8, IL-10, or Phosphatidylserine.

Small molecule immune modulators include drugs that enhance or inhibit an immune response, for example, an immune response against a tumor cell. Exemplary small molecule immune modulators include inhibitors of the enzyme Indolamine 2,3-dioxygenase, and inhibitors of alpha-v-beta-3 integrin and alpha-v-beta-5 integrin.

In some embodiments, the treatment further comprises administering a compound that inhibits TGF-beta signaling to the subject. Suitable compounds are described in more detail below.

The biomarkers used in the method will now be described.

A. Biomarkers

The biomarkers described herein correlate with TGF-β expression, and can be used to stratify patients to receive individualized, tailored radiotherapy. The biomarker signature can also be used to monitor the efficacy of TGF-β inhibitors in patients. The biomarker signature is associated with but not limited to the correlation with TGF-β expression. The expression of the biomarkers is associated with radioresistance, aggressiveness and poor prognosis. The marker set includes, but is not limited to, CD44, MMP9, ALDH1A1, Vimentin, hyaluronan, β-catenin MFG-E8, and CD68.

MMP9: A clear correlation can be shown between MMP9, EMT and TGF-3. MMP9 regulates TGF-β and TGF-β regulates MMP9 in multiple settings. MMP9 is localized in the extracellular matrix and tumor stroma, within infiltrated immune cells and in tumor cells. The different cellular locations of MMP9 appear to be correlated with different biological outcomes (more/less aggressive tumor, survival etc.).

Vimentin (VIM): Vimentin is upregulated when TGF-β induces EMT in a variety of cell types, including lung. Vimentin is an intermediate filament protein that characterizes mesenchymal cells as opposed to epithelial cells.

Hyaluronan (HA): Hyaluronan is an abundant glycosaminoglycan component of the extracellular matrix. It is induced by TGF-3, increases MMP9 secretion (likely via CD44), promotes EMT/migration/metastasis, and contributes to chemoresistance and poor prognosis. These findings have been substantiated in a variety of tumor types, including NSCLC. An important receptor for HA is CD44 along with others. The HA-CD44 interaction promotes HER2 signalling and increases Src kinase activity. HA is detected by staining the tissues with a commercially available antibody against Hyaluronic acid, for example, an antibody available from Abcam.

ALDH1A1: Aldehyde dehydrogenase is a detoxifying enzyme known for its role in the oxidation of intracellular aldehydes, which play a role in stem cell differentiation. It is highly expressed in tumorigenic cell populations of various cancers and elevated protein expression has been shown in putative lung stem cell niches during malignant transformation. Expression of ALDH1A is positively correlated with stage and grade of lung tumors and related to poor prognosis in patients with early stage lung cancer.

MFG-E8: MFG-E8 is a macrophage-produced protein that promotes engulfment and clearance of apoptotic cells in tumors. Antibodies neutralizing MFG-E8 function have been shown in experimental models to enhance radiation and chemotherapy. It is likely then, that the levels of MFG-E8 in tumor specimens may have predictive value for efficacy of radiotherapy.

CD68: CD68 is a 110-kD transmembrane glycoprotein that is highly expressed by human monocytes and tissue macrophages. It is a member of the lysosomal/endosomal-associated membrane glycoprotein (LAMP) family. The protein primarily localizes to lysosomes and endosomes with a smaller fraction circulating to the cell surface. It is a type I integral membrane protein with a heavily glycosylated extracellular domain and binds to tissue- and organ-specific lectins or selectins. The protein is also a member of the scavenger receptor family. Scavenger receptors typically function to clear cellular debris, promote phagocytosis, and mediate the recruitment and activation of macrophages (See Entrez listng NCBI).

CD68 is expressed broadly on macrophages including both M1 and M2 subsets. Numerous studies have suggested that macrophages present in the tumor micro-environment can impact growth of tumor cells and some clinical studies have suggested that the macrophage content and location in the tumor and its micro-environment is predictive of clinical outcome in certain cancer patients.

M1 macrophages are referred to as pro-inflammatory macrophages and have the ability to activate type 1 T helper cells (Th1) and to promote an anti-tumor response. In contrast, M2 macrophages activate type 2 T helper cells (Th2) and promote an anti-inflammatory, tissue remodeling response and do not lead to an anti-tumor action. As CD68 is expressed on both M1 and M2 macrophages, its presence cannot, a priori, be used to predict anti-tumor responses or clinical outcome. Thus, the present application describes that CD68 is useful as a biomarker determined in a clinical setting.

Nuclear β-catenin: β-catenin is found associated with E-cadherin at the cell membrane and also in the nucleus, where it accumulates in tumor cells, stem cells or cells undergoing EMT.

The GenBank Accession Nos. for the biomarkers described herein are provided in the Table below.

TABLE 1

| Biomarker Name | Abbreviation | GenBank Accession # (protein) | GenBank Accession # (nucleotide) |
|---|---|---|---|
| Hyaluronate receptor | CD44 | NP_000601 (SEQ ID NO: 1) | NM_000610 (SEQ ID NO: 2) |
| Matrix metalloproteinase | MMP9 | CAC07541 (SEQ ID NO: 3) | AX011001 (SEQ ID NO: 4) |
| Aldehyde dehydrogenase 1A1 | ALDH1A1 | AAP88039 (SEQ ID NO: 5) | AY338497 (SEQ ID NO: 6) |
| Vimentin | VIM | NP_003371 (SEQ ID NO: 7) | NM_003380 (SEQ ID NO: 8) |
| hyaluronan | HA | Not applicable | |
| β-catenin | Beta_Cat | NP_001091680 (SEQ ID NO: 9) | NM_001098210 (SEQ ID NO: 10) |
| Milk fat globule-EGF factor 8 protein | MFG-E8 | NP_005919 (SEQ ID NO: 11) | NM_005928 SEQ ID NO: 12 |
| CD68 | CD68 | ~~NM_001251~~ NP_001242 (SEQ ID NO: 13) | NM_001251 (SEQ ID NO: 14) |

When the biomarkers described herein are referred to by name, it is understood that this includes molecules with similar functions and similar amino acid sequences. Thus, the protein biomarkers described herein include the prototype human protein, as well as homologs and polymorphic variations thereof. For example, the name "CD44 protein" includes the prototype protein (e.g., SEQ ID NO:1), as well as homologs from other species and polymorphic variations thereof. Proteins such as CD44 and CD68 are defined as having similar functions if they have substantially the same biological activity or functional capacity as the wild type protein (e.g., at least 80% of either). Proteins such as CD44 and CD68 are defined as having similar amino acid sequences if they have at least 80%, 85%, 90%, 95%, 96%, 97%, 98%, or 99% sequence identity to the prototype protein. The sequence identity of a protein is determined using the BLASTP program with the defaults wordlength of 3, an expectation (E) of 10, and the BLOSUM62 scoring matrix (see Henikoff and Henikoff, Proc. Natl. Acad. Sci. USA 89:10915-10919, 1992).

A conventional test to determine if a protein homolog or polymorphic variant is inclusive of a protein biomarker described herein is by specific binding to polyclonal antibodies generated against the prototype protein. For example, a CD44 protein includes proteins that bind to polyclonal antibodies generated against the protein of SEQ ID NO:1, and an CD68 protein includes proteins that bind to polyclonal antibodies generated against the prototype protein of SEQ ID NO:13.

Regarding polyclonal antibodies that specifically bind to a protein biomarker described herein, the test protein will bind under designated immunoassay conditions to the specified antibodies at least two times the background, and the specified antibodies do not substantially bind in a significant amount to other proteins present in the sample. For example, polyclonal antibodies raised to CD44, encoded in SEQ ID NO:1, splice variants, or portions thereof, can be selected to obtain only those polyclonal antibodies that are specifically immunoreactive with CD44 and not with other proteins, except for polymorphic variants of CD44. This selection may be achieved by subtracting out antibodies that cross-react with other members of the protein family, as appropriate. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, *Antibodies, A Laboratory Manual* (1988) for a description of immunoassay formats and conditions that can be used to determine specific immunoreactivity). Typically, a specific or selective reaction will be at least twice background signal or noise and more typically more than 10 to 100 times background.

In some embodiments, the method comprises determining the expression level of two or more biomarkers in a tumor sample from the subject. In some embodiments, the biomarker is selected from the group consisting of CD44, MMP9, ALDH1A1, Vimentin, hyaluronan, beta-catenin, MFG-E8, and/or CD68. In some embodiments, the expression level of two, three, four, five, six, seven, or eight of the biomarkers is determined. In some embodiments, the expression level of each of the biomarkers is determined. In some embodiments, the expression level of at least one additional biomarker is determined, wherein the additional biomarker is not in the group consisting of CD44, MMP9, ALDH1A1, Vimentin, hyaluronan, beta-catenin, MFG-E8, and CD68. In some embodiments, the additional biomarker is TGF-β.

In some embodiments, the biomarker signature group consists of CD44, MMP9, ALDH1A1, Vimentin, hyaluronan, beta-catenin, MFG-E8, and CD68. In some embodiments, the biomarker signature group consists essentially of CD44, MMP9, ALDH1A1, Vimentin, hyaluronan, beta-catenin, MFG-E8, and CD68. In some embodiments, the biomarker signature group comprises CD44, MMP9, ALDH1A1, Vimentin, hyaluronan, beta-catenin, MFG-E8, and CD68.

It will be understood that the expression levels of each of the biomarkers in the tumor sample can increase or decrease relative to the expression level of the biomarker in a normal or control tissue sample. For example, the expression level of one biomarker can increase in the tumor sample compared to the expression level in a normal tissue, whereas the expression level of a second biomarker can decrease in the tumor sample compared to the expression level in a normal tissue. The expression level can also be based on the average, combination or sum of the all the biomarker expression levels in the tumor sample. For example, the expression level of each biomarker in the tumor sample can be ranked or weighted to produce a ranked value that is higher or lower than the normal tissue value (which can be a normalized value, for example, set to 1).

In some embodiments, biomarker expression is determined in a biological sample from the subject having a tumor. In some embodiments, the biological sample is a tumor sample. The tumor sample can be a biopsy comprising tumor cells from the tumor. In some embodiments, the biological sample comprises a bodily fluid, such as but not limited to blood, serum, plasma, or urine, and/or cells or tissues from the subject. In some embodiments, the biological sample is a formalin-fixed and paraffin embedded tissue or tumor sample. In some embodiments, the biological sample is a frozen tissue or tumor sample. Thus, in some embodiments, one or more steps of the methods described herein are carried out in vitro. For example, in some embodiments, biomarker expression is determined in vitro.

In some embodiments, the normal tissue sample comprises non-tumor cells from the same tissue type as the tumor. In some embodiments, the normal tissue sample is obtained from the same subject diagnosed with the tumor. A normal tissue sample can also be a control sample of the same tissue-type from a different subject. The expression level of the normal tissue sample can also be an average or mean value obtained from a population of normal tissue samples.

The level of expression of the biomarkers described herein can be determined using any method known in the art. For example, the level of expression can be determined by detecting the expression of a nucleic acid (e.g., RNA or mRNA) or protein encoded by a biomarker gene.

Exemplary methods for detecting expression levels of nucleic acids include without limitation Northern analysis, polymerase chain reaction (PCR), reverse transcription PCR (RT-PCR), real-time PCR, quantitative real-time PCR, and DNA microarrays.

Exemplary methods for detecting expression levels of proteins (e.g., polypeptides) include without limitation immunohistochemistry, ELISA, Western analysis, HPLC, and proteomics assays. In some embodiments, the protein expression level is determined by immunohistochemistry using the Allred method to assign a score (see, e.g., Allred, D. C., Connection 9:4-5, 2005, which is incorporated by reference herein). For example, formalin-fixed, paraffin embedded tissues are contacted with an antibody that specifically binds a biomarker described herein. The bound antibody is detected with a detectable label or secondary antibody coupled with a detectable label, such as a colorimetric label (e.g., an enzymatic substrate produce by HRP or AP). The antibody positive signal is scored by estimating the proportion of positive tumor cells and their average staining intensity. Both the proportion and intensity scores are combined into a total score that weighs both factors.

In some embodiments, the protein expression level is determined by digital pathology. Digital pathology methods include scanning images of tissues on a solid support, such as a glass slide. The glass slides are scanned into whole slide images using a scanning device. The scanned images are typically stored in an information management system for archival and retrieval. Image analysis tools can be used to obtain objective quantitative measurements from the digital slides. For example, the area and intensity of immunohistochemical staining can be analyzed using the appropriate image analysis tools. Digital pathology systems can include scanners, analytics (visualization software, information management systems and image analysis platforms), storage and communication (sharing services, software). Digital pathology systems are available from numerous commercial suppliers, for example. Aperio Technologies, Inc. (a subsidiary of Leica Microsystems GmbH), and Ventana Medical Systems, Inc. (now part of Roche). Expression levels can be quantified by commercial service providers, including Flagship Biosciences (CO), Pathology, Inc. (CA), Quest Diagnostics (NJ), and Premier Laboratory LLC (CO).

B. Treatments

The expression levels of the biomarkers can be used to determine or select a course of treatment in a subject diagnosed with a tumor. For example, in some embodiments, the treatment comprises administering ionizing radiation to the tumor in the subject. The ionizing radiation can also be administered to the entire subject or a portion thereof, especially if the tumor is dispersed or mobile. In some embodiments, the treatment further comprises contacting the tumor with a radiosensitizer. In some embodiments, the treatment further comprises administering a compound or biologic drug, such as an antibody, that inhibits TGF-beta signaling to the subject. Thus, in some embodiments, the treatment comprises administering a standard radiation treatment protocol in combination with a TGF-beta inhibitor.

The course of treatment can be selected based on the expression levels of the biomarkers. For example, the expression levels can be used to determine if radiation therapy is appropriate for the subject (i.e., for making a go/no go decision on radiotherapy). Further, if the expression levels of the biomarkers are increased relative to a normal or control value, then the effective radiation dose to the tumor can be increased, and/or the fractionation schedule modified accordingly. The radiation dose to the blood vessels feeding the tumor can also be increased.

In some embodiments, if the expression levels of the biomarkers are increased relative to a normal or control value, then the treatment can comprise administering ionizing radiation to the tumor. In some embodiments, if the expression levels of the biomarkers are decreased relative to a normal or control value, then the treatment can comprise decreasing the amount of ionizing radiation administered to the tumor.

The treatment can also comprise modifying an existing course of treatment. For example, in some embodiments, the existing course of treatment is modified to increase the effective dose of the ionizing radiation administered to the tumor. In some embodiments, the effective dose of ionizing radiation is increased by increasing the amount of ionizing radiation administered to the tumor and/or contacting the tumor with a radiosensitizer. In some embodiments, the existing course of treatment is modified to decrease the effective dose of the ionizing radiation administered to the tumor. In some embodiments, the treatment comprises modifying a standard radiation treatment protocol in combination with administering a TGF-beta inhibitor.

In some embodiments, the effective dose of ionizing radiation administered to the tumor is increased if the level of one or more biomarkers described herein is elevated in the tumor environment. For example, the effective dose of ionizing radiation is increased as compared to the standard of care for a subject that does not have elevated levels of the biomarker(s) in the tumor environment. This applies to subjects who are currently not undergoing radiation therapy as well as modifying an existing course of treatment for subjects undergoing radiation therapy. Thus, the effective dose of ionizing radiation can be increased from the current effective dose if the subject is already undergoing radiation therapy for a tumor. The radiation therapy can be modified to reduce the constraints on neighboring healthy tissue. For example, if the biomarker level in the tumor environment indicates more aggressive radiation therapy is required, the treatment plan can be modified so that the constraints on the border between healthy tissue and tumor tissue are decreased. This would result in a trade-off between damaging some healthy tissue in order to kill more of the tumor tissue.

In some embodiments, the treatment comprises a combination of radiation therapy and an anti-cancer agent (including a radiosensitizer). In some embodiments, the effective dose of ionizing radiation administered to the tumor is not changed (e.g., relative to the standard of care or relative to an existing course of treatment) when an anti-cancer agent is administered to the subject. For example, in some embodiments, the subject is administered an effective dose of ionizing radiation that is the same or similar to that administered to a subject that does not have elevated levels of one or more biomarkers described herein in the tumor environment, and the subject is further administered an anti-cancer agent. In some embodiments, the effective dose of ionizing radiation administered to the tumor is based on the standard of care for a subject that does not have elevated levels of the biomarker(s) in the tumor environment, and the subject is further administered an anti-cancer agent. In some embodiments involving an existing course of treatment, the effective dose of ionizing radiation is maintained at the current effective dose, and an anti-cancer agent is administered to the subject in combination with the ionizing radiation if the level of one or more biomarkers described herein is elevated in the tumor environment.

In some embodiments, the subject is administered an increased effective dose of ionizing radiation if the expression of CD44 or CD68 is elevated in the tumor environment. In some embodiments, the subject is administered an effective dose of ionizing radiation that is the same or similar to the effective dose administered to a subject that does not have elevated levels of CD44 or CD68 in the tumor environment (e.g., according to the current standard of care), in combination with a pharmaceutically effective amount of an anti-cancer agent, if the expression of CD44 or CD68 is elevated in the tumor environment. In some embodiments, the subject is administered an increased effective dose of ionizing radiation if the level of CD44 is increased and the level of MFG-E8 is decreased in the tumor environment. In some embodiments, the subject is administered an effective dose of ionizing radiation that is the same or similar to the effective dose administered to a subject that does not have increased levels of CD44 and decreased levels of MFG-E8 in the tumor environment (e.g., according to the current standard of care), in combination with a pharmaceutically effective amount of an anti-cancer agent, if the level of CD44 is increased and the level of MFG-E8 is decreased in the tumor environment. The above embodiments apply to subjects who are currently not undergoing radiation therapy as well as modifying an existing course of treatment for subjects undergoing radiation therapy.

In some embodiments, the treatment plan is developed and/or modified based on the expression levels of the biomarkers described herein.

The course of treatment can also be selected by using an algorithm that determines the expression level of the biomarkers in the tumor sample relative to the level in the normal sample. The algorithm can be a linear regression algorithm that includes the biomarker expression levels and coefficients (i.e., weights) for combining the expression levels. In some embodiments, the algorithm comprises a least squares fit to calculate the coefficients. If the algorithm determines that the expression level of the biomarkers in the tumor sample is increased or decreased relative to the normal sample, then the appropriate course of treatment can be assigned. In some embodiments, the algorithm is a nonparametric regression tree. In some embodiments, standard statistical methods were used to analyze the data to determine which biomarkers were most predictive of clinical survival or local tumor control failure.

In some embodiments, the method described herein is a computer implemented method. In some embodiments, the computer implemented method comprises a linear regression model that assigns a ranked or weighted value to the expression levels of the biomarkers described herein. In some embodiments, the disclosure provides a computer-readable medium, the medium providing instructions to cause a computer to perform a method described herein. For example, the medium can provide instructions to cause a computer to assign a ranked or weighted value to the expression levels of the biomarkers described herein.

C. Therapeutic Radiation Doses

The expression levels of the tumor biomarkers described herein can be used to optimize treatment of patients with radiotherapy. For example, the therapeutic dose of the radiation administered to the tumor or subject can be adjusted based on the expression levels of the biomarkers. As is well known in the art, the effective dose of ionizing radiation varies with the type of tumor and stage of cancer that needs to be treated. The effective dose can also vary based on other treatment modalities being administered to the patient, for example chemotherapeutic treatments and surgical treatments, and whether the radiation is administered pre- or post-surgery. In general, a curative therapeutic dose for a solid epithelial tumor ranges from about 60 to 80 gray (Gy), whereas a curative dose for a lymphoma is about 20 to 40 Gy. In general, preventative doses can be 45-60 Gy.

As is well known in the art, the therapeutic dose can be delivered in fractions. Fractionation refers to spreading out the total dose of radiation over time, for example, over days, weeks or months. The dose delivered in each fraction can be about 1.5-2 Gy per day. The treatment plan can include a fraction treatment one or more times per day, every other day, weekly, etc. depending on the treatment needs of each patient. For example, a hypofractionation schedule comprises dividing the total dose into several relatively large doses, and administering the doses at least one day apart. Exemplary hypofraction doses are 3 Gy to 20 Gy per fraction. An exemplary fractionation schedule that can be used to treat lung cancer is Continuous Hyperfractionated Accelerated Radiation therapy (CHART), which consists of three small fractions per day.

The biomarkers described herein are useful in developing and modifying treatment plans for patients diagnosed with a tumor or cancer. The treatment plan can include visualizing or measuring the tumor volume that needs to be irradiated, the optimal or effective dose of radiation administered to the tumor, and the maximum dose to prevent damage to nearby healthy tissue or organs at risk. Algorithms can used in treatment planning, and include dose calculation algorithms based on the particular radiotherapy technique parameters employed, e.g., gantry angle, MLC leaf positions, etc., and search algorithms which use various techniques to adjust system parameters between dose calculations to optimize the effectiveness of the treatment. Exemplary dose calculation algorithms include various Monte Carlo ("MC") techniques and pencil beam convolution ("PBC"). Exemplary search algorithms include various simulated annealing ("SA") techniques, algebraic inverse treatment planning ("AITP"), and simultaneous iterative inverse treatment planning "SIITP"). Such techniques, and others, are well known in the art, and are included within the scope of this disclosure.

Treatment planning algorithms may be implemented as part of an integrated treatment planning software package which provides additional features and capabilities. For example, a dose calculation algorithm and search algorithm may be used to optimize a set of fluence maps at each gantry angle, with a separate leaf sequencer used to calculate the leaf movements needed to deliver them. Alternatively, a dose calculation algorithm and search algorithm may be used to directly optimize leaf movements and other machine parameters. The Eclipse™ Treatment Planning System offered by the assignee of the present invention includes such an integrated software program. Methods for optimizing treatment plans are described in U.S. Pat. No. 7,801,270, which is incorporated by reference herein.

In some embodiments, the biomarkers described herein can be used to monitor the progress of tumor control after radiation therapy. For example, the expression levels of the biomarkers before and after ionizing radiation therapy can be compared. In some embodiments, if the expression levels of biomarkers increase after radiotherapy, this suggests that the tumor is continuing to grow in size. Thus, the radiation treatment can be modified based on monitoring tumor growth using the biomarkers described herein.

The biomarkers described herein can be used with any radiation therapy technique known in the art. Radiation therapy techniques include external-beam radiotherapy ("EBRT") and Intensity Modulated Radiotherapy ("IMRT"), which can be administered by a radiotherapy system, such as a linear accelerator, equipped with a multileaf collimator ("MLC"). The use of multileaf collimators and IMRT allows the patient to be treated from multiple angles while varying the shape and dose of the radiation beam, thereby avoiding excess irradiation of nearby healthy tissue. Other exemplary radiation therapy techniques include stereotactic body radiotherapy (SBRT), volumetric modulated arc therapy, three-dimensional conformal radiotherapy ("3D conformal" or "3DCRT"), image-guided radiotherapy (IGRT). The radiation therapy techniques can also include Adaptive radiotherapy (ART), a form of IGRT that can revise the treatment during the course of radiotherapy in order to optimize the dose distribution depending on patient anatomy changes, and organ and tumour shape. Another radiation therapy technique is brachytherapy. In brachytherapy, a radioactive source is implanted within the body of the subject, such that the radioactive source is near the tumor. As used herein, the term radiotherapy should be broadly construed and is intended to include various techniques used to irradiate a patient, including use of photons (such as high energy x-rays and gamma rays), particles (such as electron and proton beams), and radiosurgical techniques. Further, any method of providing conformal radiation to a target volume is intended to be within the scope of the present disclosure.

Chemotherapeutic Agents

In some embodiments, the radiation therapy is administered in combination with one or more chemotherapeutic agents (i.e., anti-cancer agents). The chemotherapeutic agents include radiosensitizers, anti-tumor or anti-cancer agents, and/or inhibitors of TGF-beta signaling. In some embodiments, the radiation therapy is administered in combination with an immune system modulator.

1. Radiosensitizers

In some embodiments, the chemotherapeutic agent is a radiosensitizer. Exemplary radiosensitizers include hypoxia radiosensitizers such as misonidazole, metronidazole, and trans-sodium crocetinate, a compound that helps to increase the diffusion of oxygen into hypoxic tumor tissue. The radiosensitizer can also be a DNA damage response inhibitor interfering with base excision repair (BER), nucleotide excision repair (NER), mismatch repair (MMR), recombinational repair comprising homologous recombination (HR) and non-homologous end-joining (NHEJ), and direct repair mechanisms. SSB repair mechanisms include BER, NER, or MMR pathways whilst DSB repair mechanisms consist of HR and NHEJ pathways. Radiation causes DNA breaks that if not repaired are lethal. Single strand breaks are repaired through a combination of BER, NER and MMR mechanisms using the intact DNA strand as a template. The predominant pathway of SSB repair is the BER utilizing a family of related enzymes termed poly-(ADP-ribose) polymerases (PARP). Thus, the radiosensitizer can include DNA damage response inhibitors such as Poly (ADP) ribose polymerase (PARP) inhibitors.

2. Anti-Tumor Agents

In some embodiments, the chemotherapeutic agent is an anti-cancer agent. Examples of anti-cancer agents include hypoxic cytotoxins, such as tirapazamine. In some embodiments, the anti-cancer agent is a drug that is currently approved for treating cancer or tumors. In some embodiments, the anti-cancer agent is approved for treating lung cancer, for example, Cisplatin, Taxol, Paclitaxal, Abitrexate, Bevacizumab, Folex, Gemcitabine, or Iressa. In some embodiments, the anti-cancer agent targets a fusion protein, and includes agents such as Crizotinib.

3. TGF-β Inhibitors

There is substantial evidence that TGF-β plays a crucial role in the response to ionizing radiation. TGF-β is a pleiotropic cytokine that is important in normal tissue homeostatis, regulates inflammation and immune responses, and suppresses epithelial proliferation. TGF-β is activated in irradiated tissues, presumably because the latent TGF-β complex has a specific—redox-sensitive conformation activated by reactive oxygen species, which are generated by radiation. There is significant evidence for activated TGF-β to contribute to metastasis, to drive function-compromising fibrosis, to promote tumor cell proliferation, and to suppress immune surveillance. Thus, in some embodiments, the chemotherapeutic agent is a TGF-β inhibitor. There are four major classes of TGF-β inhibitors, including ligand traps (e.g. 1D11 or Fresolimumab), antisense oligonucleotides (e.g., Trabedersen), small molecule receptor kinase inhibitors (e.g., LY2109761 or LY2157299), and peptide aptamers (e.g. Trx-SARA). Any suitable TGF-B inhibitor known in the art can be used in the methods, and is considered within the scope of the methods described herein. TGF-beta inhibitors also include agents that inhibit the production of activated TGF-beta.

4. Immune Modulators

Examples of immune modulators include antibodies that bind molecules expressed on the surface of immune system cells, such as antigen presenting cells and T-cells. Immune modulators also include small molecules that inhibit or stimulate the immune system. One non-limiting example of a small molecule immune modulator is an inhibitor of the enzyme Indolamine 2,3-dioxygenase.

EXAMPLES

Example 1

This example describes the association between the biomarkers described herein and clinical outcomes (survival and local tumor control) for lung cancer patients treated with radiation.

Statistical Methods

In order to understand the characteristics of the population under investigation, descriptives of both demographics and biomarker levels (intensity, proportion, and total; abbreviated "Int," "Prop," and "Tot" throughout) were first examined. Biomarker levels were examined using Allred scoring system. The Allred scoring system allows for measurement of biomarker expression as monitored by immunohistochemistry. It takes into account the percentage/proportion of cells that stain by immunohistochemistry (on a scale of 0-5) and the intensity of that staining (on a scale of 0-3), leading to a possible total score of 8. Survival time was then modeled using cox proportional hazards models, defined as date of biopsy to date of death or last follow-up. Univariate models were examined first, followed by multivariate models to determine factors most predictive of survival. Multivariate models were built using stepwise regression, and were also further examined for possible effect modification.

We also dichotomized each biomarker using two methods: 1) a cut point suggested by a nonparametric regression tree, where a cut point is found that "best" separates subjects by survival time, and 2) by a visual examination of where clear separation in the distributions exist. Lastly, we examined how predictive biomarkers and clinical characteristics were of local tumor control failure using logistic regression models. Statistical significance was set to level 0.05 for all analyses.

Results

A total of 133 deceased lung cancer patients were included in the analysis. The median survival time among all patients was 1.5 years. The majority of patients were white males; most underwent curative radiation therapy, were diagnosed at stage III, and were current smokers (Table 2). The expression pattern of biomarkers varied greatly: ALDH1A1, CD68, HA, and VIM tended to have low values, while Beta_Cat, CD44, MFG_E8 and MMP_9 tended to have high values (See FIGS. 1-8).

TABLE 2

Descriptive Patient Characteristics (N = 133)

| Variable | Level | N (%) or N, Mean (SD), [Min, Max] |
|---|---|---|
| Gender | Female | 56 (42%) |
| | Male | 77 (58%) |
| Race | Black | 52 (40%) |
| | Non-Black | 80 (60%) |
| Radiation Therapy | Curative | 114 (86%) |
| | Curative/SBRT | 5 (4%) |
| | SBRT | 14 (10%) |
| Treatment Group | RT Alone | 42 (33%) |
| | Chemo RT | 86 (67%) |
| Local Tumor Control | Yes | 100 (75%) |
| | No | 33 (25%) |
| Stage at Diagnosis | I | 25 (20%) |
| | II | 18 (14%) |
| | III | 77 (61%) |
| | IV | 6 (5%) |
| Smoking | current smoker | 73 (57%) |
| | not smoker | 2 (2%) |
| | past smoker | 51 (39%) |
| | unknown | 3 (2%) |
| Tumor Type | Adenocarcinoma | 23 (20%) |
| | Squamous | 95 (80%) |
| Age | | 133, 78 (11), [52, 98] |
| Median Household Income | <$15,000 | 6 (5%) |
| | ≥$15,000-<$30,000 | 33 (27%) |
| | ≥$30,000-<$50,000 | 42 (34%) |
| | ≥$50,000-<$75,000 | 28 (23%) |
| | ≥$75,000 | 13 (11%) |

Univariate survival models indicated that the only patient characteristics exhibiting significant differences in risk were race, where blacks had nearly a 1.5 times greater risk of death than non-blacks (p-value=0.038, Table 3). Additionally, crude estimates of differences in survival by biomarker levels indicated that higher levels of CD68 were associated with a statistically significant higher risk of death. Namely, a one unit increase in CD68 Prop increased the risk of death by 49%, while a one unit increase in CD68 Tot increased the risk of death by 25% (p-value=0.008, p-value=0.02 for Prop and Tot, respectively). Further, a marginally significant protective effect was observed for MMP_9 (p-value=0.05, p-value=0.054 for Prop and Tot, respectively). Using the optimal cut point method for each biomarker based on regression trees, CD68 and VIM groups displayed association with survival, and there was some marginal significance of MFG_E8. Using cut points determined by visual examination, MFG_E8 groups were associated with survival. In these plots, CD68 (Prop and Tot) and VIM (Prop and Tot) both increased risk, while MFG_E8 decreased risk.

TABLE 3

| Univariate Survival Estimates | | | | |
|---|---|---|---|---|
| Parameter | Level | Hazard Ratio (HR) (95% CI) | Comparison p-value | Overall p-value |
| Patient Characteristics | | | | |
| Gender | Male vs. Female | 1.03 (0.72, 1.46) | | 0.88 |
| Race | Black vs. Non-Black | 1.47 (1.02, 2.1) | 0.038 | 0.038 |
| Smoking | not smoker vs. current smoker | 2 (0.48, 8.25) | 0.34 | 0.37 |
| | past smoker vs. current smoker | 1.12 (0.78, 1.61) | 0.54 | |
| | unknown vs. current smoker | 2.46 (0.76, 7.92) | 0.13 | |
| Stage at Diagnosis | II vs. I | 1.07 (0.58, 1.96) | 0.84 | 0.98 |
| | III vs. 1 | 0.98 (0.62, 1.55) | 0.93 | |
| | IV vs. I | 0.9 (0.37, 2.2) | 0.82 | |
| Stage II or III at Diagnosis | Yes vs. No | 1.16 (0.78, 1.74) | 0.46 | 0.46 |
| Tumor Type | Squamous vs. Adenocarcinoma | 1.15 (0.73, 1.82) | 0.54 | 0.54 |
| Treatment Group | chemo RT vs. RT Alone | 0.72 (0.49, 1.05) | 0.088 | 0.088 |
| Local Tumor Control | Yes vs. No | 1.06 (0.72, 1.58) | 0.76 | 0.76 |
| Radiation Therapy | Curative/SBRT vs. Curative | 0.55 (0.22, 1.36) | 0.19 | 0.20 |
| | SBRT vs. Curative | 1.39 (0.8, 2.44) | 0.25 | |
| Age | | 1 (0.99, 1.02) | | 0.56 |
| Biomarkers | | | | |
| ALDH1A1_Int | | 1 (0.78, 1.29) | | 1.00 |
| ALDH1A1_Prop | | 0.98 (0.85, 1.14) | | 0.82 |
| ALDH1A1_Tot | | 0.99 (0.9, 1.09) | | 0.90 |
| Beta_Cat_Int | | 0.84 (0.66, 1.09) | | 0.19 |
| Beta_Cat_Prop | | 0.95 (0.8, 1.13) | | 0.57 |
| Beta_Cat_Tot | | 0.95 (0.85, 1.06) | | 0.32 |
| CD44_Int | | 1.11 (0.9, 1.36) | | 0.33 |
| CD44_Prop | | 1.06 (0.93, 1.2) | | 0.38 |
| CD44_Tot | | 1.04 (0.96, 1.14) | | 0.32 |
| CD68_Int | | 1.33 (0.89, 1.99) | | 0.16 |
| CD68_Prop | | 1.49 (1.11, 1.99) | | 0.008 |
| CD68_Tot | | 1.25 (1.04, 1.51) | | 0.02 |
| HA_Int | | 0.94 (0.76, 1.17) | | 0.59 |
| HA_Prop | | 0.93 (0.83, 1.04) | | 0.20 |
| HA_Tot | | 0.96 (0.88, 1.04) | | 0.27 |
| MFG_E8_Int | | 0.92 (0.74, 1.14) | | 0.44 |
| MFG_E8_Prop | | 0.92 (0.83, 1.02) | | 0.10 |
| MFG_E8_Tot | | 0.95 (0.88, 1.02) | | 0.15 |
| MMP_9_Int | | 0.83 (0.62, 1.11) | | 0.21 |
| MMP_9_Prop | | 0.8 (0.64, 1) | | 0.05 |
| MMP_9_Tot | | 0.87 (0.76, 1) | | 0.054 |
| VIM_Int | | 1.02 (0.83, 1.25) | | 0.87 |

TABLE 3-continued

| Univariate Survival Estimates | | | | |
|---|---|---|---|---|
| Parameter | Level | Hazard Ratio (HR) (95% CI) | Comparison p-value | Overall p-value |
| VIM_Prop | | 1.02 (0.87, 1.19) | | 0.78 |
| VIM_Tot | | 1.01 (0.92, 1.11) | | 0.81 |

Table 4 displays the results of a final multivariate model built using stepwise regression. All patient characteristics and 24 biomarker measurements were eligible for model inclusion. The significance level required to both enter the model and be retained in the model was 0.05. This model selection procedure only retained CD68 Prop and race in the model, indicating that these two covariates are most predictive of survival outcomes, among all covariates considered.

TABLE 4

| Final Survival Model | | |
|---|---|---|
| Parameter | HR (95% CI) | p-value |
| CD68 Prop | 1.61 (1.19, 2.18) | 0.002 |
| black vs. non-black | 1.59 (1.05, 2.41) | 0.028 |

It should be noted that since correlation within a biomarker is high (comparing the three different measures of Int, Prop and Tot), it is unlikely that multiple measurement types of the same biomarker would be retained in the model, due to information redundancy.

Predictive Ability of Biomarkers for Local Tumor Control

Figure 9:
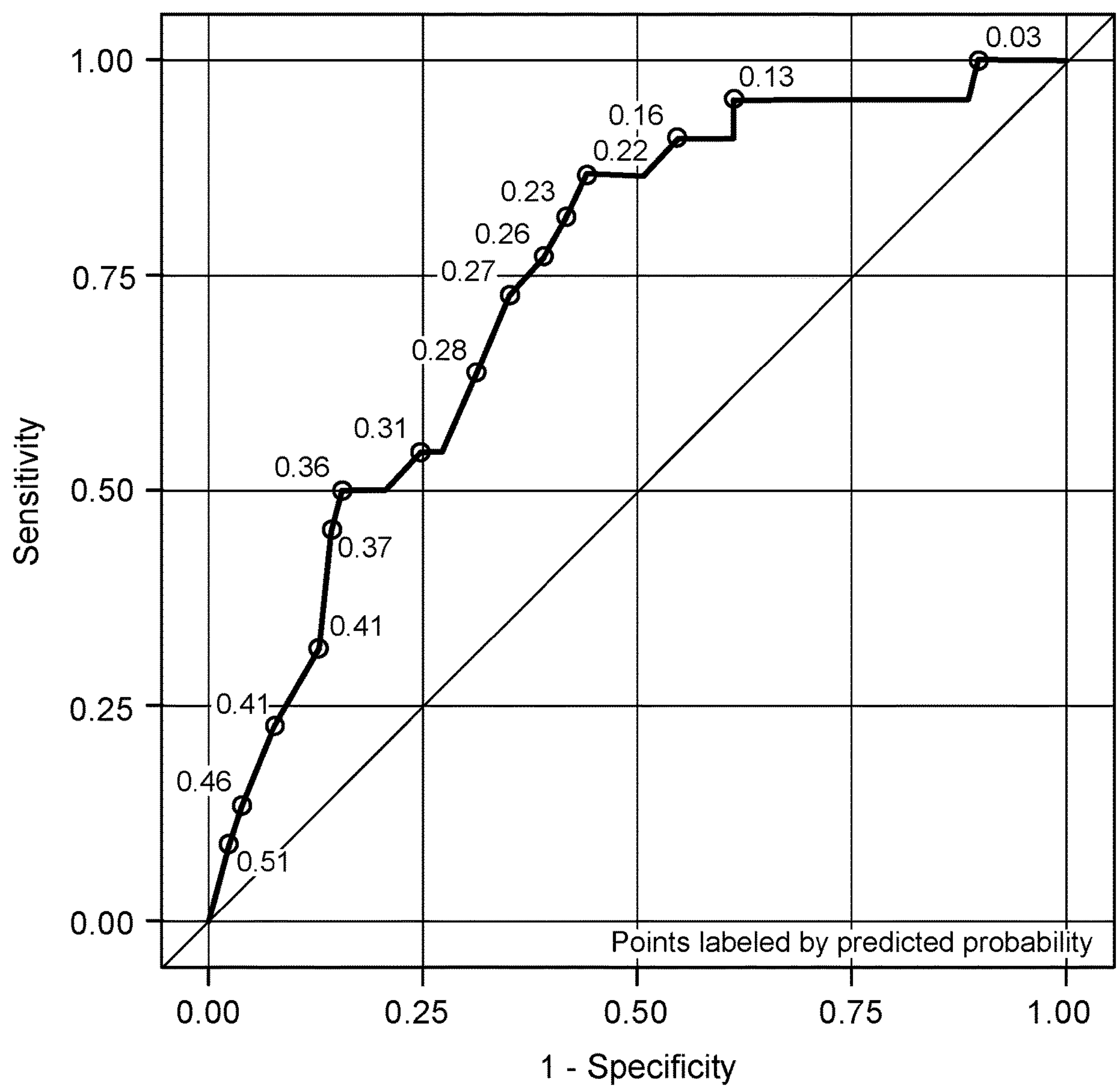
FIG. 9 shows the ROC curve for the variables CD44 (Tot), MFG_E8 (Prop) and tumor type from a multivariate model to predict local tumor control.

We also determined if biomarkers, along with clinical characteristics, were predictive of local tumor control failure. We use the Area Under the ROC (Receiver Operating Characteristics) Curve (AUC) as a measure of predictive ability, where the ROC curve is built from various probability cut points from a logistic regression model. An AUC of 0.5 indicates "no better than random chance" and an AUC of 1 indicates "perfect prediction". As seen in Table 5, Tumor Type, CD44, and MFG_E8 all had a significantly better than random chance prediction ability. CD44 and squamous tumors were risk factors for local tumor control failure, while MFG_E8 had a protective effect. To find a more predictive model of local tumor control failure, we then determined which combination of these three factors resulted in the highest AUC. The variables CD44 (Tot), MFG_E8 (Prop) and tumor type combined resulted in an AUC of 0.74 (p-value<0.001, 95% CI=(0.63, 0.85)). The ROC curve from this multivariate model can be seen in FIG. 9.

TABLE 5

| Predictive Ability Of Biomarkers For Local Tumor Control Failure (Univariate) | | | | | | |
|---|---|---|---|---|---|---|
| | | Odds Ratio | | | Area Under the Curve | |
| Parameter | Level | OR (95% CI) | Comparison p-value | Overall p-value | AUC (95% CI) | p-value |
| Patient Characteristics | | | | | | |
| Gender | Male vs. Female | 1.16 (0.52, 2.59) | | 0.72 | 0.52 (0.42, 0.62) | 0.72 |
| Race | Black vs. Non-Black | 1.18 (0.53, 2.63) | | 0.68 | 0.52 (0.42, 0.62) | 0.69 |
| Age | | 0.98 (0.94, 1.01) | | 0.18 | 0.59 (0.47, 0.7) | 0.14 |
| Radiation Therapy | Curative/SB RT vs. | 0.7 (0.08, 6.51) | 0.75 | 0.61 | 0.54 (0.47, 0.6) | 0.26 |
| | SBRT vs. Curative | 0.47 (0.1, 2.21) | 0.34 | | | |
| Treatment Group | chemo RT vs. RT Alone | 1.64 (0.67, 4.06) | | 0.28 | 0.55 (0.46, 0.64) | 0.26 |
| Stage II or III at Diagnosis | Yes vs. No | 1.07 (0.43, 2.68) | | 0.89 | 0.51 (0.42, 0.59) | 0.89 |
| Smoking* | | — | — | — | — | — |
| Tumor Type | Squamous vs. | 4.39 (0.96, 19.98) | | 0.056 | 0.59 (0.52, 0.65) | 0.008 |
| Median Household Income* | | — | — | — | — | — |

TABLE 5-continued

Predictive Ability Of Biomarkers For Local Tumor Control Failure (Univariate)

| | | Odds Ratio | | | Area Under the Curve | |
|---|---|---|---|---|---|---|
| Parameter | Level | OR (95% CI) | Comparison p-value | Overall p-value | AUC (95% CI) | p-value |
| Biomarkers | | | | | | |
| ALDH1A1 Int | | 1.48 (0.88, 2.49) | | 0.14 | 0.57 (0.46, 0.67) | 0.21 |
| ALDH1A1 Prop | | 1.27 (0.94, 1.73) | | 0.12 | 0.57 (0.47, 0.67) | 0.18 |
| ALDH1A1 Tot | | 1.19 (0.97, 1.45) | | 0.09 | 0.57 (0.47, 0.68) | 0.18 |
| Beta_Cat Int | | 0.65 (0.36, 1.2) | | 0.17 | 0.57 (0.46, 0.69) | 0.20 |
| Beta_Cat Prop | | 0.85 (0.58, 1.26) | | 0.42 | 0.56 (0.45, 0.67) | 0.30 |
| Beta_Cat Tot | | 0.85 (0.66, 1.11) | | 0.24 | 0.59 (0.47, 0.71) | 0.13 |
| CD44 Int | | 1.94 (1.08, 3.51) | | 0.027 | 0.62 (0.52, 0.72) | 0.019 |
| CD44 Prop | | 1.7 (1.11, 2.6) | | 0.014 | 0.65 (0.55, 0.76) | 0.003 |
| CD44 Tot | | 1.44 (1.08, 1.92) | | 0.012 | 0.66 (0.55, 0.76) | 0.004 |
| CD68 Int | | 1.93 (0.83, 4.49) | | 0.13 | 0.56 (0.47, 0.64) | 0.18 |
| CD68 Prop | | 1.16 (0.67, 2) | | 0.61 | 0.55 (0.47, 0.63) | 0.22 |
| CD68 Tot | | 1.16 (0.82, 1.66) | | 0.40 | 0.55 (0.47, 0.63) | 0.23 |
| HA Int | | 1.03 (0.65, 1.62) | | 0.91 | 0.51 (0.4, 0.63) | 0.80 |
| HA Prop | | 0.96 (0.74, 1.26) | | 0.79 | 0.5 (0.39 0.61) | 0.97 |
| HA Tot | | 0.99 (0.83, 1.18) | | 0.89 | 0.5 (0.39, 0.61) | 0.96 |
| MFG_E8 Int | | 0.73 (0.47, 1.14) | | 0.17 | 0.58 (0.47, 0.7) | 0.17 |
| MFG_E8 Prop | | 0.77 (0.62, 0.97) | | 0.029 | 0.64 (0.52, 0.75) | 0.019 |
| MFG_E8 Tot | | 0.85 (0.73, 1) | | 0.046 | 0.63 (0.52, 0.74) | 0.023 |
| MMP_9 Int | | 1.39 (0.73, 2.67) | | 0.32 | 0.56 (0.46, 0.66) | 0.23 |
| MMP_9 Prop | | 1.26 (0.69, 2.3) | | 0.46 | 0.57 (0.5, 0.65) | 0.06 |
| MMP_9 Tot | | 1.2 (0.83, 1.73) | | 0.33 | 0.59 (0.49, 0.7) | 0.07 |
| VIM Int | | 1.15 (0.73, 1.81) | | 0.56 | 0.53 (0.43, 0.62) | 0.58 |
| VIM Prop | | 1.07 (0.76, 1.49) | | 0.71 | 0.52 (0.43, 0.61) | 0.65 |
| VIM Tot | | 1.05 (0.86, 1.28) | | 0.63 | 0.52 (0.43, 0.61) | 0.65 |

Figure 10:
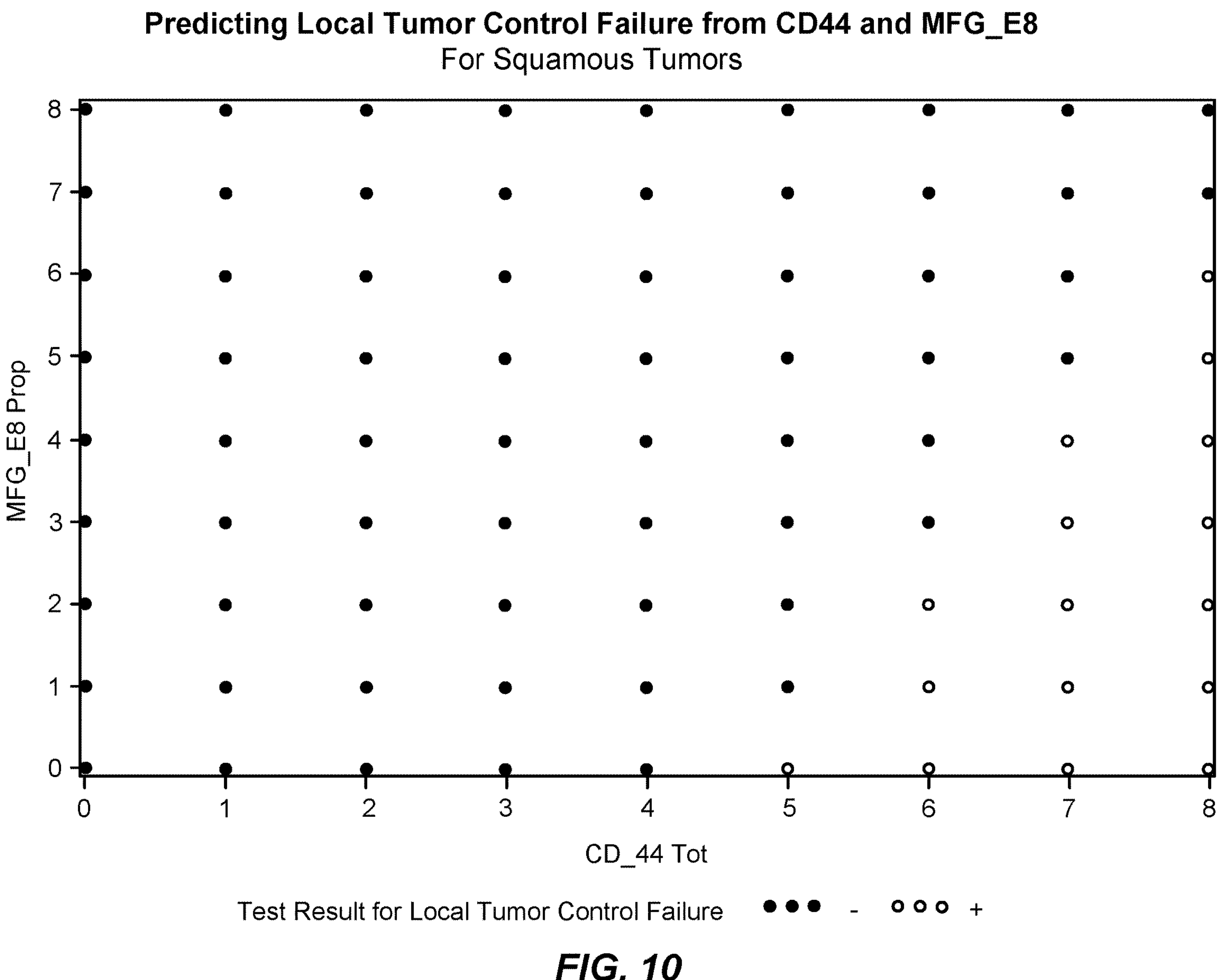
FIG. 10 shows the values of CD44 (Tot) and MFG_E8 (Prop) that correspond to a positive and negative test result for predicting local tumor control failure for squamous tumors, as described in the Examples.
Figure 11:
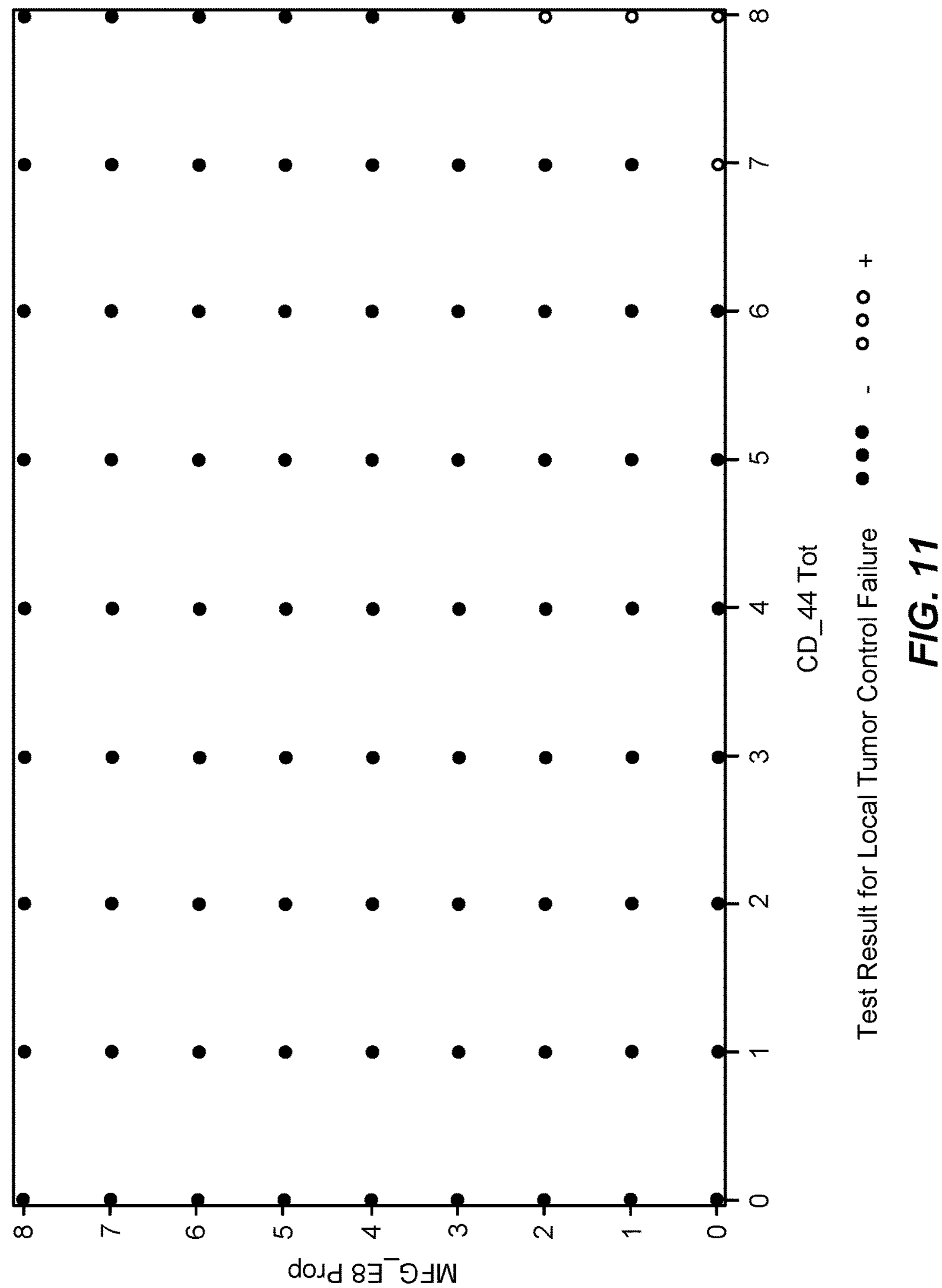
FIG. 11 shows the values of CD44 (Tot) and MFG_E8 (Prop) that correspond to a positive and negative test result for predicting local tumor control failure for adenocarcinoma tumors, as described in the Examples.

We then chose a probability cut point on this ROC curve that exhibited both high sensitivity and specificity, to act as a "test" for local tumor control failure. We required that both sensitivity and specificity be at least 0.5, and gave more importance to high sensitivity by up-weighting it. This resulted in a probability cut point of 21%, which corresponded to a sensitivity of 82% and a specificity of 55%. The values of CD44 Tot and MFG_E8 Prop that correspond to a positive and negative test using this probability cut point, for each tumor type, can be seen in FIGS. 10 and 11.

Subgroup Analyses for Stage II and III Patients

As a sensitivity analysis, univariate survival estimates for patient characteristics and biomarker levels were also recalculated among stage II and III patients only (results not shown). In this analysis, the covariate that achieved statistical significance was race (p-value=0.018).

This Example demonstrates that, among 133 deceased lung cancer patients, CD68 expression was associated with increased risk of death, while MMP_9 expression was associated with decreased risk of death. Patient characteristics most predictive of survival outcomes were CD68 and race. CD44, MFG_E8, and tumor type were predictive of local tumor control failure.

It is understood that the examples and embodiments described herein are for illustrative purposes only and that various modifications or changes in light thereof will be suggested to persons skilled in the art and are to be included within the spirit and purview of this application and scope of the appended claims. All publications, patents, patent applications, and sequence accession numbers cited herein are hereby incorporated by reference in their entirety for all purposes.

What is claimed is:

1. A method for treating a tumor in a subject in need thereof, comprising:

(a) determining an expression level of biomarkers CD44 and CD68 in a tumor sample from the subject;

(b) comparing the expression level of biomarkers CD44 and CD68 to an expression level in a normal tissue sample; and treating the tumor if the expression levels of biomarkers CD44 and CD68 are increased compared to the expression level in the normal tissue sample, wherein the treatment comprises administering ionizing radiation to the tumor.

2. The method of claim 1, wherein the treatment further comprises contacting the tumor with a radiosensitizer.

3. The method of claim 1, wherein the treatment further comprises administering a compound that inhibits TGF-beta signaling to the subject.

4. The method of claim 3, wherein the compound that inhibits TGF-beta signaling is an antibody.

5. The method of claim 3, wherein the compound that inhibits TGF-beta signaling is a peptide.

6. The method of claim 3, wherein the compound that inhibits TGF-beta signaling is a small molecule that neutralizes or inhibits TGF-beta function.

7. The method of claim 1, wherein the tumor sample is a biopsy comprising tumor cells.

8. The method of claim 1, wherein the biomarker is a protein.

9. The method of claim 1, wherein the expression levels of CD44 and CD68 are determined by detecting the expression levels of the proteins.

10. The method of claim 9, wherein the detecting is selected from the group consisting of immunohistochemistry, ELISA, Western analysis, HPLC, proteomics, or polypeptide microarrays.

11. The method of claim 9, comprising contacting the tumor sample from the subject with antibodies that bind to the biomarkers CD44 and CD68.

12. The method of claim 1, wherein the normal tissue sample comprises non-tumor cells from the same tissue type as the tumor.

13. The method of claim 1, wherein the expression level of the biomarkers is ranked or weighted.

14. The method of claim 1, further comprising determining the expression level of MMP9, ALDH1A1, Vimentin, hyalurnan, beta-catenin, and MFG-E8.

15. The method of claim 1, wherein the treatment comprises increasing the effective dose of ionizing radiation administered to the tumor if the expression levels of biomarkers CD44 and CD68 are increased compared to the expression level of the same biomarkers in the normal tissue sample.

16. The method of claim 15, wherein the effective dose is increased by increasing the amount of ionizing radiation administered to the tumor and/or contacting the tumor with a radiosensitizer.

17. A method of treating a subject having a tumor, the method comprising:

administering ionizing radiation to a tumor in a subject that has been selected as having expression levels of biomarkers CD44 and CD68 in a tumor sample that are increased relative to an expression level in a normal tissue sample;

thereby treating the tumor in the subject.

* * * * *

SEQUENCE LISTING

<160> NUMBER OF SEQ ID NOS: 14

<210> SEQ ID NO 1
<211> LENGTH: 742
<212> TYPE: PRT
<213> ORGANISM: Homo sapiens
<220> FEATURE:
<223> OTHER INFORMATION: CD44 antigen isoform 1 precursor, hematopoeitic cell E- and L-selectin ligand (HCELL), chondroitin sulfate proteoglycan 8 (CSPG8), GP90 lymphocyte homing/adhesion receptor (LHR), extracellular matrix receptor III (ECMR-III), Hermes antigen

<400> SEQUENCE: 1

```
Met Asp Lys Phe Trp Trp His Ala Ala Trp Gly Leu Cys Leu Val Pro
1               5                   10                  15

Leu Ser Leu Ala Gln Ile Asp Leu Asn Ile Thr Cys Arg Phe Ala Gly
            20                  25                  30

Val Phe His Val Glu Lys Asn Gly Arg Tyr Ser Ile Ser Arg Thr Glu
        35                  40                  45

Ala Ala Asp Leu Cys Lys Ala Phe Asn Ser Thr Leu Pro Thr Met Ala
    50                  55                  60

Gln Met Glu Lys Ala Leu Ser Ile Gly Phe Glu Thr Cys Arg Tyr Gly
65                  70                  75                  80

Phe Ile Glu Gly His Val Val Ile Pro Arg Ile His Pro Asn Ser Ile
                85                  90                  95

Cys Ala Ala Asn Asn Thr Gly Val Tyr Ile Leu Thr Ser Asn Thr Ser
            100                 105                 110

Gln Tyr Asp Thr Tyr Cys Phe Asn Ala Ser Ala Pro Pro Glu Glu Asp
        115                 120                 125

Cys Thr Ser Val Thr Asp Leu Pro Asn Ala Phe Asp Gly Pro Ile Thr
    130                 135                 140

Ile Thr Ile Val Asn Arg Asp Gly Thr Arg Tyr Val Gln Lys Gly Glu
145                 150                 155                 160

Tyr Arg Thr Asn Pro Glu Asp Ile Tyr Pro Ser Asn Pro Thr Asp Asp
                165                 170                 175

Asp Val Ser Ser Gly Ser Ser Ser Glu Arg Ser Ser Thr Ser Gly Gly
            180                 185                 190

Tyr Ile Phe Tyr Thr Phe Ser Thr Val His Pro Ile Pro Asp Glu Asp
        195                 200                 205

Ser Pro Trp Ile Thr Asp Ser Thr Asp Arg Ile Pro Ala Thr Thr Leu
    210                 215                 220

Met Ser Thr Ser Ala Thr Ala Thr Glu Thr Ala Thr Lys Arg Gln Glu
225                 230                 235                 240

Thr Trp Asp Trp Phe Ser Trp Leu Phe Leu Pro Ser Glu Ser Lys Asn
                245                 250                 255

His Leu His Thr Thr Thr Gln Met Ala Gly Thr Ser Ser Asn Thr Ile
            260                 265                 270

Ser Ala Gly Trp Glu Pro Asn Glu Glu Asn Glu Asp Glu Arg Asp Arg
        275                 280                 285

His Leu Ser Phe Ser Gly Ser Gly Ile Asp Asp Asp Glu Asp Phe Ile
    290                 295                 300

Ser Ser Thr Ile Ser Thr Thr Pro Arg Ala Phe Asp His Thr Lys Gln
305                 310                 315                 320

Asn Gln Asp Trp Thr Gln Trp Asn Pro Ser His Ser Asn Pro Glu Val
                325                 330                 335
```

```
Leu Leu Gln Thr Thr Thr Arg Met Thr Asp Val Asp Arg Asn Gly Thr
            340                 345                 350

Thr Ala Tyr Glu Gly Asn Trp Asn Pro Glu Ala His Pro Pro Leu Ile
        355                 360                 365

His His Glu His His Glu Glu Glu Thr Pro His Ser Thr Ser Thr
    370                 375                 380

Ile Gln Ala Thr Pro Ser Ser Thr Thr Glu Glu Thr Ala Thr Gln Lys
385                 390                 395                 400

Glu Gln Trp Phe Gly Asn Arg Trp His Glu Gly Tyr Arg Gln Thr Pro
                405                 410                 415

Lys Glu Asp Ser His Ser Thr Thr Gly Thr Ala Ala Ala Ser Ala His
            420                 425                 430

Thr Ser His Pro Met Gln Gly Arg Thr Thr Pro Ser Pro Glu Asp Ser
        435                 440                 445

Ser Trp Thr Asp Phe Phe Asn Pro Ile Ser His Pro Met Gly Arg Gly
    450                 455                 460

His Gln Ala Gly Arg Arg Met Asp Met Asp Ser Ser His Ser Ile Thr
465                 470                 475                 480

Leu Gln Pro Thr Ala Asn Pro Asn Thr Gly Leu Val Glu Asp Leu Asp
                485                 490                 495

Arg Thr Gly Pro Leu Ser Met Thr Thr Gln Gln Ser Asn Ser Gln Ser
            500                 505                 510

Phe Ser Thr Ser His Glu Gly Leu Glu Glu Asp Lys Asp His Pro Thr
        515                 520                 525

Thr Ser Thr Leu Thr Ser Ser Asn Arg Asn Asp Val Thr Gly Gly Arg
    530                 535                 540

Arg Asp Pro Asn His Ser Glu Gly Ser Thr Thr Leu Leu Glu Gly Tyr
545                 550                 555                 560

Thr Ser His Tyr Pro His Thr Lys Glu Ser Arg Thr Phe Ile Pro Val
                565                 570                 575

Thr Ser Ala Lys Thr Gly Ser Phe Gly Val Thr Ala Val Thr Val Gly
            580                 585                 590

Asp Ser Asn Ser Asn Val Asn Arg Ser Leu Ser Gly Asp Gln Asp Thr
        595                 600                 605

Phe His Pro Ser Gly Gly Ser His Thr Thr His Gly Ser Glu Ser Asp
    610                 615                 620

Gly His Ser His Gly Ser Gln Glu Gly Gly Ala Asn Thr Thr Ser Gly
625                 630                 635                 640

Pro Ile Arg Thr Pro Gln Ile Pro Glu Trp Leu Ile Ile Leu Ala Ser
                645                 650                 655

Leu Leu Ala Leu Ala Leu Ile Leu Ala Val Cys Ile Ala Val Asn Ser
            660                 665                 670

Arg Arg Arg Cys Gly Gln Lys Lys Lys Leu Val Ile Asn Ser Gly Asn
        675                 680                 685

Gly Ala Val Glu Asp Arg Lys Pro Ser Gly Leu Asn Gly Glu Ala Ser
    690                 695                 700

Lys Ser Gln Glu Met Val His Leu Val Asn Lys Glu Ser Ser Glu Thr
705                 710                 715                 720

Pro Asp Gln Phe Met Thr Ala Asp Glu Thr Arg Asn Leu Gln Asn Val
                725                 730                 735

Asp Met Lys Ile Gly Val
            740
```

<210> SEQ ID NO 2
<211> LENGTH: 5748
<212> TYPE: DNA
<213> ORGANISM: Homo sapiens
<220> FEATURE:
<223> OTHER INFORMATION: CD44 antigen transcript variant 1, hematopoeitic cell E- and L-selectin ligand (HCELL), chondroitin sulfate proteoglycan 8 (CSPG8), GP90 lymphocyte homing/adhesion receptor (LHR), extracellular matrix receptor III (ECMR-III), Hermes antigen

<400> SEQUENCE: 2

```
gagaagaaag ccagtgcgtc tctgggcgca ggggccagtg ggctcggag gcacaggcac      60

cccgcgacac tccaggttcc ccgacccacg tccctggcag ccccgattat ttacagcctc    120

agcagagcac ggggcggggg cagaggggcc cgcccgggag ggctgctact tcttaaaacc    180

tctgcgggct gcttagtcac agccccccct gcttgggtgt gtccttcgct cgctccctcc    240

ctccgtctta ggtcactgtt ttcaacctcg aataaaaact gcagccaact tccgaggcag    300

cctcattgcc cagcggaccc cagcctctgc caggttcggt ccgccatcct cgtcccgtcc    360

tccgccggcc cctgccccgc gcccagggat cctccagctc ctttcgcccg cgccctccgt    420

tcgctccgga caccatggac aagttttggt ggcacgcagc ctggggactc tgcctcgtgc    480

cgctgagcct ggcgcagatc gatttgaata taacctgccg ctttgcaggt gtattccacg    540

tggagaaaaa tggtcgctac agcatctctc ggacggaggc cgctgacctc tgcaaggctt    600

tcaatagcac cttgcccaca atggcccaga tggagaaagc tctgagcatc ggatttgaga    660

cctgcaggta tgggttcata gaagggcacg tggtgattcc ccggatccac cccaactcca    720

tctgtgcagc aaacaacaca ggggtgtaca tcctcacatc caacacctcc cagtatgaca    780

catattgctt caatgcttca gctccacctg aagaagattg tacatcagtc acagacctgc    840

ccaatgcctt tgatggacca attaccataa ctattgttaa ccgtgatggc acccgctatg    900

tccagaaagg agaatacaga acgaatcctg aagacatcta ccccagcaac cctactgatg    960

atgacgtgag cagcggctcc tccagtgaaa ggagcagcac ttcaggaggt tacatctttt   1020

acaccttttc tactgtacac cccatcccag acgaagacag tccctggatc accgacagca   1080

cagacagaat ccctgctacc actttgatga gcactagtgc tacagcaact gagacagcaa   1140

ccaagaggca agaaacctgg gattggtttt catggttgtt tctaccatca gagtcaaaga   1200

atcatcttca cacaacaaca caaatggctg gtacgtcttc aaataccatc tcagcaggct   1260

gggagccaaa tgaagaaaat gaagatgaaa gagacagaca cctcagtttt tctggatcag   1320

gcattgatga tgatgaagat tttatctcca gcaccatttc aaccacacca cgggcttttg   1380

accacacaaa acagaaccag gactggaccc agtggaaccc aagccattca aatccggaag   1440

tgctacttca gacaaccaca aggatgactg atgtagacag aaatggcacc actgcttatg   1500

aaggaaactg gaacccagaa gcacaccctc ccctcattca ccatgagcat catgaggaag   1560

aagagacccc acattctaca agcacaatcc aggcaactcc tagtagtaca acggaagaaa   1620

cagctaccca gaaggaacag tggtttggca acagatggca tgagggatat cgccaaacac   1680

ccaaagaaga ctcccattcg acaacaggga cagctgcagc ctcagctcat accagccatc   1740

caatgcaagg aaggacaaca ccaagcccag aggacagttc ctggactgat ttcttcaacc   1800

caatctcaca ccccatggga cgaggtcatc aagcaggaag aaggatggat atggactcca   1860

gtcatagtat aacgcttcag cctactgcaa atccaaacac aggtttggtg gaagatttgg   1920

acaggacagg acctctttca atgacaacgc agcagagtaa ttctcagagc ttctctacat   1980
```

-continued

```
cacatgaagg cttggaagaa gataaagacc atccaacaac ttctactctg acatcaagca   2040
ataggaatga tgtcacaggt ggaagaagag acccaaatca ttctgaaggc tcaactactt   2100
tactggaagg ttatacctct cattacccac acacgaagga aagcaggacc ttcatcccag   2160
tgacctcagc taagactggg tcctttggag ttactgcagt tactgttgga gattccaact   2220
ctaatgtcaa tcgttcctta tcaggagacc aagacacatt ccaccccagt ggggggtccc   2280
ataccactca tggatctgaa tcagatggac actcacatgg gagtcaagaa ggtggagcaa   2340
acacaacctc tggtcctata aggacacccc aaattccaga atggctgatc atcttggcat   2400
ccctcttggc cttggctttg attcttgcag tttgcattgc agtcaacagt cgaagaaggt   2460
gtgggcagaa gaaaaagcta gtgatcaaca gtggcaatgg agctgtggag gacagaaagc   2520
caagtggact caacggagag gccagcaagt ctcaggaaat ggtgcatttg gtgaacaagg   2580
agtcgtcaga aactccagac cagtttatga cagctgatga gacaaggaac ctgcagaatg   2640
tggacatgaa gattggggtg taacacctac accattatct tggaaagaaa caaccgttgg   2700
aaacataacc attacaggga gctgggacac ttaacagatg caatgtgcta ctgattgttt   2760
cattgcgaat ctttttttagc ataaaatttt ctactctttt tgtttttttgt gttttgttct   2820
ttaaagtcag gtccaatttg taaaaacagc attgctttct gaaattaggg cccaattaat   2880
aatcagcaag aatttgatcg ttccagttcc cacttggagg cctttcatcc ctcgggtgtg   2940
ctatggatgg cttctaacaa aaactacaca tatgtattcc tgatcgccaa cctttccccc   3000
accagctaag gacatttccc agggttaata gggcctggtc cctgggagga aatttgaatg   3060
ggtccatttt gcccttccat agcctaatcc ctgggcattg ctttccactg aggttggggg   3120
ttggggtgta ctagttacac atcttcaaca gaccccctct agaaattttt cagatgcttc   3180
tgggagacac ccaaagggtg aagctattta tctgtagtaa actatttatc tgtgtttttg   3240
aaatattaaa ccctggatca gtcctttgat cagtataatt ttttaaagtt actttgtcag   3300
aggcacaaaa gggtttaaac tgattcataa taaatatctg tacttcttcg atcttcacct   3360
tttgtgctgt gattcttcag tttctaaacc agcactgtct gggtccctac aatgtatcag   3420
gaagagctga gaatggtaag gagactcttc taagtcttca tctcagagac cctgagttcc   3480
cactcagacc cactcagcca aatctcatgg aagaccaagg agggcagcac tgtttttgtt   3540
ttttgttttt tgtttttttt ttttgacact gtccaaaggt tttccatcct gtcctggaat   3600
cagagttgga agctgaggag cttcagcctc ttttatggtt taatggccac ctgttctctc   3660
ctgtgaaagg ctttgcaaag tcacattaag tttgcatgac ctgttatccc tggggcccta   3720
tttcatagag gctggcccta ttagtgattt ccaaaaacaa tatggaagtg ccttttgatg   3780
tcttacaata agagaagaag ccaatggaaa tgaaagagat tggcaaaggg gaaggatgat   3840
gccatgtaga tcctgtttga catttttatg gctgtatttg taaacttaaa cacaccagtg   3900
tctgttcttg atgcagttgc tatttaggat gagttaagtg cctggggagt ccctcaaaag   3960
gttaaaggga ttcccatcat tggaatctta tcaccagata ggcaagttta tgaccaaaca   4020
agagagtact ggctttatcc tctaacctca tattttctcc cacttggcaa gtcctttgtg   4080
gcatttattc atcagtcagg gtgtccgatt ggtcctagaa cttccaaagg ctgcttgtca   4140
tagaagccat tgcatctata aagcaacggc tcctgttaaa tggtatctcc tttctgaggc   4200
tcctactaaa agtcatttgt tacctaaact tatgtgctta acaggcaatg cttctcagac   4260
cacaaagcag aaagaagaag aaaagctcct gactaaatca gggctgggct tagacagagt   4320
tgatctgtag aatatcttta aaggagagat gtcaactttc tgcactattc ccagcctctg   4380
```

```
ctcctccctg tctaccctct cccctccctc tctccctcca cttcacccca caatcttgaa   4440
aaacttcctt tctcttctgt gaacatcatt ggccagatcc attttcagtg gtctggattt   4500
ctttttattt tcttttcaac ttgaaagaaa ctggacatta ggccactatg tgttgttact   4560
gccactagtg ttcaagtgcc tcttgttttc ccagagattt cctgggtctg ccagaggccc   4620
agacaggctc actcaagctc tttaactgaa aagcaacaag ccactccagg acaaggttca   4680
aaatggttac aacagcctct acctgtcgcc ccagggagaa aggggtagtg atacaagtct   4740
catagccaga gatggttttc cactccttct agatattccc aaaaagaggc tgagacagga   4800
ggttattttc aattttattt tggaattaaa tactttttc cctttattac tgttgtagtc    4860
cctcacttgg atatacctct gttttcacga tagaaataag ggaggtctag agcttctatt   4920
ccttggccat tgtcaacgga gagctggcca agtcttcaca aacccttgca acattgcctg   4980
aagtttatgg aataagatgt attctcactc ccttgatctc aagggcgtaa ctctggaagc   5040
acagcttgac tacacgtcat ttttaccaat gattttcagg tgacctgggc taagtcattt   5100
aaactgggtc tttataaaag taaaaggcca acatttaatt attttgcaaa gcaacctaag   5160
agctaaagat gtaatttttc ttgcaattgt aaatcttttg tgtctcctga agacttccct   5220
taaaattagc tctgagtgaa aaatcaaaag agacaaaaga catcttcgaa tccatatttc   5280
aagcctggta gaattggctt ttctagcaga acctttccaa aagttttata ttgagattca   5340
taacaacacc aagaattgat tttgtagcca acattcattc aatactgtta tatcagagga   5400
gtaggagaga ggaaacattt gacttatctg gaaaagcaaa atgtacttaa gaataagaat   5460
aacatggtcc attcaccttt atgttataga tatgtctttg tgtaaatcat ttgttttgag   5520
ttttcaaaga atagcccatt gttcattctt gtgctgtaca atgaccactg ttattgttac   5580
tttgactttt cagagcacac ccttcctctg gtttttgtat atttattgat ggatcaataa   5640
taatgaggaa agcatgatat gtatattgct gagttgaaag cacttattgg aaaatattaa   5700
aaggctaaca ttaaaagact aaaggaaaca gaaaaaaaaa aaaaaaaa                5748
```

```
<210> SEQ ID NO 3
<211> LENGTH: 707
<212> TYPE: PRT
<213> ORGANISM: Homo sapiens
<220> FEATURE:
<223> OTHER INFORMATION: matrix metalloproteinase 9 (MMP9, MMP-9)

<400> SEQUENCE: 3

Met Ser Leu Trp Gln Pro Leu Val Leu Val Leu Leu Val Leu Gly Cys
1               5                   10                  15

Cys Phe Ala Ala Pro Arg Gln Arg Gln Ser Thr Leu Val Leu Phe Pro
            20                  25                  30

Gly Asp Leu Arg Thr Asn Leu Thr Asp Arg Gln Leu Ala Glu Glu Tyr
        35                  40                  45

Leu Tyr Arg Tyr Gly Tyr Thr Arg Val Ala Glu Met Arg Gly Glu Ser
    50                  55                  60

Lys Ser Leu Gly Pro Ala Leu Leu Leu Leu Gln Lys Gln Leu Ser Leu
65                  70                  75                  80

Pro Glu Thr Gly Glu Leu Asp Ser Ala Thr Leu Lys Ala Met Arg Thr
                85                  90                  95

Pro Arg Cys Gly Val Pro Asp Leu Gly Arg Phe Gln Thr Phe Glu Gly
            100                 105                 110

Asp Leu Lys Trp His His His Asn Ile Thr Tyr Trp Ile Gln Asn Tyr
```

```
        115                 120                 125

Ser Glu Asp Leu Pro Arg Ala Val Ile Asp Asp Ala Phe Ala Arg Ala
    130                 135                 140

Phe Ala Leu Trp Ser Ala Val Thr Pro Leu Thr Phe Thr Arg Val Tyr
145                 150                 155                 160

Ser Arg Asp Ala Asp Ile Val Ile Gln Phe Gly Val Ala Glu His Gly
                165                 170                 175

Asp Gly Tyr Pro Phe Asp Gly Lys Asp Gly Leu Leu Ala His Ala Phe
            180                 185                 190

Pro Pro Gly Pro Gly Ile Gln Gly Asp Ala His Phe Asp Asp Asp Glu
        195                 200                 205

Leu Trp Ser Leu Gly Lys Gly Val Val Val Pro Thr Arg Phe Gly Asn
    210                 215                 220

Ala Asp Gly Ala Ala Cys His Phe Pro Phe Ile Phe Glu Gly Arg Ser
225                 230                 235                 240

Tyr Ser Ala Cys Thr Thr Asp Gly Arg Ser Asp Gly Leu Pro Trp Cys
                245                 250                 255

Ser Thr Thr Ala Asn Tyr Asp Thr Asp Asp Arg Phe Gly Phe Cys Pro
            260                 265                 270

Ser Glu Arg Leu Tyr Thr Arg Asp Gly Asn Ala Asp Gly Lys Pro Cys
        275                 280                 285

Gln Phe Pro Phe Ile Phe Gln Gly Gln Ser Tyr Ser Ala Cys Thr Thr
    290                 295                 300

Asp Gly Arg Ser Asp Gly Tyr Arg Trp Cys Ala Thr Thr Ala Asn Tyr
305                 310                 315                 320

Asp Arg Asp Lys Leu Phe Gly Phe Cys Pro Thr Arg Ala Asp Ser Thr
                325                 330                 335

Val Met Gly Gly Asn Ser Ala Gly Glu Leu Cys Val Phe Pro Phe Thr
            340                 345                 350

Phe Leu Gly Lys Glu Tyr Ser Thr Cys Thr Ser Glu Gly Arg Gly Asp
        355                 360                 365

Gly Arg Leu Trp Cys Ala Thr Thr Ser Asn Phe Asp Ser Asp Lys Lys
    370                 375                 380

Trp Gly Phe Cys Pro Asp Gln Gly Tyr Ser Leu Phe Leu Val Ala Ala
385                 390                 395                 400

His Glu Phe Gly His Ala Leu Gly Leu Asp His Ser Ser Val Pro Glu
                405                 410                 415

Ala Leu Met Tyr Pro Met Tyr Arg Phe Thr Glu Gly Pro Pro Leu His
            420                 425                 430

Lys Asp Asp Val Asn Gly Ile Arg His Leu Tyr Gly Pro Arg Pro Glu
        435                 440                 445

Pro Glu Pro Arg Pro Pro Thr Thr Thr Thr Pro Gln Pro Thr Ala Pro
    450                 455                 460

Pro Thr Val Cys Pro Thr Gly Pro Pro Thr Val His Pro Ser Glu Arg
465                 470                 475                 480

Pro Thr Ala Gly Pro Thr Gly Pro Pro Ser Ala Gly Pro Thr Gly Pro
                485                 490                 495

Pro Thr Ala Gly Pro Ser Thr Ala Thr Thr Val Pro Leu Ser Pro Val
            500                 505                 510

Asp Asp Ala Cys Asn Val Asn Ile Phe Asp Ala Ile Ala Glu Ile Gly
        515                 520                 525

Asn Gln Leu Tyr Leu Phe Lys Asp Gly Lys Tyr Trp Arg Phe Ser Glu
    530                 535                 540
```

```
Gly Arg Gly Ser Arg Pro Gln Gly Pro Phe Leu Ile Ala Asp Lys Trp
545                 550                 555                 560

Pro Ala Leu Pro Arg Lys Leu Asp Ser Val Phe Glu Glu Pro Leu Ser
                565                 570                 575

Lys Lys Leu Phe Phe Phe Ser Gly Arg Gln Val Trp Val Tyr Thr Gly
            580                 585                 590

Ala Ser Val Leu Gly Pro Arg Arg Leu Asp Lys Leu Gly Leu Gly Ala
        595                 600                 605

Asp Val Ala Gln Val Thr Gly Ala Leu Arg Ser Gly Arg Gly Lys Met
    610                 615                 620

Leu Leu Phe Ser Gly Arg Arg Leu Trp Arg Phe Asp Val Lys Ala Gln
625                 630                 635                 640

Met Val Asp Pro Arg Ser Ala Ser Glu Val Asp Arg Met Phe Pro Gly
                645                 650                 655

Val Pro Leu Asp Thr His Asp Val Phe Gln Tyr Arg Glu Lys Ala Tyr
            660                 665                 670

Phe Cys Gln Asp Arg Phe Tyr Trp Arg Val Ser Ser Arg Ser Glu Leu
        675                 680                 685

Asn Gln Val Asp Gln Val Gly Tyr Val Thr Tyr Asp Ile Leu Gln Cys
    690                 695                 700

Pro Glu Asp
705
```

<210> SEQ ID NO 4
<211> LENGTH: 4506
<212> TYPE: DNA
<213> ORGANISM: Homo sapiens
<220> FEATURE:
<223> OTHER INFORMATION: matrix metalloproteinase 9 (MMP9, MMP-9)

<400> SEQUENCE: 4

```
aagcttcaga gccaggcagt tctgggcttg aacactagtt ctgtggatta actcgctctg     60

tgatcacagg caaattcctt aactctctga gccttagttt ccccctctga aaacaggagg    120

gatactcatt aaacttacct tacaggtggt gaggatgaaa cgagaggctt atagagaact    180

tattacggtg cttgacacag taaatctcaa aaaatgcatt attattatta tggttcagag    240

gtaaagtgac ttgcccaagg tcacatagct ggaaaatgca gagccgggat ggaaatccag    300

gacttcgtga cgcaaagcag atgttcattg gttagtgaac tttagaactt caacttttct    360

gtaaaggaag ttaattatct ccatctcaca gtctcattta ttagataagc atataaaatg    420

cctggcacat agtaggccct ttaaatacag cttattgggc cgggcgccat gctcatgccc    480

gtaatcctag cactttggga ggccaggtgg gcagatcact tgagtcagaa gttcgaaacc    540

agcctggtca acgtagtgaa accccatctc tactaaaaat acaaaaaatt tagccaggcg    600

tggtggcgca cctataatac cagctactcg ggaggctgag gcaggagaat tgcttgaacc    660

cgggaggcag atgttgcagt gagccgagat cacgccactg cactccagcc tgggtgacag    720

agtgatacta cccccccaa aaataaaata aaataaataa atacaacttt ttgagttgtt     780

agcaggtttt tcccaaatag ggctttgaag aaggtgaata tagaccctgc ccgatgccgg    840

ctggctagga agaaaggagt gagggaggct gctggtgtgg gaggcttggg agggaggctt    900

ggcataagtg tgataattgg gcctggagat ttggctgcat ggaggcaggg ctggaggaac    960

taagggctcc tatagattat ttccccatat cctgccgcaa tttgcagttg aagaatccta   1020

agctgagaaa ggggaggcat ttactccagg ttacactgca gcttagagcc caataacctg   1080
```

```
gtttggtgat tccaagttag aatcatggtc ttttggcagg gtctcgctct gttgcccagg   1140
ctggagtgca gtgacataat catggctcac tgtatccttg accttctttc tgggctcaag   1200
caatcctccc acctcggcct cccaaagtgc taagattaca ggaatgagcc accatacctg   1260
gccctgaatc ttgggtcttg gccttagtaa ttaaaaccaa tcaccaccat ccgttgcgga   1320
cttacaacct acagtgttct aaacatttta tatgtttgat ctcatttaat cctcacatca   1380
atttagggac aaagagcccc ccaccccccg ttttttttt tacagctgag gaaacacttc   1440
aaagtggtaa gacatttgcc cgaggtcctg aaggaagaga gtaaagccat gtctgctgtt   1500
ttctagaggc tgctactgtc ccctttactg ccctgaagat tcagcctgcg gaagacaggg   1560
ggttgcccca gtggaattcc ccagccttgc ctagcagagc ccattccttc cgcccccaga   1620
tgaagcaggg agaggaagct gagtcaaaga aggctgtcag ggagggaaaa agaggacaga   1680
gcctggagtg tggggagggg tttggggagg atatctgacc tgggaggggg tgttgcaaaa   1740
ggccaaggat gggccagggg gatcattagt ttcagaaaga agtctcaggg agtcttccat   1800
cactttccct tggctgacca ctggaggctt tcagaccaag ggatggggga tccctccagc   1860
ttcatccccc tccctccctt tcatacagtt cccacaagct ctgcagtttg caaaacccta   1920
cccctcccct gagggcctgc ggtttcctgc gggtctgggg tcttgcctga cttggcagtg   1980
gagactgcgg gcagtggaga gaggaggagg tggtgtaagc cctttctcat gctggtgctg   2040
ccacacacac acacacacac acacacacac acacacacac acaccctgac ccctgagtca   2100
gcacttgcct gtcaaggagg ggtggggtca caggagcgcc tccttaaagc ccccacaaca   2160
gcagctgcag tcagacacct ctgccctcac catgagcctc tggcagcccc tggtcctggt   2220
gctcctggtg ctgggctgct gctttgctgc cccccagacag cgccagtcca cccttgtgct   2280
cttccctgga gacctgagaa ccaatctcac cgacaggcag ctggcagagg aatacctgta   2340
ccgctatggt tacactcggg tggcagagat gcgtggagag tcgaaatctc tggggcctgc   2400
gctgctgctt ctccagaagc aactgtccct gcccgagacc ggtgagctgg atagcgccac   2460
gctgaaggcc atgcgaaccc cacggtgcgg ggtcccagac ctgggcagat tccaaacctt   2520
tgagggcgac ctcaagtggc accaccacaa catcacctat tggatccaaa actactcgga   2580
agacttgccg cgggcggtga ttgacgacgc ctttgcccgc gccttcgcac tgtggagcgc   2640
ggtgacgccg ctcaccttca ctcgcgtgta cagccgggac gcagacatcg tcatccagtt   2700
tggtgtcgcg gagcacggag acgggtatcc cttcgacggg aaggacgggc tcctggcaca   2760
cgcctttcct cctggccccg gcattcaggg agacgcccat ttcgacgatg acgagttgtg   2820
gtccctgggc aagggcgtcg tggttccaac tcggtttgga aacgcagatg gcgcggcctg   2880
ccacttcccc ttcatcttcg agggccgctc ctactctgcc tgcaccaccg acggtcgctc   2940
cgacggcttg ccctggtgca gtaccacggc caactacgac accgacgacc ggtttggctt   3000
ctgccccagc gagagactct acacccggga cggcaatgct gatgggaaac cctgccagtt   3060
tccattcatc ttccaaggcc aatcctactc cgcctgcacc acggacggtc gctccgacgg   3120
ctaccgctgg tgcgccacca ccgccaacta cgaccgggac aagctcttcg gcttctgccc   3180
gacccgagct gactcgacgg tgatgggggg caactcggcg ggggagctgt gcgtcttccc   3240
cttcactttc ctgggtaagg agtactcgac ctgtaccagc gagggccgcg gagatgggcg   3300
cctctggtgc gctaccacct cgaactttga cagcgacaag aagtggggct tctgcccgga   3360
ccaaggatac agtttgttcc tcgtggcggc gcatgagttc ggccacgcgc tgggcttaga   3420
```

-continued

```
tcattcctca gtgccggagg cgctcatgta ccctatgtac cgcttcactg aggggccccc   3480

cttgcataag gacgacgtga atggcatccg gcacctctat ggtcctcgcc ctgaacctga   3540

gccacggcct ccaaccacca ccacaccgca gcccacggct cccccgacgg tctgccccac   3600

cggacccccc actgtccacc cctcagagcg ccccacagct ggccccacag gtccccccte   3660

agctggcccc acaggtcccc ccactgctgg cccttctacg gccactactg tgcctttgag   3720

tccggtggac gatgcctgca acgtgaacat cttcgacgcc atcgcggaga ttgggaacca   3780

gctgtatttg ttcaaggatg ggaagtactg gcgattctct gagggcaggg ggagccggcc   3840

gcagggcccc ttccttatcg ccgacaagtg gcccgcgctg ccccgcaagc tggactcggt   3900

ctttgaggag ccgctctcca agaagctttt cttcttctct gggcgccagg tgtgggtgta   3960

cacaggcgcg tcggtgctgg gcccgaggcg tctggacaag ctgggcctgg gagccgacgt   4020

ggcccaggtg accggggccc tccggagtgg caggggggaag atgctgctgt tcagcgggcg   4080

gcgcctctgg aggttcgacg tgaaggcgca gatggtggat ccccggagcg ccagcgaggt   4140

ggaccggatg ttccccgggg tgcctttgga cacgcacgac gtcttccagt accgagagaa   4200

agcctatttc tgccaggacc gcttctactg gcgcgtgagt tcccggagtg agttgaacca   4260

ggtggaccaa gtgggctacg tgacctatga catcctgcag tgccctgagg actagggctc   4320

ccgtcctgct ttgcagtgcc atgtaaatcc ccactgggac caaccctggg gaaggagcca   4380

gtttgccgga tacaaactgg tattctgttc tggaggaaag ggaggagtgg aggtgggctg   4440

ggccctctct tctcaccttt gtttttgtt ggagtgtttc taataaactt ggattctcta   4500

accttt                                                              4506
```

<210> SEQ ID NO 5
<211> LENGTH: 501
<212> TYPE: PRT
<213> ORGANISM: Homo sapiens
<220> FEATURE:
<223> OTHER INFORMATION: aldehyde dehydrogenase 1 family, member A1 (ALDH1A1)

<400> SEQUENCE: 5

```
Met Ser Ser Ser Gly Thr Pro Asp Leu Pro Val Leu Leu Thr Asp Leu
1               5                   10                  15

Lys Ile Gln Tyr Thr Lys Ile Phe Ile Asn Asn Glu Trp His Asp Ser
            20                  25                  30

Val Ser Gly Lys Lys Phe Pro Val Phe Asn Pro Ala Thr Glu Glu Glu
        35                  40                  45

Leu Cys Gln Val Glu Glu Gly Asp Lys Glu Asp Val Asp Lys Ala Val
    50                  55                  60

Lys Ala Ala Arg Gln Ala Phe Gln Ile Gly Ser Pro Trp Arg Thr Met
65                  70                  75                  80

Asp Ala Ser Glu Arg Gly Arg Leu Leu Tyr Lys Leu Ala Asp Leu Ile
                85                  90                  95

Glu Arg Asp Arg Leu Leu Leu Ala Thr Met Glu Ser Met Asn Gly Gly
            100                 105                 110

Lys Leu Tyr Ser Asn Ala Tyr Leu Asn Asp Leu Ala Gly Cys Ile Lys
        115                 120                 125

Thr Leu Arg Tyr Cys Ala Gly Trp Ala Asp Lys Ile Gln Gly Arg Thr
    130                 135                 140

Ile Pro Ile Asp Gly Asn Phe Phe Thr Tyr Thr Arg His Glu Pro Ile
145                 150                 155                 160
```

```
Gly Val Cys Gly Gln Ile Ile Pro Trp Asn Phe Pro Leu Val Met Leu
                165                 170                 175

Ile Trp Lys Ile Gly Pro Ala Leu Ser Cys Gly Asn Thr Val Val Val
            180                 185                 190

Lys Pro Ala Glu Gln Thr Pro Leu Thr Ala Leu His Val Ala Ser Leu
        195                 200                 205

Ile Lys Glu Ala Gly Phe Pro Pro Gly Val Val Asn Ile Val Pro Gly
    210                 215                 220

Tyr Gly Pro Thr Ala Gly Ala Ala Ile Ser Ser His Met Asp Ile Asp
225                 230                 235                 240

Lys Val Ala Phe Thr Gly Ser Thr Glu Val Gly Lys Leu Ile Lys Glu
                245                 250                 255

Ala Ala Gly Lys Ser Asn Leu Lys Arg Val Thr Leu Glu Leu Gly Gly
            260                 265                 270

Lys Ser Pro Cys Ile Val Leu Ala Asp Ala Asp Leu Asp Asn Ala Val
        275                 280                 285

Glu Phe Ala His His Gly Val Phe Tyr His Gln Gly Gln Cys Cys Ile
    290                 295                 300

Ala Ala Ser Arg Ile Phe Val Glu Glu Ser Ile Tyr Asp Glu Phe Val
305                 310                 315                 320

Arg Arg Ser Val Glu Arg Ala Lys Lys Tyr Ile Leu Gly Asn Pro Leu
                325                 330                 335

Thr Pro Gly Val Thr Gln Gly Pro Gln Ile Asp Lys Glu Gln Tyr Asp
            340                 345                 350

Lys Ile Leu Asp Leu Ile Glu Ser Gly Lys Lys Glu Gly Ala Lys Leu
        355                 360                 365

Glu Cys Gly Gly Gly Pro Trp Gly Asn Lys Gly Tyr Phe Val Gln Pro
    370                 375                 380

Thr Val Phe Ser Asn Val Thr Asp Glu Met Arg Ile Ala Lys Glu Glu
385                 390                 395                 400

Ile Phe Gly Pro Val Gln Gln Ile Met Lys Phe Lys Ser Leu Asp Asp
                405                 410                 415

Val Ile Lys Arg Ala Asn Asn Thr Phe Tyr Gly Leu Ser Ala Gly Val
            420                 425                 430

Phe Thr Lys Asp Ile Asp Lys Ala Ile Thr Ile Ser Ser Ala Leu Gln
        435                 440                 445

Ala Gly Thr Val Trp Val Asn Cys Tyr Gly Val Val Ser Ala Gln Cys
    450                 455                 460

Pro Phe Gly Gly Phe Lys Met Ser Gly Asn Gly Arg Glu Leu Gly Glu
465                 470                 475                 480

Tyr Gly Phe His Glu Tyr Thr Glu Val Lys Thr Val Thr Val Lys Ile
                485                 490                 495

Ser Gln Lys Asn Ser
            500
```

<210> SEQ ID NO 6
<211> LENGTH: 55461
<212> TYPE: DNA
<213> ORGANISM: Homo sapiens
<220> FEATURE:
<223> OTHER INFORMATION: aldehyde dehydrogenase 1 family, member A1 (ALDH1A1) genomic DNA

<400> SEQUENCE: 6

```
taagaagtga gatgacaagc caagtatgtt atgaagcctt gagctttcat cgcctggaca      60
```

-continued

```
tcaaataaac cagtatttga atccacaaac aactgtgact ctgggagaag aaagcagcaa    120
aacacagctg tttgggcatg gccagagcgc cactctcaag ttatgtaaca gctgttgtgt    180
aattgtgcat ttaactcaaa acacattttt gagagagaaa acaattagac tttccaaaaa    240
gaaagaaaca gagaaatgtt gaaagaacac agaagtttct atctggtcat caaacataag    300
acacgggga gtcaaaggca ttgggaatga tattgcctta gaatctaggg agttggcccg    360
tgcaccaaat ctggcctgcc ttctgtcttt ttaaataaag ttctatagga aaacaactac    420
acccattaat ttacctatca tctacagttt cttttaaata gagtcaagta aattatatca    480
gaaaccatcc agcccagagg ctgaaaatat ttacagaaaa agttttgcaa attcttgtct    540
tagatgaata aaaagttatg tttaaatgcc tgtaagggtg actattcact gagaaaacca    600
aagcagttga tgcttgaacc catgtaggag ttctcttgtg gagaataggg tagaaatagt    660
aaacagaaat aagagtccag gtttgggagt cagactggcc tgaaatgaaa ttctggtcct    720
gcactaatag atctgtgacc ataagtaagc tactcaccct ctgtatgtct ctaaaatggg    780
gatatgaaat gagggtagaa agggaaacaa gtgctgcacc tgatttgggc aaacaattca    840
gaaattttta gtttccctat gtaagtccca tattcagggg aattggcaag tttcactaga    900
aaaaaaaaaa ttggttgatt ctccacaatc agagcatcca gagtatttta tcttgttcct    960
attgtaacgt ttgctagagc tacaatacaa taaagtattg tacttaaaat gggagtaaca   1020
ctgtttaaaa aattgtcctt cagctaaaca ttaatttaag aacttgaatt gtttggaagc   1080
cctgcttaaa tttagtcttt gtacactgcc tatgttgata aatacagaca acttccaaaa   1140
ccaggattac tttcatttta aatgagtatt aatagatgat attgccatat ttctaattgt   1200
ggtgattgtg tgtgacagtg tgttccgaat tccctaaaag tcctgctggc ttttctgttc   1260
acatatagaa aataaagata atttagggct tctgagatca cagtaggtct acttacccag   1320
cactgaaaat acacaagact gatacgatat tttaaaacta acttagggta gggtgtagat   1380
aaagggcctt tcttccccaa acagcacctt gattttctgg gagatggact gatttcctga   1440
aagccttgtc ctgaagacac ctggccaggg ttctctcctc accagcttct actgagaaca   1500
agtgcccttt tagactcttt tcaatcctca aattctctga ttccaagtct gtcagagaac   1560
agaaagttac atagtagcat taaaaagcat gagaagtcaa aaaaataata actggcctta   1620
gtggccagag cagctgctgc atacacttat cacaggtttc ggctttgtaa attaattcat   1680
ctgcaaatag tgcactgtct ccaggtacaa attcgatgct ggagcactgg tttcttaagg   1740
atttaagttt aaagtcaaag gcttcctgcc ctaggtgtta caaataagta gtgtcgtttt   1800
ctttttttgc tctgagtttg ttcatccaat cgtatccgag tatgcaaata aactttagcc   1860
cgtgcagata aaaaaggaac aaataaagcc aagtgctcta tcagaaccaa attgctgagc   1920
cagtcacctg tgttccagga gccgaatcag aaatgtcatc ctcaggcacg ccagacttac   1980
ctgtcctact caccgatttg aagattcaat atactaaggt gagtaaaact tctattttct   2040
gctttgactc gggtttgcaa aaactgcatt tatgtaaagc attaaaggtc aatttaagta   2100
aacttgtgta aagagccctt tgcaaatata aaaataaaag gcatgcaaaa tgcaggtctc   2160
agtttagtgt cctgatcaaa tatgatctaa atcatatcag acaatctttc ataaatttat   2220
ttcttaaaat atttccaagc gaaaggaatt ctcttctgtg tgaaaggatt cttataccag   2280
gattcagagg actttactaa gcacttctat taacttcact atagccggca tgtatgataa   2340
gagagcaaaa tactcactag agaagcttac tggaaagaac caaacgagta ggaacaatag   2400
aaagcaaaca aggagaaaga gagcatactg aaataacata actttccaat atgtttaata   2460
```

```
aaatgagtgt taaaataggg ggacttaagt ctgataattg gattcgaaaa tcttcagatg   2520
gacttgcatt attttgcata ttttggtggg aggaagaaaa gcattatttc ttcagccaag   2580
tttgttgcca ttggagcaga tgtgtaattg ttaactgata aatatttaga gaaacaagag   2640
caggagctag atccagactt taaaatccgc agctgggggg aactaggaaa tggatcctgc   2700
ttgagtcgtt ctgagagtaa ctctgaactt tgcctgtttc acactgcttt cctgtcagat   2760
cctagaactc caaaacaaac aaatgaataa aacacaatct aaccaaaatt acttgaagtt   2820
atctttatgg tgtgatgcag aaagtatggt aagaaattaa ctcttgcaaa tcaagagaga   2880
gccattttgc tgtctgaatt agccaacagg aaaaacaaag ggcattataa tttaatgata   2940
aagtaaaagt ccccactgtt atatatttat ttcctcactt gtaaccatgg atggctttga   3000
aatcccaagg tctgttgcat tttcattttc ataaagcaca acaaatgagg aagttgctca   3060
gctgattggc tcttttcctc aggaaagtag cagcagagat cagattgtgc ctttaacatg   3120
gttgaccagc agctatgaag tgtattttaa ggtattgtta tcacgaggtt ttgttaaaga   3180
ggaaagattt tttccattta gttttactac aaatggtagc atgaaaaatg cagtaaatcc   3240
ataccgtcaa acaatttaca tttggcaaag gtatgtccaa aaggttgcaa gagtccagtc   3300
tccctcattt tcttattcca agtttgtcat tcacaagaaa tttcaattga aagtgggtac   3360
atttaaaaat acatttcatg aagctcaaaa ttgtcgacaa tgctcagatt attgtattac   3420
tattattaat gggatttttt ttttaataat actacctagg aagatatttt ggtagtctgg   3480
atgcccctgt ctccccactc ctttggcttt gcagaagttt gcaaagtctt ccttgtgtgt   3540
gtatttcaag gaagctctaa tgtaaataac cttcctgcta aattaagctt cacttagtag   3600
tcattaacta agcatgtaag aagcggtact agacaaatga gatggtccta aaaatctaac   3660
atacaagcac agacctaatg aacccttaac acagagagat gattttgaga ttgaaaccta   3720
ttcacttcga agtcactgtg caacaactcc cctctaggga aagtgactga cctaagtgtc   3780
caaaagaagg caagactcaa agagcaggcg ttttgctctg tgtttaagaa cttttctggg   3840
taaaaatact ccaaacaagt cagtgaattt tgatttctcg tgcatcttct atataaatct   3900
gttctgctca gatagcattt tattgtttaa tttattggtt acagcgtttt cacacttggg   3960
aggacgccag ttatgtatgt aattaaatct aaatgggtga actttttcaa atgccttcgc   4020
atttttgtt tactatgtcc cagtgaagaa ttggattgaa tttgctcttg caagaggagt   4080
taaaaaaaaa atgatggtta ttaactataa aaagttccct ggttacaaac caagtaagca   4140
aggagtttat agtgtctgag gaattatctt ctattaccag cccctaaagt cttgtgttat   4200
ttttctgtta ctattctaat gtcctttttt attattatta tagctagaag tatattggtt   4260
gttaggacaa gttggagaga acagacaggg ttgagtaaaa aaaaaaatat tacaactacg   4320
atagaaaagc tacatactct caagcttggg actgcttttc acccaaacaa aagaatttat   4380
tgatgcatat gtttttatga cttattttct agtacagtct gattatttct ttgttggggt   4440
agattaaaga gagatcagag tttaagaaat gctttctaaa attatacaaa agcttttgga   4500
atttaaaacc tcaaaaacat cgctataaat tcactaatat gaactcatat cccatcctta   4560
tcctcattac tcctctttcc aactctaaat gaaccccaca ttttccattt tattgagcct   4620
ttaaatgaag agattctttg aaagttatgt gatcattggg caagctacat tacttctctc   4680
tgcctcggtt ttcttatgtt taaaatgggg atgataaagg cacgtatttt ctaaggtcga   4740
tgaaagtatt aaacgaactt aatgcgtaca aagcccttga aataatgcct ggacatggga   4800
```

```
aatgatttaa cgttagtgat cctagtccta tttttctgaa tcctttccag tttttccaga   4860
attttccctt ttacccaacc tttcctagac ctgtttccta caagtatgcc tcacgtcttc   4920
tcctagcttt tctgtcactc ttttttgtac agtcatgtcc catctgacaa agattgcatc   4980
agagtgaagt tccaagggtc ttccaagatt tcagggatca aaaattttct cctacaggat   5040
tcggtaactt tgtttgccat tctctcttca caatactgtt gttttacctt ttctttttc    5100
ttttttttt tttataaaag ggaaatagga aattcaagaa gacaagcatt ctcagacaga    5160
attcaaacgc caaaatgttt aacttaatta gtaagcttca cttattaaac catggtttgt   5220
tcatgctaca aaagaccttc atcagctaat gacattttac tcatacatac acacacacac   5280
acacacacac gcacacacac acacaataaa taattatagg taaaatttat tgtgcttact   5340
ctgccatgac tgtttaagtt cttgacaatg attttattta ctcctcataa taaccctatg   5400
aggaggttac tattcctgtt tcacagttca gggaactgag gaacagagcg gctatgtaac   5460
ttactaaagt tacacagcaa gtaagtgaca aagctacact gccaatgctg gcagtttgag   5520
ctaacacact agcaagagac ttgtctaagg tcaattccac tactctggga cactgacttg   5580
ccagaatcct cttgtatcct tcttcatcct gactttcatt tgcccattgc tgattaccat   5640
ggtctttcca gctgctgctc agctgttccc aggccaataa gagaaagttt gcagccaact   5700
tagaaaaaga gaacaatagg gaaattgaaa ggaaataggt tttctgcttt gactgaaaat   5760
gtgacgtttg ggctaggaga ggctatgagg cagaggactt tgacatggat gtgaaatgtc   5820
tgtgtgaact acatttcttc aactcctatg gaatcgattt tggttagagt aggagattgc   5880
tttcctagat ttctggtttt gtttaaccct tctgggttaa agagatattt tcaatggaga   5940
agagttatga atcattgaat aatacgtccc aggcacgatt tgaagtgctt cttttccccc   6000
atgattatct ctttaaattc ttacaacaaa caaattcagc tacatgaact tccaaatacc   6060
tcctttgtcc cctttgcttg tttctccctt ttgcttttcg tttctcccat atttcccttc   6120
ctcttattta acaaggcctt gaatgagtgc cctatgctag ttctcatgat ataagagggc   6180
taatatgatt cacgtctcat gcagcctctg ttcctggaag gtgtgtggaa tagtgtgggg   6240
cagaaaataa gagaatgctt taatcagaaa ttaggataaa tgtttaaagc aaaataactg   6300
aaagctgaga gaatatgagt agaagagctt ttgatgagga tttttgggaa ggtgctttaa   6360
aggtaagcct gagggatgta gagaataagg tggccaagag tagggaagaa caaagatcca   6420
gaggtcttac cacatgcaaa gaccccgagg acaagagcat gttatgctca aagaactatc   6480
caaaggctaa tctggctgga gtaaagtgaa taagggagag aatggatgag atgaaactga   6540
agtacaggct ggggccagat cggctggcgg attttgagga agatcactga gaggtgctta   6600
aaacaggaaa ggacttatgt tcaacgcaaa gctgattgtg ctgtgatgct gctttcactt   6660
gggaaatgtt tttaacttcc ttccaactga agcaatattt tgtttgcttt gggcttggaa   6720
gcaggtgaaa aaaatagctg actggctgca aggtgcagtg actgaacaag ctaaacctgg   6780
cttcaatttc cagctattct atgtatttaa ttatatgacc ttggccaagc ttctcatccc   6840
ctggagcttc agttcctctg tctgtgaatt gggaatgaga atgactacct tggaaagtgg   6900
ctgtgagaat taagtgaggt aatttgtgga atgtggctgg cacttattaa ctacttagtc   6960
ctttctctcc ttgattctct ttcccaagat gactcctaga attatatgat cattctgttc   7020
tcaatgtaag ttatatttat attgcttatc acagctcaaa actgatttca tatatttctc   7080
tcatttgagg tgcatcatta accactgaga ggagctagaa aagatgttag cagagtccca   7140
tttcaaagct gaggagcccg agctcagaga tcatgactga cttaaggtca catagctctt   7200
```

```
aaaatgcaaa agtagaataa actggattct aaatcttttt atcttggatc tgatgctttc   7260
ccacatgata tcctttttc cttaaatatc aaaaccagta gtactagaat ctcactcaag   7320
aaaacctaat caagaaaaaa atctgaagta aataacacat atcctaagag aagagggtat   7380
tatccccctt tcccaattag ctctaacaac tgttttcaca cctattactg catttttatc   7440
attcattcct tactgtggtt gaaagaatag atctaggctg aagtctgaga ttctgtgttc   7500
ttaacagtct ttcagctttt gctgatgcta ccaaaatgtc tgttgaccag cagcaagggt   7560
ctaaaagttt taggtgagtg agccttataa cttcaatgca gcaaccacct tccagttact   7620
tcacaataga gcttccagtt tcttccagaa actagcactc agccacatca gaaactttcc   7680
tttcagaaag tgccagagct aagcagaaac atgatgatgg ctacaaacca gtgacagaac   7740
caatcattga ttttaatagt gggagataat catttactaa tatttagaat gctcatctct   7800
gaggactgct gtcttggcaa gttgttttgt tttctggcac ctgcctgact gtaagaaaat   7860
ggaattaaca attctaaagt aaagaacaca tgtcctaaga gagggtattg tccccatttc   7920
ataagggctc tcagtacaac tctttatata actttgtaac agggacttta acctattgaa   7980
tttgtcacta catacttgcc agaatgaggg aaacactctt agagaatatg aaaaataact   8040
catttgaaga ccaacccaaa gtaaaggtaa tgactctgaa atggcatgga taatctatag   8100
gatgatatgt tgcaaatcag cataaaataa atctcacaga aatacagaca tcaaacagag   8160
atatctgaaa atagcaatta tctggcttgg gatggtggtg tggggggtg cactttggtt   8220
tgatttatca tgatgctatt ataactatag ccaggggata tattatatgt ttacaaagtg   8280
taagtgacaa catagaacca tgttcaaaag aatttgagca aggattgctt cacaaaccct   8340
tacttagaat ccaataaatc agaaaagtaa atctgtgtaa tactggtttt cctgacgctg   8400
acatgttttg ggtgtataga tgtatatagc aaaagtatcc acaaacttag aagcattgct   8460
tgagaaggat gtgaagtgtt gctaatattg ggttttctga tattatctct acctgattca   8520
ttgtaacgtt tgacttacta atggaaattt gttcactggg gaatttgcac aaatctcaca   8580
tctctaaaaa ctttgcctga accgttccct cccccaaccc tggtcccatt tccactgact   8640
atttccactg ctctatcgat actttttag atgtcaaagg aatacaaata actactgaat   8700
tatgctttat atttggcatt cttttagaag gaagagggct tacatgcgag caattctatt   8760
actaggtctt gatactgcta aaaatgggca gaactttcta tcgcttctac atcttaactc   8820
tgatacagaa aatatatgat gtacagaagt tgctgacaag ttttgttatc atctctagga   8880
cacagtgatg gagtggctca aaacaaatgc tgtggcatct tttctctttc cctgacacaa   8940
ttgaaaaggc tgatggggtt ttgcaaacaa caagaaaaaa gagtatatac tcacgttact   9000
aaagtcagac tatcatttaa agcaaatgaa aggaaaattt tatttctcct attttttgtt   9060
ttcgtcattc tgtcattttg ttttcattca tttgatgaca gttaaaaatt ttctttccct   9120
ttgttatttc ctccttaatt tccttttaca ttttctaact ttgagtctca acattttgct   9180
ttcctgcctc agggttaggg tgcaaagcag ttgccagaga tccagctttg attcttttaa   9240
atgtttaaca ccccacctga cttttgttca gtctctcctc ctcattattc atctccgatc   9300
tcatactccc tgactcccag cggcctttag tactttggta ggttcctaag ctgagaaaag   9360
gttgacacat ttacagcaca caccagtctc cacaggttca caccaccacc catgcagcct   9420
atgctgtgac tcagttctca agtttgaaaa ttcacatgga tgacattaaa tggggactct   9480
catcaccctc cctctcgttt ggaaaatctt aaaagaaatt ctttgtgcat tgaaaatgtg   9540
```

```
atctcttaaa atctctctcc caccaagaaa gtattgcctt cctttacaga ctctagggct   9600
gctggcccag ttgctgccct gccgagataa tattaattta aggcactctg agtatctttt   9660
gcaaggagtc aggggctccc cactttagcc cacagactcc aaaatctcat atcagcagat   9720
aaggcaaata gggctttatt ttgccactag tcaaaactag ctttatccaa gccagaaata   9780
ttttgagaaa attatgctta tttatttaga actgtagatt tatacacaat acattaagac   9840
ataataactt ttactctgga aaggcaattt ttttcacaat tatgactaat tcttggacac   9900
cagttgaatc caggaaatgg ctacttgttt atcaaaggta aaatgatgca tttcttaaaa   9960
tgtggcatat ctaaaatctg aagtgtaaaa atccatttct aagttgcctc aacatttcta  10020
ttgattgctt ccccatatag aaagtacttg aagtccaaga gtatgcatag gcatttataa  10080
tttccaatca atatttcaaa cagaaggttg atgtctactt tacatatata ttattcaaaa  10140
gtcacctaag tccaaaattc ataattagaa ttgagttaat atataatggt tacatagaac  10200
ccaagaatat tttactttta tagtatcatc tcttttcctc taagctggct aaaggcaaaa  10260
aacaaatgga aaataatatt gtcaccatta tagaacatta aacaagccta atgtaaattt  10320
tataattatt ataacaaaca ttcattagcc tagacttctc catataacca ttaatataac  10380
tataggaaca gtgattatac aaaaacgttt ggtcacacag ttagctggaa ggcaaatgcc  10440
caatgtaaag ctcctataat taaaacagaa aaaaaatgta tttgaggtag gccctatgaa  10500
taaattatct gtagctaagg ggaagaaaaa gactgggcaa tacctggcct tctaaccatc  10560
taggtcatca cattacctat gccaaattcc cttttcatgc tgaaacgcct ctgtttgtgg  10620
gagaatggca taattcataa tttgtagact gcactgttac atcactctcc ttcaaaagcc  10680
tgtgacctta tgataggatt atgaaattag tctcaaggct aatttcttgg actctggttg  10740
gtctacttca aatctacttg ggatacttta aaatcagtat tcctaaacat ccatttgatc  10800
tggtctctct cccttttttat atccagaata gagcctaaac ttctttctct ggggatcagg  10860
atctgccaca aattgacttt attttcaatg tcaggcctta tctgtgactt atgtccactg  10920
caactccatt ctgttgggag ctgctctgtt tactgtgtta caaacctcca aagatttgtc  10980
cctcccttta ctcttttttt ttccttcttt ccaccaatcc agttccatcc ttcaaagaag  11040
cattctttca gcctatgccc ctctacacca tttattgaca acaccgctgc tttggccatt  11100
ttgctccaca gtctttaatt ctgtactggc ggctcttgat atgaatacat tctcctctta  11160
gattataagc ccctgagagc agaggccatg gctaactcat ctctcatttt tccacaataa  11220
ctgccagact atgtctcaag tatttactca ttattggaca aacacttttc tgataaagca  11280
aaagttacta atcatgatta tataaatgtc aacacaagtt caaacacaag ttgggctcac  11340
agtgtcctcc tgtcttaaag gttaaaactg aataatgcag aacagtgctg gtaatttggg  11400
gtcctctaca gctgatctct tcagttgcct gcaggctgcc agataaacat gtgttattac  11460
ttcaggttaa tgctcattta caaaacattc actggcttta atctaaagtg gcagttttat  11520
gtacagctta gatgcaaatt ctgatcatgg aactagatgg tacatacata ctgtaataat  11580
tcttttacaa aaaagtgtgt aaagagagta aaataagcta taatatattg agagcatatt  11640
attgagaact tgaaaccaca gattatcaca gacctaagga taagaggact cgggcgagaa  11700
ctagaaagtc cgaccacagg cctagcaaaa tgtaattgat tctgtatgtt gttttatttt  11760
atttttaatg aaattacatt gtagaagggt gaaattctgg atctctgcca aaatgaaatc  11820
tgtgttccct tagtttacag gtacaaaatc taaggtggta atacaatctt taggcagaga  11880
gaaggcagaa ttcccaagtg aataaatctg atgcaggttt tgaaagactg atttaaaagt  11940
```

```
ctacggcagg tatcgcaata tctttagttt tttgtttgga attttatggg ctgatatgta  12000
gatatctaac attaacacaa agcagaacat aagtaattta tcagtaggat actaacatgt  12060
tatgttggaa agaagaaaaa agagattaaa ttcaattgga gcaactagtc aaatcttcat  12120
gaggagatga cgcagtaagc tagaatttga agtaaaaata gaagaaaata gtggaactct  12180
agtctaaaga acagtgtgaa taaaagcatg ctgcaaaaaa cagcatggtg tttgaggcag  12240
tagaatgagg ctggaacaaa gggtaaactg agggaatggt agagcaaaag actggaaaag  12300
catgttggag caagatcgtg aaccacctcc agtgccatgt taagcagtct gacaatagag  12360
gatcactaaa gtattctgag gagggctgta gacagaatct gaggaagatt atgatgacaa  12420
ggtgaaaatt aaattttaat taggcagagg tagggggcaa agagaacagg gaaagctttt  12480
ttatacttgt atagaacaaa gtgatacaaa agggtaccta gggattattt gtgtcattaa  12540
cagaagaagg aaagtgtgtg agagataggg ctgggggaca gtgtgcatga gcaagcttca  12600
gaactttggg gtgagagcag cataaagcta gagatgacag tgagctgagt tcgggacaag  12660
ttgattaagt tctttcccag ccatcccttg agaagaaaaa tactaagctg taagggcata  12720
aatggaaaca ctctaagaat aattatggga ttctgtaaaa tgtatttctg atagctagag  12780
tgttgattca ctctaagaga cattgggcaa atcagcactt tcgtctgaat ttatttttcc  12840
tcaagttgat ctaagagcct aatgtttttt cccaaaagat aatacaatga attttatggt  12900
cttcatctgt attcagttaa tcttgtttct gtaatctgat agggtttctt gatacttctt  12960
ccatctttct catttcccca tatatgtatt tttgcacatc tagtctcttc atctgaacag  13020
ctttgggccc cttttccctt tatttaggca tgcccatgtg ttttaccatc aatttcaggc  13080
tagtactaca attcctttga atgcttctaa ctatacagga taattttctt gtatggaaat  13140
aatgctgttt tcttgtatgg aaaattatac tggcatgaat gggcaaacaa gacggcttat  13200
cctcttcccc attttgtagg aaatcacaag tgtcatagag tattcatttg cagaacgtta  13260
tagatcttat ccatgagtag ctgatggatt atagatcttt gattcaatta agttagttat  13320
tcaagaattt tttactgagg ctaaaattgc ttgagggctg ttggacactg aagatagact  13380
ggaaaaccat acacagccct tgatggaagg cagacactta aaaatgacta tttaaaaagt  13440
gacaaattgt ccaatggaag tatagaggag accagggaag tatattttgt ctaaataata  13500
aatcacagaa tatagaatga attatattca ggcatttagg gatatatagt aatatacatt  13560
ttattactct gatagaattt taagctatgc tagtgatcac cggggaattt ttaataaata  13620
agtaatttgc atttagcata gtagctaatt taaaccttgg aggagtgttt cattacattc  13680
tccctcgggg ttgaactatt aataacttat ctttagatat ccagtaagaa gggatgtctg  13740
aattaggata tatgttataa tccagcacat atgtcacctt cctttactcc ctgtgttagc  13800
tacctctgat tcaaaataga ataaactagt ccatcttgtc ataagtctaa cagaaagtta  13860
tatactatcc aagactgtat ttatgattgt tttcatattt caaataatta gaaatgtgaa  13920
agctggctcc tcaagaaaag acaaattcag tgacatgaaa gttgaaactg agatgtttta  13980
aatgacatac tgatgctttt aagtatttct attttatagt acacacagac aaaatttcat  14040
attttttagt gcttactgtt tctttagttg catgtctatt tctcatagtt accattaaga  14100
aatcttgttc ctgattttgt ctgaagacaa cgaaattacc aggtaatctt ttgaaaagga  14160
gaataaaacc atatgctttt aaaaagccaa tgaaacaatg tgactagcta attttctcta  14220
agtgaactcc ttttagaatc ctttagcaaa attctttttt taactttaaa acattaaagg  14280
```

```
attagaaaat agtctcttat gattccaaat caccagtagc cgaaaatgag gatgttcaga  14340
atttaaagtg gaaaatagaa gcaatcatta ataaagacca agcccacaaa agcctttgct  14400
ttgcctcaaa ttcatggcca tttcaggtaa aagcattgtt ttctagattg ttttctccag  14460
tatgtatttt ctagtgttga actgattgca taccttaaac ttaaaagcat tatgtacttc  14520
attttagtac atgtctatgc atgtgaacac aaaatgtctc aaacagccag aaagttttga  14580
gaggtgaaga gatgtgcatc atttaggcat ggtgaaatgc tttagtttaa gtttatgaaa  14640
acttccaaaa ttttctgcat atttaagcgc cttgtatgta ttttctcttc atctctacag  14700
atcttcataa acaatgaatg gcatgattca gtgagtggca agaaatttcc tgtctttaat  14760
cctgcaactg aggaggagct ctgccaggta gaagaaggag ataaggtgag tttctgaaca  14820
ctagtttcat tttatgccag gtttcttggt tttttgccat tctgagctcc tgaaccccat  14880
tgcaagctcc aaaagacatg ccatgaaaat atggtttctg gggcagctta ggaaaattgt  14940
ctaagttgtc cttgttacca aaaaaaaaaa aaatgctctg tagttatgta ataatgataa  15000
acctgtgctt ctgggtgtca tggtgatttt ttttcacatc attttccttt attttcaatt  15060
gaaatagtat atagatttat tttacagact atataagaag ggattgatca taggttataa  15120
agtagagaaa tcttcagctg ggcgctgtgg ctcacacctg taatcccagc actttgtgag  15180
accaaggcag ttggatcact tgaggtcacg agttcgagac cagcctggcc aacatgggga  15240
aacaccgtct ctactaaaaa tacaaaaatt agccaggcat ggtggcacat gcctctaatc  15300
ccagctactc aggaggctga ggcaggagaa ttgctttagc ccgtgaggca gaggttgcag  15360
tgagccgaga tcataccact gcactccagc caaaaaaaaa aagaaaagga aaaaggagag  15420
aaatgcttta ttcatatgaa attgttcttt ttatgttgct agataaaact aaaagttatt  15480
atagaacttt tagaacaata tattactaag ttattttatt aaaaatcact gcattaatat  15540
tattattcaa cacctgtaaa aattatatta tagaataact taaattgact aacaaattac  15600
aagcgttgtt attttccagc taataataga aacaacaaaa accagttttt atttagtgaa  15660
aattgttctc aagttctaaa tgctatcttc atttaaaact taaagcaacc ctatagggca  15720
ggtactattt tgagtcattt ttacaaataa tgatgagatg gcagagtaga aaggctgagt  15780
aatttactca aggtgacatt gctaataagt aataacctca acattaaaat gctgttcctc  15840
tgacactata acctgtgcct agtagggcta ctgcttcact ttgtgattat tatgaaagta  15900
agatagggtt ggccgggcgc agtggctctc acctgtaatc ccagcacttt gggaggccga  15960
ggcgggcaga tgatctgagg tcaggagttt gagaccaacc tgaccaacat ggtgaaaccc  16020
cacctctact aaaaatacaa aaattagctg ggcatggtgg tgggttcctg taatcccagc  16080
tactggggag gctgacgcag gataattgct tgaacccggg ggtcagaggt tgcagtgagc  16140
caagatagtg ccattgcact ccagcctggg caacaagagt gaagctccat taaaaaaaaa  16200
aaattaaata gtctttctta ttatgaaagt aagatatccc agcactttgg gaggctgagg  16260
cgggcagatc acaaggtcaa gagattgaga ccattctggc caacatggtg aaacctcgtc  16320
tctactgaaa atacaaaaat tagctgggca tggtggcgca tgcctgtaat ttcagctact  16380
cgggaggctg aggtaggaga atcacttgaa cccgggaggc agagcttgca gtgagccgag  16440
atcgcatcat tgcagtccag ctgggtgaca agagcgaaac tccgtctcaa aaaataaaaa  16500
ataaaaaatt agatagcata atattaaata aactttttat tctcctcctg ggtgaggaga  16560
gtaaaaaact tcagaatatt tttctgaaca cgtaagtgtt tctaagtcta atttgaaatg  16620
atttttctgc tctttagttg cccaggggtt gccaagtttt aaatttctgt aaagaagtaa  16680
```

```
tgttttattt tattttatta ttattattat tgctgcagga aaagactact gggaaattaa  16740
agtcagcaac acccaaggat aatattattc atgacaatgt gttttagtta attatagcga  16800
tcacatgttc ctgccagtct cctgcccagt cttttccatt actttagccc cagtaaatga  16860
gatcacaaat ctcaacgtac tgggccatgc agatacttat tccaagatag tgacacacct  16920
gagggggccc ttttagattt aggagaggcc cttggttcag atttcagtac gatgaaaaca  16980
agtaagaccg aagtctcaag ccacaggagt acggagttca accatagggg ttaacaattt  17040
gagaagtaga aacaaaataa aatgatgaca aatgtcactg gctttcagat tcagatttac  17100
tctttatact gaagagttca ccaaagcata aattctccat tctgcttctc actgtctgtg  17160
ggaaaaagtg cacaaacaaa ggtcctttat aatattactc aacctttgtt tatggcctct  17220
ttcccaggcc accgcattaa cttaagagtt tcaacttcgt catgcccagt gtccatcccc  17280
aacaattgct tgctagtcac tgcctctgta catgtccaca gtgtagtcct caggacctag  17340
ttcaagtcac catctatagt aagagcgtag attttcaatg tttgtactta accttctttg  17400
agattctgtt ctttttcatg taaaatgagg agatagaaaa tgcttgagga gttaaatata  17460
tagagctctt caacggtgcc aggcatatcc taaagcttca gtcatgcccg ggttttatac  17520
ttatttaaag ccttctctaa ccttctcaag cagacttact ctcttctgtg tggttatagg  17580
acattgtatt tgcctgtatt ataacctttg tattatacag ctataggtta atttgtctga  17640
gacaatatgc ttcttgcaga gatcaacact gcatctctca tttatatcct tggtttctgg  17700
atatagtata tcctataagt atgctatact atattcgata gatatactat actatagata  17760
tagtatattc tataaatcta tgaagtagtc ttctttttca tcaagtgttg aatttccata  17820
cattccacat tcctcacctt aggaatttag tactaacctg actattggct atggcagaca  17880
ttctcaaaat ttagcctgtc tcagaatgtc caggaaggct tgttaaaaca cagatagctg  17940
agccccacct tcccctagat ttcactgcaa taatcttaga atgggacctg aaaattttca  18000
ttttttatca attctttggt aatgctgatg ttgttggttg ggaaggaggt gagggaatgc  18060
atcttgaacc accgaactaa agtgttaagc tgttaagttg tatctcctct caagcgttaa  18120
catttaacag gggtcaaaga gttttgacac ctaagaaagt tagtgattga aaactgtact  18180
gtggtgatca ctctgcacct ctctgaaatg ctaccaaacc aaaattgggc atagaaatac  18240
tgatcatccc tggcaaggtc tataggagcc ccagaagcct gtgccctata agccattccc  18300
agaaataaga gagaaattta ttcttcacct ttcaaagaag aatgaacgcc ttttatcaga  18360
gacttcagga gatccacaca ccaccacctc aaatgttcct ctagttgctt gagtggctct  18420
agcaggcctg ggaaggtgag aaaagcaata aagggcaagg acagagtgag cccttgagag  18480
ctacatactt tctctctcca ttcaagagga aggccagatc tgtttgcagt ttgcaactaa  18540
caaacagaaa aatattattg atgttttaat tctggagcct tgaacatcga cctttgccac  18600
tgggattaat tttattagga aaacaaatct ctatgcccaa agttccagtt gaaaccttgt  18660
caggcagtct gaggactttt cttagtgaag tttgtgggat ttacctcctt cctaaagtat  18720
agtaagggaa agctaatgat catactggaa gacttagaaa tgtttgccac tgatttgctc  18780
tgtgcttctt gacaattact attgcttacc caagagatca aggatgctca ttaacatcta  18840
cccaagcttc aaatcaggtc acaatgccaa ctgagttggc tggtcaactg gttactaaaa  18900
ctaaaatgtt gatggtataa actgttcatg gtaaaccagt ttgaacatct agcactctta  18960
tcatcacatt cttttttgaa ttattttaaa acatattttt aaataattat tgctcttccc  19020
```

```
acaattttgc cgacaaatgt atagtaaact ccgacattgc ttagtgaaag gtacaaatct  19080
agtaaattac atagtcacag taaacctaat atgctgtatc tgactcttta gataatgagc  19140
caagaggttt tagggattta atttgtaagt agaatggggc taacaatggg ctatataccg  19200
cctttcaacg gtattataaa gaaaagagga agggcaagaa caaatggagg ttacaaagca  19260
aagtacagat gtgggtggga actgttttct tttcacttca gtggttcttt taggctatat  19320
tgactaatcc tgaaaactgc ttttaatact aaggcatgac ctaacaaata attggtgggg  19380
ataaaagtaa atgtccgtta aagtaagtgc ctttgacatg tgtaaaagta aaactggtct  19440
gataactatt ttctccatct ctgaatgaat ttaatatgga aatgtaccat ctgggagtga  19500
tggaagagtt cagtccttcc ttaactgtgc tttaggaggc atttgatatc tcatcatcat  19560
ttgaactgtc tttttacatt cagcttgtgg cccttacttc aaaaaaaagg agcattttca  19620
gtgctataag caaaattgtt attgatggtg gcaaatctga gttaatgtac caaattgttt  19680
tctgtttaat taaaaaatta tatccctgaa aattccagtt ctgaaataaa aatttaaaaa  19740
atgctagtcc tggaattaag aaaacaataa ctgttatgtc taacagtttt tgaataatgt  19800
ataagttttg ttgtatcatg gaatctatta aaatatgatt tattatgtaa atgccaatgt  19860
agttaaatta attatgtaag gcacccctta tataaaatca gtacaacatg atgagtttat  19920
aaaacaggta accaaattat tcaaaattta tttattgccc attgtagacc cagaattgta  19980
agaaatatta cagtttacaa aacaaatagc agtatatatt tgttgcaaag gaggtcatta  20040
ttagggcagc cttacagaga tgtaagaact agattttgta gtcagatgtg ggatcaaagg  20100
ttgattctac tgtctgctag atttcatatc catgagccat agtctattca tttataaacc  20160
aaggctcatg atacttaata gtaatagtaa ctatggggct ttaaagaact ttccttagtg  20220
cctggagctt agtaggctct tagctagtag ccatcatcaa gctggactag tctggcaagg  20280
ttttaggtag attgatattt gagctgggtc ttaaagtata tataggattt agaaagtaag  20340
ggagtatact ggtataatat tctaggcaag gagaactaca gacacaaaag taagaaggag  20400
ttgggtcaga tagagtagaa aaaatgtaaa cactaagttt ggataggtga gatgtggtct  20460
gaaaatcctg ggccttgaaa accagggagg actttgacct tgagattgta gatgaaaggg  20520
aacaggtgta aacatttgaa agacaaagtg ataagataaa attatttgca gaagattagc  20580
ctggtgatag tagccaagat agtttgagga gagaagagaa tgaacttgag acagcattga  20640
caatatgaaa taatagggcc taaaattgtt cagagcagtg aaaactgaaa ggaaggatta  20700
aaatacatta gaacttgcta ggtgcagcaa tacacaccta taatccctgt gtgcctgtaa  20760
tcccaccacg ttggaaggca aaggcagcca ggttgcttga acccaggaat tttagaccag  20820
ctttgacaac atggcaaaac cccatctcta caaaaaaatt aggcagacgg tggctcatgc  20880
ctgcaatcat agcacttcgg aaggtcaagg tgagaggatc acttgagccc aggggtttga  20940
gaccagcctg gacaacatag caagacctca tctttactaa aaataaacaa ttagatgggc  21000
atggtgatgc actcctgtag tcccagctac tccagaggct gaggtgggag gatcacctga  21060
ggctcgtcag gaggtctagg ctttggtgag ccatgtttgt gccactgcac accagcctag  21120
gcaacagagt gaatctccct ctattgagag agggagaaat tgctgagagt tatattaaaa  21180
tttaaagttt taactgctag gacaacagta acaattgcca ccattgaata atacataatg  21240
ttctaacata gaaaatgttt aaatgttatc ttattaatct tcattacaac cctgtgaggt  21300
aacatacccc aatttctttt ttcttttgtc ttgctttttc tttttttttt tttttttttt  21360
tgttttgaga tgagggtctt actctatcac ccaggctgga gtgcagtggt gcaatctcag  21420
```

```
ctcactgcaa cctgcacctc tcaggttcaa acgatcctcc cacttcagcc tcctgggtag  21480
ctgggactac aggcacacgc caccacacca agcaacatac cttgatttta aagaaaagaa  21540
agctgaacct tagagaagtc atgccacaac atatttcatg gtttataata atgttttggg  21600
atagtgattt gattgtatgt ctctcccatt tgattgaata ttccaaaagg acaatcttct  21660
tacttcactc tgctgtcttt agcggaggga tgatgagaat gctgcagagt cgaatattta  21720
tcaaaccttt agctagaggg atgaatggtt agatgcctca aggtttacac agctaatgaa  21780
gaggaatcag aattcaaatc tgggttgttt tcatatcaaa ctatatatta actaacatta  21840
ctgtatttct gcatctgcaa gattacatat aagatgtgag aaaagggggc gcatgatcca  21900
aaggacataa tcataagaac atctttattt atagcagcat tctttaggga tgtgctttcc  21960
atatgggaga gttacttatc ttgaagccag ttctccgtat ccctttggga ggccaagatc  22020
cctatgatag cccatatttg gctaagacca atagcaggac actgaacaga aagatccaaa  22080
tgaaagctgt gtcatacaga tctgtttaaa cacagaccag catgtatttt ataagctctg  22140
gtatccacag atcatgctga caatctcaga tttttgtggt ttgctttttc tttttttcaa  22200
acagtgctct gtaaatttag gaaaaagtta gaacgtgtgg catgaaacaa tgtctaaata  22260
taagcaatca atgtgattaa ctgaatgccg caaatatgca ctgtatatgt atttctcagg  22320
aaaggcaggc aataaataca tatattttgt atatatcatc attctctgaa aagttagaca  22380
gtgagatata tcagtgtgtg atgtattaca ctgaaagaat ctttgcttgt agtcagtaaa  22440
tattattact taatcagacc agattgtgct tctaaaatat ctctcttgcc ccagatcata  22500
ttattttggt gataaatact agaagaatag tttttttgta ttttaattca cagacttgta  22560
agtgtgggtc ttcttgattg aatatagcct aaggaggagg atgttaattt gaggtccatt  22620
tgaggggaag atatctcctt agatgggatt tagcttaatt gtgtacaatt ttttaaaaaa  22680
atctagggtc attacttttt ctctccccca attcttaaag ggaattgtgt ctcctgcaaa  22740
atattgcaac ctactggcct gtgatatagc cactatttgt ggagctatac aattccatgt  22800
agtggccagt tctatgtaca aaagaacact ggaatgatat attcctttat ggtgtttgca  22860
gtagtagtag gtatgttctg taagagctca gaagaggtct gaacagggat ctgcagggga  22920
gtggagtggt cagggcaata tttgtaactg aggtgaattg caaaagaacc agagaatata  22980
tctggtgtag aaaaacacaa cagagaaaga aattgagtga aggcactatg agagtgaagg  23040
acaggaggct acactgaatg tggagtcact ttactctttg acttttactt gaattaatgt  23100
agttttaagc catgcatctt taataagaaa ctgacttctt tatcggatta gggatttaaa  23160
aggatctctt tgtacccagt tgggaaatga gaggttgtca catgcacatc ctactctatt  23220
agttccacta tttccatgcc ctgttccctc tgcacaagag gaatgagcac atgtttctaa  23280
ggtttattct tcaacagcaa agcaaagttc ttattcaccc ttcaataggc tcttcatgaa  23340
agtggacagg ctgttgagtc accagagacc aaggaagata ttcattattt tggatcttga  23400
gcttgacctg gaattcctgt aacccagtca ctaagaaagt ataatgtgtg gtaaacagca  23460
aagattctac aatcagatgg gctcccttta aaactcagtt cagccacttt tagttattaa  23520
ccttgagcaa agctcccgtc tctctttgct ttagtttctt catctgtaaa acagggaaca  23580
tatttgtgcc ataaaattaa tgagaattaa atgagctaat aggtataaag tcatcagaac  23640
attacttgaa acagggcaag cactcagatg atagcaacta ttaaaatcat aaaacactta  23700
tattctagga aatccagcat gtgctaggta cgtggagctc atcatgtaaa gattattcag  23760
```

```
caggagtaat tccaacatac agtagttgaa tgtgcgcaat gtgttagact ttgggataat  23820
ggagacacag tgcctgctta tgaggcacta cagtctattt tacagggtta ttggcattaa  23880
atttgcttgc ctaatatgtt tagcttactg aattgaattc ctgttgactt acaggaggat  23940
gttgacaagg cagtgaaggc cgcaagacag gcttttcaga ttggatcccc gtggcgtact  24000
atggatgctt ccgagagggg gcgactatta tacaagttgg ctgatttaat cgaaagagat  24060
cgtctgctgc tggcggtgag tattatccaa gctggatggg tagctagagc tctcaaaagc  24120
attcagcgtt tgaaatggca agttgttttg attttaggga tcactatatg ctctctacaa  24180
acaaaatgaa aacatttttt gtcccaatga ataggcccct taacattgaa ctattctcaa  24240
atagtaatct gcatttcaat tctggatgat gttaatttct gctcccataa tagattctac  24300
ggtctaaact ttagcaaacc caagttaaac caaattttag aaatttcttt accttaaaac  24360
ttctcagagg tttcaataag atcacatgaa gtttgagtct cctagaatga tatattaggt  24420
ttattcaagc atttgaccac tgagctcttt tgatggaaaa actcaagttt gttaagggtg  24480
cccaaaatat ttctctaaaa taaatcttat ttctcattag tctagctcgc taagatattt  24540
aataaatggc tacttttttt cttcctgaaa tgtgtctgtt cacaagggtc ataattaaat  24600
gatgttcttt ttacagatga aagaggcaaa aaataaaaaa aaatccaatt attaatgtgg  24660
tttatcaaaa tcatgttttt atgaatacta tttttgtttg tttatgtttt agcagttaga  24720
tgagtcagag cataaatatag ttgggggagg gtatttcctt gtttctgttg tctcaattgg  24780
gcattatgat gaagccaatt taacataaac caataccaag atcaggtttc aagcaaattt  24840
catctttaga atctgaaagt ggcagtaaca aagaagtcta catttttaaa aaatcaacat  24900
tagcatgtat ggttaatagc aagtatggtt aatcaaagga ccatttatta ctcaaatatt  24960
caacataatt tgaaatacac aaaaattcag aacgagcagc tatgtgcaat aaaactatag  25020
taataaaaat gacctgtagg aagaaagcag aaaatgctaa aacttggctt ttctcaatta  25080
tctgatttgt tgactgcctg tcagcataag atcctataga gagaaaagta caggcataca  25140
aaagtcacat ttggttaaat tttgacatga tagagagtgt agtacagaaa caaatagctt  25200
taacagttca tcacctgtgc atttctgcca ggtaaccacc ccagcagaat attagatctc  25260
aaagagctta aggtcctgct taagaagaga agccaaaggg gagataggtc atcttataat  25320
ggttagggca catgactaga aaatgttgaa ctttacctga ccattaaaac ggcaattatg  25380
acaataatgg caacactggt agtttcctaa ttaaaattct gctgaaggaa attcatggat  25440
gaaaaatcca ggcattactt aagtttgtgt gagtagactg tgtatatcca gatggaatgt  25500
aaaaattaaa aatgattact gagccatcat taatagtcac tgacactaag ttgtcaccca  25560
cagttgatta caaaataaga gaaaccttgt tggaattctg ataggactta gaagactagg  25620
tttcattctc agatgttatg tgtatatcaa attgtgaccg attcctagaa agctggttag  25680
caggagaaca tcaaaatgag atagaaagag cactggggtt tagaaatcag aatctcacta  25740
ccctttgtgc ccagatcttg ctatttgacc taaaggaagt cattttaact cttaaaaagt  25800
ggaggttaga caagatgaca agatttcttc tatttcaaaa attccctagc acatgattgc  25860
tgaaaatatt tactacatat ttttaatcta aaacttttat ggaattttag atttggtgtt  25920
tgacatgttt ttcagacaat ggagtcaatg aatggtggaa aactctattc caatgcatat  25980
ctgaatgatt tagcaggctg catcaaaaca ttgcgctact gtgcaggttg ggctgacaag  26040
atccagggcc gtacaatacc aattggtaag tatctttgag aaaccactaa tggtgaggat  26100
aggagcgagg agtttactat agagctgaat aatttcaaac tctccctttt aaagatgtca  26160
```

```
accaaataag gcaaaattat tttcctcttg actttgagac aacacagttt tcaacttaga  26220
agttctatta aaattcataa aaggtctttt aaagttgttt cagcataatc atgaagataa  26280
cattatagat attttagaaa atgtcaaagt aagaacattc ctttggcagt aattactgat  26340
ctgaggcaat tgcctctcta aggtcccaaa ctttttaaag ctgacctctg aaattattta  26400
tttgggtttt attccaatac tgacatttat atcctttctg taatgtaatt atttaagcct  26460
ctttacatgt tccagtataa gtcagttatg gtcatctgtg cctggtcaaa ctcagtgtag  26520
ttagaccaga ctaatcaaac aagccagttc acacggactc gtttcaaata tcttcaaagc  26580
aagatgggac tgtgtttgca gcctaagtta agggtttgtg tgtgtgaatc tgtacgtatg  26640
tgttatttta gtggggtatg cacataatgg agtagaaata ctaaagatat ttcatgtgaa  26700
acatgaaaac acacacattt aggaaacagt atgggtggaa tttaattcag gcaaacctat  26760
gaactttagg aatacaatac cctccaggac tggccctgat gtgcacttcc aatccaattg  26820
gagcatgcag gaggtcagaa gtgatagcag aaagttgaga ggagagtaag acctcggtgg  26880
tactaagaaa tgtggctact ttagaactgt cctactttac tccgggacaa aatgggagaa  26940
gtcacttaaa acacaaatag atcttgatga agagagtcct tgctgaaacc aggaagcttc  27000
tgtgggaact agaacagaat tgaatgtaaa gcataatgta tctctctgga tgaccacatt  27060
aaacttcggg gcacataaat tggtcaaatt tagattgaaa ataaatgtct tatactcctg  27120
tcatttctt catgtattta gagaatttgc tattattgtt tggtaggcaa ataaaataca  27180
ttttagaaca agtcagtagg aaaggcttat tactcatagg gagattttct ttttaattct  27240
actgttttta attttactat ttctaaaaat tatattataa cttttaaaaa gaattctctt  27300
attggtagaa ctttgagcta ccagaaacaa attggaatgt ggttcttctc ttcgccagag  27360
acctcctact tcctttctcg tcccttttt ataacactta gagaataaag ataattttca  27420
aatcaggcct cctagaagat gaaaggtgga attaattatc tttcagattt ttgccaattt  27480
tgcctctttg atttcaccta actcaatttt atggttccta tcatttcgaa ttactatttt  27540
agggcttcac ttaccatttt gggaatagtt ggagatatag atggtctcga tctcttgacc  27600
tcgtgatctg cctgcctcgg cctcccaaag tgctgggatt acaggcgtga gccaccacac  27660
ctggccagat atatgttttt aaaattattg tctacacctt tctctcacat caccaaccac  27720
cattttgtga atgtcaaata catttgttta tatatgattg tgtgtgtttt atttttcaga  27780
tggaaatttt tttacatata caagacatga acctattggt gtatgtggcc aaatcattcc  27840
tgtaagcttt tctcctatat aattctcaat tttaaaaaga agagttctta ttctatctaa  27900
tgatgaagct ttctctaaaa cagatggatg cttatgtatt tgttaaatgt ggagtaaatg  27960
taagatttgt tgaacttggt ctccctgtga ctaaacttct tgcatatgaa ttaggtagtc  28020
cgaaaaccta tctatattct ggcatatctc ttgagaatgt tttaatacta catcatccat  28080
aaatgttaac cctttactct atgggttgtt ttattaaaag ttgtattatg tactctttat  28140
aagagccaag ctttacatgt atatggcaag gtgctctcca ctgcacatct gcaggatagc  28200
attttggtgg aatgtagtgg ggcctactat tctccaacgc actttctcat tgagacatct  28260
catcatgcag aacagtagct cccagagtgt tcaactcatg acacacattt tttaatcaaa  28320
atggaaaaaa gaataccaga ggcatttgaa gcactgcatg gaatatattt tacctttaga  28380
taagaggctc agatcctcca tattactctt agaggaaagt agccttttta agaggattgt  28440
gaagattttt taagcccaac aaacaggaca ctatctaaat gattttattt taactgacat  28500
```

-continued gctttaaaag gccaaacaaa aaaatggtag cgaagtcctt atgtgaagaa atggtcaaga 28560
cttatctttg gctccaatga gattgaaata tattcatatc aatattttag tgaaattgct 28620
tattaattca aaagtcccaa taaatcgata aaaactatat aattatgaac actgataata 28680
gctgatatgt actacttgtc tatgctagac cagtcattgt gttgagcccc tggccctctt 28740
tcttggttaa tgctcaagac agccttctga ggcagagagg actattatca gcactcacag 28800
attatgaaat cagatacaga gagcacgtaa cctgtgtgag ttcacatggc tggtcagtga 28860
ttgagctgag atttgaaccc aagtacttgg cctctggacc ctggacatct ttgtctttag 28920
caaggtattt ttcctggaaa taaaagctac taaataatat tattgggtaa ataattacaa 28980
taaatgactt atggagaagg agagtaatca tcctttttaa acatttttag ataacttaca 29040
gtgtgctcca taataagcca aaccatgcag tgattttttt tttcctggta gaaaaagaac 29100
tcaacagtac ttgattaaat tttgaggttc tctcctattt ccttctcata tctcatatct 29160
ggtttattca gagcgtttta gcatttacta gttgctttta gcaatgaagt ataatatgcc 29220
agatgatttc acaaaactac gcaattatta cataacatct acaggggggtg tataatatgg 29280
aagttggatt agcaaatatg ccttttgcaa tacaaagaat ctattgttac atattgcttt 29340
ctagtggaat ttcccgttgg ttatgctcat ttggaagata gggcctgcac tgagctgtgg 29400
aaacacagtg gttgtcaaac cagcagagca aactcctctc actgctctcc acgtggcatc 29460
tttaataaaa gaggtaagtc tcccgaaatc aaaatatgct caagaactca agaatcctaa 29520
attacaatag gaagacctca tttgttgcta ctataaagta cattatttac agatggctcc 29580
tgtccagtgg ggggaataca tttagcatga cggctggctg caatttctgg cagtcacccc 29640
aaattcatct ctgcccaaat gcagacagga agccaaacac aaaggtttgg tgtcaaacag 29700
tcaacttggg atcacatttt tgcttctttg tccaactctc atgaacataa attcatgttg 29760
aaattaatgt agcattcttt caaatgttga aacattaagt tggtttgtac ctgccactga 29820
tggcctagtg ttttctgcaa aattgtgtaa actaatctat gtaaggttga aagggcctct 29880
atgccaatat gcttgtttgt aatattgggc cacattattt ccaaacactt ttcaatctac 29940
tcatgagtgg atatgtttat attcagtttt ctattatgag ttcctctgca tttatcttcc 30000
tgttcaaaaa cagtaaaaga acatgtaaaa cattttcatc agctatctag attgtgttaa 30060
tatacttgca aacaattcat tgtccttttt tcttcatctt accaaatctt aaaaaataaa 30120
tgttaatcac tagaaactta aagttacaaa actgaactta tcttttaaag atattattta 30180
ttgaaattaa aaacagggaa aagagatgtc aaaatgaaac atttcgatgc aaataacatg 30240
aaattgtaat gtgcccaact cagttcccat gccttcacct gaattcttta atgaagattg 30300
aaatcaacct gtgatgttga atcatgaatg ggatgacagt atttacttaa caatttacta 30360
agtaatgcca atgggaattt gcaactcagc agttatgccc tcaacaatca acaacagcta 30420
ggaactaaaa aatgttagat cccttcagct tcttattttt gctgatggga ataataaaca 30480
tgttacttac tttctacata agtaacttac caaacacttt tttacataca atctttttga 30540
gttagcatta tgaaatttga aagagccatc actggagcaa tgattcatag agtatggact 30600
taccctgaca agaaattgtc ctttaataat gcaacccttg aagttattct cttatgtgtg 30660
cttagaaatg acataataag actaaagaat agagccagtt gggtgaatta tttttttcta 30720
gagcatctca taaggttggc attaagagac aatctcaatc ccctactctc ctccttttg 30780
aattaaattc ttatactgta acttttaaac tttttatctt ttaggcaggg tttcctcctg 30840
gagtagtgaa tattgttcct ggttatgggc ctacagcagg ggcagccatt tcttctcaca 30900

```
tggatataga caaagtagcc ttcacaggat caacagaggt aatattattt actcagggca  30960
aaagttaaga atgtctgcat tgccagctat gaagtatgtt ttatgtaact atttttgagc  31020
caacaatttt aaaacaaaaa ctctttttaa tgatttgtta cttattttag ccttcaaaca  31080
tatggataga atataagcag atgtagtttg aatgacatga tgcacctatt ttaaatcaga  31140
atgagagtaa actattttta gtatgttcat tactttctct gacgagaaat atggctgctg  31200
agaccttgtc atattattag gaagatttat aatagaaaat taggccatag tgatttgtat  31260
gaatgaatat gattttatcc tataggttat gaaaattaaa tagtagagtc tcaccctttg  31320
caccttattt ggggttgtct ttctcctgga cactgtgaaa gagagccaga aactcagctt  31380
ccctcagtgg tacctagact aacttttctg cctctctggc ttgaacttga ccatcctaaa  31440
ggttaaagaa aaagacccca accacaaagg agaagtggcg ggcaggaggg agagcagact  31500
agaaggtgaa gtttgggaaa atagatcccc atttattgat gatgttctat cctaagcaaa  31560
agaaagtggt ggaagcatac tgtaccatgc aaaaaaaatt attgagtcat tctattaaat  31620
tacgtgactt tgttagatgc tcagtgcaaa aatgttattc attggtacac agtatagaca  31680
gtgaagagtg agcttcactc catcttagaa agctgctgac aacaagagac caggcagggt  31740
gtgataaggt actaaggcat gtacaaaatg ctgtaaaaaa ggttcacaag aaggaatgat  31800
gatgtccaaa tgggtactag aactagctct gggttttgag gaattgttac ttttttaact  31860
tcctggaagt tgagaagcaa aaaagacatt ccagatagtg tggtgagcat aatttgatta  31920
ttttataatc ttaattattt actccagaat aaaggcaaat ttacatagca aaaagaaatg  31980
gtggaaaatc aaactttatt tttcttggtc tttttaaaat gaagtaaata aatatatata  32040
tgtcttcttt gtttttcaca gacgtagagt aaaaaaagtt tgcattctgc aactccctaa  32100
ttgagatagg gaaaagcaaa ccccacagtc aagatttatt gtagacagaa caagtgggaa  32160
tgttcaagat atggcaatac atttaaaaat ggtgacacca caggttgaaa tcataccaga  32220
ggaataaagg tgaaaattcc tcagcctaga attctagacc ctccccaata gggaatccat  32280
gtacctgttg aggtctgtcc aacccatggc cagggatggc tttgaatgta gcccgacaca  32340
ttttttttc attctcatca gctatcttta ctgttagtgt attttttgtg tggcccaaga  32400
caattcttct tcccatgtag cccagggaag ccaaaagatt gaacaaccct ggtctagatc  32460
ctatgcctac tccttctcca ggtcatctgg accaggagct actgtttgct gatctcatct  32520
tcagcatcag tttgtcttcg ctcatccatg atcccctata acattggggg agcactttac  32580
ctacttaaaa aaatccctgg agattaaaag tctagaaaat atcttggttt aaattctgac  32640
tctacccctc ctagcagtgt gtctttaaaa agttaagtag ccttactaaa tttgagtttc  32700
ttcatttgta aaatggagat gagatcaaat ttactgagtt gtacagaata caattaaatg  32760
agctaatgag tagtaaaaca tttatcaccc tactgagcgc tcagtacatg ccatatttcc  32820
tctttcctcc catacttttt aatttcgcac actagtttac acaatgtgag aaaaaagctt  32880
cctgtcccaa tatttctttt tctccatctc tgccactctg ccccatctct tcctgattat  32940
tccatgtatc ttttcattcc cccaggcttt tagttcatcc ttggccataa cctactctaa  33000
acttgctccc acacgttccc tctctggctt tctccttgcc tctacagtcc caggagcaga  33060
gcagcctaaa ttttaaaaca ccccatctga gttcccattg tccaccacat ataataacag  33120
tgcatgccta ttgccttatg tgtctctctc tcttgctgat tatcctcaaa gacagtctta  33180
ttcattgtta tctccagaaa ccatcacagt aagaaattct aaataagtat taaagaatta  33240
```

```
aatgtgatat cacactctgg ggactgtggt ggggtcgggg gaggggggag ggatagcatt  33300
gggagatata cctaatgcta gatgacacat tagtgggtgc agcgcaccag catggcacat  33360
gtatacatat gtaactaacc tgcacaatgt gcacatgtac cctaaaactt agagtataat  33420
taaaaaaaaa aaaatgaaaa aaaaaaaaaa aaagaattaa atgtgaataa cacgatttta  33480
ggagccacaa aacccatcct actttcaact cctgaaactt agttccatac tccctggaac  33540
ttctttctgg attttctttt agcttcacat ttgttgcttg gcagatatta aggaacttga  33600
taaatgtcat gaaagaggca aacaatagac tgtatccttt gtgttcattg tagcaaagac  33660
cctccattct aacaacactt taggcaaggt aagaattttt tttttttttt ttttttgaga  33720
ggagtcgtgc actgtcaccc aggctggagt gcagtggcgt gatcttggct caagctccac  33780
ctccgtggtt catgccattc tcctgcctca gcctcccgag tagctgggac tacaggcgcc  33840
caccaccacg cccagctaat tttttgtact tttagtagag ttggggtttc accgtgttag  33900
ccaggatggt ctcgatctct tgacctcatg atctgcccgc ctcagcctcc cagagtgctg  33960
ggattacagg cgtgagccac cgcaatatcc cattagattc atataaaata gaactctacc  34020
cacattatgc aagacataat aagctagacc attttcatgg gcatttgcta cttctgctcc  34080
acatggcaat gccacagtat catggaatac actgtttagc catagtctta atagttctta  34140
tcttttcttc attgcatact cctttgagaa aaatgataaa cgtttacttt tctccaaata  34200
agggaatgaa atcatgagac aaaaattaat gtctctttgt tttgacttta gctagacttt  34260
tgggaaaact caagcctttt atttgccatc taaacttgtg ctaagcaaaa gtgtagactt  34320
tctttctcat tcatacttct aaccattctt catcctagtt cttttgacgt ttgtagcttt  34380
tacaaaaata tatttgattt tattaccttc tccaaggcaa aagttatcta ctttaatgga  34440
gttacttccg taaacctaaa ttaaacaaat aaaaaaaatt cagaaagaat ttagagaaat  34500
caaagggtga caggtaagta aattttttat ctacaaaatt aaaaactcct taacatctta  34560
aatgaaaatt cagtttctga aagtggtcat aagaagtgtg ttatagaatg gcatataaga  34620
gaaatttcag acaggatttc cctagtgcaa atctcctttt aatttatttt ttattaatct  34680
tttaggggtt tgatttagaa acataaaata tttaaatagg aggaaaacat tagcatatta  34740
atgccctatt ctgtaattca cagtagcagt tagttcagta accacataaa atctaaacat  34800
acactcacga aacatctatt tctctcttgt tcagttggga tagaaacttt ttattaaaat  34860
ctgacatgca gagtaaaaaa aagaaaccta gaaaataaaa gaagcaaaat agtgaattgc  34920
ctttaaaaaa gaaaggcaaa gaacatgttg gtggattaag gctgccatac aaataataaa  34980
aaagaaataa ttgtagaacc agccaagttt ttagagatag aaaaaccaga aacaactata  35040
gtaaataatc ttgatgggaa gtgatccaca aaggaaaaaa taattgaaaa caaagtcttc  35100
ctctgaaaag ggcaaactag cattaaagaa gaaaccagaa ctgtaggatt ccagctaact  35160
gaagtagctg cacagatccc atttctttca tccagttcca ctgttcaaag gtgtgtgtgt  35220
tgggtgggaa gacagagaaa gaaagagata gagagacgac tgtcaatccg caattaaatg  35280
agccttctgt catagatact aatgaggaga ggtatgcagt gatacgttat tgttactgct  35340
accacagagt taacaatcta tttgggaaat gtatttctat acaaataata caatctggat  35400
cagactctga aggagacttc atgaggtttt ttgggagact agaaaaagaa atggtcctgt  35460
catttcttct agcatctgac ctagtgtcat cagagaagga tttaaggaga agctaagata  35520
tgagctggac ccctaagaaa aatagaactt gaaggcagtc caggttgggg tggacaaata  35580
atgagaagaa ggatgagatt caagaggtag tgaatatgtc agtttgactg gatagagtta  35640
```

```
tctggatgcc agaagaggga taaaaaatga aatagctaag ttgcgactgg gtcatgataa  35700
gtctgatcaa tctgtagaaa gatgatattc tgattaaaat taaaaataac ctccgtagcc  35760
atcaatatca cttatccgtg ttctatatct ctgctttctt gctgatgaaa aatcagcatt  35820
tttctgattc cttttatgtc tgtatgcttg gatgagggag ctttacatat ctaaaagtgc  35880
cagatcttta aaaatgccat ttgccagaga atcacttgaa cccgggaggc ggaggttgca  35940
gtgagccgag attgcgccac tgcactccag cccagtcgac agtgtgagac ttcgtctcaa  36000
aaaaaaaagc catttggtgt ttctcccaaa tgaaatttta ctgtggcaca aacatcacat  36060
aaatttagaa tgctaaagca acctgtgttc atgagagcag ggtaagcctc ctcctttgta  36120
atgctccctt tcaggttggc aagttgatca aagaagctgc cgggaaaagc aatctgaaga  36180
gggtgaccct ggagcttgga ggaaagagcc cttgcattgt gttagctgat gccgactgtg  36240
agtagaaacc actttgttaa cttttcgtcc ttcatcgttt ttggtgtctg ataatgccaa  36300
aagtgaactt gaactttaca aaaaaaaaaa aaaaaaaaaa aaagcatttg cttctaacat  36360
caaagtgtaa agagtccaaa attactcttg aaaatctctt aaatcatcct aaagttataa  36420
cacatagata atagacacaa tttcttcctc gtttagaata gattgctatt tcctcagctg  36480
aaccctagat gatgtaaaca ttttgcattt aaatgccatg gtgtattttt taaattccat  36540
atctgtgatt attagcattt cattgagcta atgagatact ccagaatggg acttggattg  36600
agaccaactg aggagacagc agtttcacat ttgccctctc ccttcactct gggtcataca  36660
ctcattaaat gaaatgatca gaagaaaatt atacctaata tttaaatatt ttttcctagc  36720
aagtatagtg gagtttatgt acattaaacc tacaaattg atataacccc actatataat  36780
attttaggtt cattctgatt atattaccaa gtagaatttc ccaattattt cctaaataga  36840
agttaattag cagaaatgca tggtcaaaca ttcttttttc tttcacaact gcattatctg  36900
ttagaggctg taaatacaaa tggttcatgg aattagccta tgttgctgtt ttgatcttaa  36960
ttgaagtatt ttagaacaca ctaccttatg aaatattcta taaacatgaa agatttctaa  37020
ttttactaag actgtctata aactgcttct gctacaactt aagcagatgt aattagttca  37080
caaaataaat aataatcata cccagttgct ataacattga attgaatctt cagcatttag  37140
aaaattaaaa tgcaaagaaa attttattct tgtttagagt ctactaagga agcaacctat  37200
ttcttccttt taatgcacat tttatcgcct aaaataaata agagtttata ggcacatatg  37260
aaataatacg gtatacttta gatagatttt gaaaatgtct ttgatggaat aaaatcataa  37320
ggtgagtgag tgattctgag tattagtgtt ttttgttact ttttagttgt ttttgtttta  37380
ttttgttttt ctttcccaca aagatcacat ttcctgttga gtagagtatt taagaatctt  37440
ttgaaattat ttaattcgat agacatgtca ggtttttttt attatctgtt taaaatctgg  37500
ggcctgaaag aaataatcac aatcatctaa ttatataatt ggagatattt atataaatca  37560
tttccaaaga gatttggtct catgatcaaa tctacattct tggtgatgtc catattaaag  37620
ttgtaatagt aaccactatt ttttcagatt ctgtatgttt ctattttttc catggtaaat  37680
gcaggatcag aaagattaat ttgccacctg gctggtagga ggtaaactat actgagccca  37740
tgtctgacta cacaactcat aatttttctt tatctccatg ttgcctctga gaaacatata  37800
aaatatataa tttttataaa atatatcttt aatgtgaatg tcttcttcgc agtggacaat  37860
gctgttgaat ttgcacacca tggggtattc taccaccagg gccagtgttg tatagccgca  37920
tccaggattt ttgtggaaga atcaatttat gatgagtttg ttcgaaggag tgttgagcgg  37980
```

```
gctaagaagt atatccttgg aaatcctctg accccaggag tcactcaagg ccctcaggta  38040
agtataaaat agaaaggata gcattttcag ggcacaggaa taaagtatcc tctttagacc  38100
tagattttat tgagtaagat tacttcccat ctgcacacct tcctaggtga caatgctgtg  38160
ccagtttggt gtttaaaagc aatctaactc ccagtgagaa tgaaatcatc ctgtttttgt  38220
gttgcccagt tttcatgtct agaaacagtt taccggccat gctgagaatt aaagacatga  38280
ggaaaaataa caaatgttct acatttttgg ctttcctcaa tctgcacacc tcttgattcc  38340
tatatacagt tctctgtcca ctttgaaatt cttatacatt cctaccattt tttcctcctg  38400
aatccttcat ctccacagcc atcccacagt tataaccagc actcccctaa atcctctgca  38460
agtcatcggt tactctgacc ccctaatcgt agcatggggt cctaaaatgt cctgagtttc  38520
ctttgcggca aacttcgtat ttcagttgtt aaagcccaat tattccccta ggcactcagt  38580
tttctttgta gactttatta tcagtaaagg tctctctctc tcttatccaa agatcatctt  38640
tccctcttcc ttgcatagtt ctctgttcat tgtttgttta agcttctgga tctttggttg  38700
tgaatttctt cctgcccttt gggtcttgtt ctagagcagt gattctaaac tggggcaatt  38760
ttgctcccct caccccgggg acatttggca atgtctaggg atattttaag ttgtcactac  38820
cttggtgaga agcggtggct ctacaggcat ctagtgagta gaggccagag atgctgctaa  38880
acatcttgca gtgaccagga cagccccatg acaaagaatt atctggccca aaatgccaac  38940
aggacaactg ccgagaaatc ctgctctgga gtctagacat taagcttaga ggctctgttc  39000
tttcacaata aaggttttac actgatgcgt gctgtcaatt tgaaaccaaa cgctattctt  39060
gactcattca ctaagccaaa agtaaattca attaactaaa agttagtgaa cgttgctatc  39120
agctaaaact tgagatgggt acctggcaat gccaaaaaga acaaagagga cttgatcccg  39180
gacctcatgg agtttacagt ccaagtaagt tggacagtct tggattttcc tgttcatctc  39240
aagacatcca agtaggaaaa tcttaggact taggcagtgt aacatattga aatctaaagg  39300
ccctaaaata agcggcaagt gaggtaatac tttgttttat cttaatccca ttatattttg  39360
tatttgtctt tgagtttaat gagtacttaa aagtagttgc ccttttttc atatttggta  39420
tatggatgcc aagagatata ttcaaatcag ttttgacttg gtctcccatt tcaaaaaaga  39480
atggaattct atgttttttt gttgtgatta tttatctatc taactaaaag tgaagcactt  39540
ttcttatttt gttgatggat tgatggatga ttgattgata gatctgaaga gaggagagaa  39600
tacctaagat acctaatgcc taattgttgg gcagtacttt cctccattag gacatcttca  39660
caattcaacc aaagactcaa aaattgagct ggaatacctc attgatttta agataaggaa  39720
gttaaaatag acttaaaaat tcctatttgt aagattctaa agtaaataat ccagtgatct  39780
agaatttagt ttctataaat gaatagaatc cagtgatctg attaatataa gaatttagtt  39840
tctataagtg aatagatttt tatcacaagt tccattgagt cagtaggata agtaggtatg  39900
ttagaatttg gagaaacaaa agactaaaaa gccctgggct cctttaccat taaatattca  39960
tctattgtta ggagaaaaaa cttacgcaaa ggggatactc actcactaag ctttagccta  40020
ttgcctcatc caggggtggt tgagtgaact gaggctttta aatacaatga tggaatcttc  40080
ctcattaaat ataacatcaa aaaggttata gaaaaaataa tggtcaaaac gatttgtttt  40140
aggggaaaaa attaaagttt aaaaaaattt gaacattaca aattatttgg gggttagagc  40200
aattacaaaa tatatatata tatatacttt gcatatttgt attatatctg tggattcatg  40260
tgtgtatctt tttcatattt caagtgattt tcctatttga ctttatagaa aaaatatata  40320
ttgtcttaaa cttggaaaaa ttagtatttt catttgaaac agaaattgtg atagccacat  40380
```

```
aaacgatact aaaattatca cagagtagca ccttataata gtgtggaaag atggactttg  40440
gagttacagt tatataggat ttaaactgga tttaaaatcc agcctccctg aaactattgt  40500
cttatgtgta gaatgtgcat agaaacctca atcttgaaga ataattctgc agtgcaattg  40560
gataatctat aaaatgtatc catcagagtg cttggtccac atgctcaaat gtctagtaaa  40620
taaataaaaa ttacatgctt ccatttatac ccatggtgac aattatcata cagatcaatt  40680
acttctatat ctattcattg cttttgttga tacatggttt ctgaataatt tgagaacatg  40740
taagtgcttt ttcccaattc atcttcttta acccattaag cctaaggaat caaagaattt  40800
acccattcaa acaccttaaa atgtttcctt tgagactgtt accatatcat gacctaccta  40860
atacatttca tagactagcc cataggccaa tggcccatca catgaaagag ccccagctac  40920
atcctagcat tattggacag tcccaggtgt ccagaaagaa ggtcaagttt atatatggtc  40980
agcctgatgc cttctgaaga aggtctgtat ttgtggtgaa tcaaaattag ccagacaaaa  41040
ctgaccagtc tctaagtaga gcctaatttt ttgtttgtag tcccaagctc caccacagtg  41100
ttcctcaatc tttcccgtgc ccggggattc agtagatctg aggtggggtc aaagaagcac  41160
atttggctac caagtgatgc cacaactgct ggttgtagga ccacattgtc ggtagcaagg  41220
cactgaaata caaaggcctg tagttttata agttagcgac catctaagtt ttccaacaaa  41280
taaggctttt cagccctttt ctccagtatg tatgcaggga tttgattggc actggttatt  41340
caacgtggtc acagacagga aaacatgact tgggaaatac atcttgaaat aaaaaccaga  41400
tatcatgatg ttgagggcat agtcagatta atatgttcca ataagacaga aagctttatg  41460
tggagtgaca tggacccttg actatttatt gagaaactag aataccttac ccaggcagaa  41520
tttatctcac cccacccctt agtctgctac tattcaacct atgtagtaat ttaaatattt  41580
cttcttaaca ctattttttt cttaatctgc tggaaatgaa ggaatatttt ccttctggga  41640
tattatatta aatattgcac taaagactgt tgagcaacat tgtaccaaat attgtgccaa  41700
attttagaaa atagtttcta gtttcaaata gtgcttaatc tagttagata tgggggctga  41760
gctgtattca gttagaaata actttatgga agctttttct tggctttgga agataaagaa  41820
gatttgcaga gtcagagaag agtaagagaa agtgaaacat aaaacttttc aagtagtggg  41880
aagttaaacc tacaagagct tccaccctcc aacccatctt agctcctaga tctcctgttt  41940
ttcctttaat ccttaacccc tgctacacct gagataggca gccctcaccg gttacttgga  42000
atccaagagt cacccagtta ttcaatgtca caaaatagaa attgagacaa aaattagccc  42060
cagatttcag tgcttgaaga ggtacgtgtt cctggtgttc acaaccagaa ctccaaactc  42120
atttattttc cttataaaaa tagtgtttaa ataaagacga tttaagttct gtaatacttg  42180
gcacatagtt agatgtggct catttaatga agcaggatgg tgacattcag gacaggccag  42240
aaattggaag cagatttact gactgcccca gtgggaccag aactgggaag ggtgcgcaga  42300
ctatggtcag aatgggatat ccaagggcat cggacaggtc agagtgggtg attcagaaat  42360
ggggagatca aacagaggct cgggagtctt ctaagaacag tcttaaagca tctgcttccc  42420
aacagatcta attaaactca gtatcaaagt tctgtttttc tcttttccct cctttcattt  42480
cagccgggac aatagtttcc aggtaaatgt atttagatta acaggcattt cttccagagt  42540
gaataaatga tgattgtcat ttatgtgttt tttatgtgtt tgcagtgctg aatgctttcc  42600
tatataacta taaaacaaat gttaaataca aatatctgtc ttcaagagat tttcccctaa  42660
aagtcatgag aagaaaatat atccaaagaa tgaatctgaa cctctgttag ctgtttcgat  42720
```

```
tcaatatttg gtttaattgc aatattttag cattttgaag cccttgttaa caggcccagc  42780

aatgtgttat ctttacaagt gactactttt tttcttttca tgtgatattt ttcaaataga  42840

ttgacaagga acaatatgat aaaatacttg acctcattga gagtgggaag aaagaagggg  42900

ccaaactgga atgtggagga ggcccgtggg ggaataaagg ctactttgtc cagcccacag  42960

tgttctctaa tgttacagat gagatgcgca ttgccaaaga ggaggtaaat ggcttcattc  43020

tgttctgttc tttttgttgc catgttttgt ctgtttgtgt gtatacaaag tgtcacttta  43080

aaattcccag ctctttggaa catctttccc tctaaacctt actctttatt ctgttcttga  43140

tagaggttta agttatttgt gatagatact aaaaagtagt aagggatcca tggggccagc  43200

cacaaatgtt cagccaacac agatctggat gcttaacaat tttcaggtgc tgccttcaca  43260

gctttaaaac aatggaaaag aatcctgtca tttgcagcaa caacctggaa aatttatgct  43320

ccatgaaata tgacaggcat aaaaagacaa ataccgcagg atctcacttt tatgtgggat  43380

ctcaaagagt agaactcata gaagcagaga ttggaatggt ggttaccagg ggcttggggg  43440

agtggaggat gagggttggg aaatgttggt caaaggattc aaactttcaa ttaggaggag  43500

taagttcaag agagctatcg taaatatcct gactgtaatt aataacaatg tattgtatac  43560

ttgaatattg ctaagagagt caattttaag tgttctcacc acaaaagaga taaatatata  43620

ggttctactt tctggttcca cctttgccct atagactctt tctatataac agccatccat  43680

gtatttgaaa acagcattca tcccctctat cactccctac cttctatgtg ctcttagtcc  43740

tatttgtttc agctgttaga cttcctgatt ttgtatattg cagttaagtg tttggtgagt  43800

gtatatatgt gtgtctgtat acatatataa tgtgtatata cattatatat atgctcacca  43860

agtatttaac tacaatatac aaaattagaa aaaaaatgag ctgtcattct tgcatatctt  43920

gattaatacc agataagacg tggaaaaaaa tcttcaatta aggaaacatt tattgtgttc  43980

ctataatata ttaatatata gtagaacagc tagcttgcta cttcaaagta ggagcctgga  44040

gctatgtgct gtgttcaatt aaaattatgt aaaatatgaa cacatttatt agagtagctg  44100

ctgtgtatat ggttcctatg ttcaaatagg attagattta taacgttaag attcacactc  44160

aacctctatt gaacagcagc ccctcccttc taacatttaa atcagtggtg aacaccagaa  44220

aactctttgt catttctgat ttttgtcttc cttcattcag atttcccaga aaattctggt  44280

aatttcagga atctttatct gatcttaata aatattttat tgaaatgcag gagcttaatt  44340

ttaaagagaa aatccagttg tctttctttt acctgaggct gagatacagg gtgaattgag  44400

tttgggctgc agtaaccagg aacttagtga aagcaaaaga gtactttacg ttagaataag  44460

caaattgtga tttttgtttt ctgtcctgca attatagcca ttaccaatga actcatgctt  44520

tgattagaat aggatggttt agaatgtata agctcttgca gtaaggaaca attctgtttg  44580

atatatttaa gttgcctaag attttgctac agagtagact aaaagttcgt gatgtttacc  44640

taacttggct aattatgaaa agtaattagt aactattcta ctgagtacag tagaatagtt  44700

aatattttac caatggcata caggtattta aagcattatt attatcaatc attgcctatt  44760

catttatcca gcagattatc attgcctatt catttatcca gtagattgct ttctgggact  44820

tgttactatg tgtagtgact tggaagataa gaaaaactag agagtgaatt taaaatattc  44880

ccaagtgaaa aagaaattct gaagttaatg atttgttgca caatcataag ttcttgaaag  44940

cttaattcca acatctagaa acttaatatt gccttaatta tttgtaccct ttcttcttcc  45000

aaaggaaatt taacacctga ccattatctg ttttcaccta ccatttttgc agttacctat  45060

ttggattctc acacataggt ttgagatgag aagaaaaatc ttaatcaatt taggatagcg  45120
```

```
tgtaggaaaa aaaatctacg atatcattta aaatatttca ttttaaccta ttatttttac  45180
ttatttattt cttgtggtat agatttttgg accagtgcag caaatcatga agtttaaatc  45240
tttagatgac gtgatcaaaa gagcaaacaa tactttctat ggcttatcag caggagtgtt  45300
taccaaagac attgataaag ccataacaat ctcctctgct ctgcaggcag gaacagtgtg  45360
gtaagtccaa cctaaggaat gtagcctttt cagtaataac cacattaaca gattactacc  45420
ttgaactttt tcagacttgg atttttcatt tggaattacc tatccttcta gaaaagcagt  45480
tgctgccttg aaaaacaaac aaaaggctgg gtgcggtggc tcatgcctgt aatcccagca  45540
ctttgggagg ctgaggtggg tggatcagct gactgaggtc aggagtttga gaccagcctg  45600
gccaacatgg tgaaacgcca tgtctactaa aaatacaaaa attagatggg tgtgatgcct  45660
gtaatcccag ctacatggag gatgaggcag gagaattgct tgagcctggg aggcggaggt  45720
tgcagtgagc cgagatcatg ccattgcact ctagcctcag caacaagagc aaaactccgt  45780
ctcaaaaaaa aaaaaaaaaa aaaaaagctg tattggaaga actttaggga ggatattttc  45840
tttaacttta tctagcttct tgaaattgct taccaaaaat attgtattga tgtttgatta  45900
atacaatata agaattgcca agtaatttct gagcacgtgg tactatgctg tatacaggga  45960
ggtaaaagag taagaacaat atttacttgg tacccttgtg tatgcagata ttcttatatc  46020
ggccttctta ctctaggatt attagagata attgaagtta tttttgaaag attgaatttt  46080
gaagataccc tccctctccc atttttgacc tagtttatat ctcttatttt tatactttaa  46140
tcaagaggat ataaacatga agtctgtgcc tctcaaactg ttgcattctg tactcagctg  46200
tcagtctcta gactatgtct ttggtcactt tggtcccatt agcctaattt tggcccctca  46260
gtcctggaaa aagcacaaga ttattttcct tcccaacact aagtcacacc tagatcagac  46320
ctatgcaata ttctctttct ttctttcttt ctttctttct ttctttcttt ctttctttct  46380
ttctttcttt ctttctttct ttctttcttc tttctttttct ttctttcttt ctttctttct  46440
ttctttcttt ctttcgtctc tctctctctc tttctctttc tctcttttct tttctttctt  46500
cttttttttt tttttttttt ttttttgag ctggagtctc actctgtcac ccaggctgga  46560
gtgcaatggt gcgatcttgg atcactgcaa cctctgcctc ctgggttcaa gtgattctcc  46620
tgcctcagcc tcccaactag ctgggactac aggcatgtac caccaagccc agctaatctt  46680
tgtattttgt ttttttcttt ttttagtaga gacagggttt caccatgttg gccggactgg  46740
tctcgaactc ctgacctcaa gtgatccatc cgccttggcc tcccaaggtg ctgggattac  46800
aggcctgagc caccatgctg gcctggacct atacaatatt ctaaggctgt ggttctcagc  46860
cctggctgtt cattagaatc atctcggggg ctttaaaaat gtataaactg atttggggca  46920
ggggagggta tacattaaca caaattatat cagtgtatag tttaaatttc tcctccaaag  46980
cccatgtggc aatttaaatg ccattgtaac agcaatagga agtgggccta atgggagact  47040
cttaaataaa attcagcaag ttcttcttga atagtcggta tagctagtga tgaatataga  47100
atttgcctat gataaaagca ttaataaaat tcagcatagt tactgtgtgt atgtatatta  47160
tcgccactta ctgaagatat ttataccaag tactacaaca agaatactat tcacgcaatc  47220
ttacgcatac cttgaaacaa tcctattaaa tattatcatc cccactttac acatgaggaa  47280
acgcttgcag aagacagata acattttgaa ctcaaagttt ttgccaagtg aacatttctc  47340
agttccctgt taattcacag taaaatagtt tcatttctag ttgacagtaa aatgagcaaa  47400
tttactctct gcacttttta acaaagacaa atttcagttt tgtattttcg actagcagaa  47460
```

-continued

```
tgttccatgc ttgtttgatg aagcttgtta tgacatcacc ccactgaggg tcttgggaat  47520
ccctgatcag gaatttcctc tattatgaaa aacagagggg accatcttgt tactacatat  47580
cctagaagat aataattttc tggcattgtc ccagacctaa tagctgcttg gtgttttcag  47640
gaaaattatt gaactccaga gttgcaggaa gtttactcat aatttcaaag tagtatttga  47700
ttttgcaatt taaagggcaa ttaaacaaag ctgagacaat actgcctttt gtaagtgtaa  47760
atttattaaa ggaattatcc ctccaggatg agagacatag ttaagaactt tatggtccag  47820
tgagaatgtg gaacttcggg aactgggata gtgttttaac aaagaaaaca tctgaatatt  47880
atctcaggat aaaagtaatg accaaacctt caaagtataa tacaatttat ctggaagcca  47940
ccctggtttt ttgtttgttt gtttggttgg ttttctaaat ttgttttgta gaggcaaggg  48000
tttgctatgt tgcccaggct ggtctcaaac tcttgggctc aagtgatcct cctgcctcag  48060
tctccagcta ctaacccagg ctctggaagc cacatttttg tccacttatt aaaatagcat  48120
gaagggagag aaaagtataa acataaatct cctttaaaaa gtgtttttct cttgcgtata  48180
atgagaatca ggtaaataat tagattttgc taacttttgg ccaccagcaa atttaaagct  48240
aaacaaattg tttatggtct gcaaaactgc attctaattt tccccatcta gatcttctat  48300
tgtaattttt tgttggattc taattactac tattcatgta attatgtttg tttatataag  48360
catctttaaa cactttatga aatatgacag ggaataaatt ataattaaac ccaactcctg  48420
ccaaggcctc tgtttaagca atttatttaa ccaattaatg ggaaaaaaaa ttaactgagt  48480
aatatgatac atattacaat tgcaaaagaa aattgattct agcctgttaa gtacagaaac  48540
atcaagagaa ttacaagctg atccatatat aagcagtaat gaatactgat ccaacaaatt  48600
ctagcttcta gcaaaccata tctttccccc tacagcatag tgactattct atcttttata  48660
aattcagact accacttctc agggacacaa tgtacgacca aaatggctat ccatatatat  48720
agttgcacta ttctatttgt ttctaggtag tgtgtatcca tatatgtctg cattctaatt  48780
tatagtgcta cttttttta tcaagatgag tatgttataa tgaaattaat ggagtttgta  48840
aggagctttc caaatttcta aaactgccaa aaaggatttt tttttcacac cttaagtatt  48900
gtctataatg cacttttctt ttccttcagg gtgaattgct atggcgtggt aagtgcccag  48960
tgccccttg gtggattcaa gatgtctgga aatggaagag aactgtaaga ttaacgttct  49020
attaagataa atatttattt ttatgaaaat gattttcatt cccagggaat taactcatag  49080
ttttcacctt acataaaacc tgcctctgtt ctttcctgga gattcatagc accaaatagc  49140
ttattaaatg tgggatgtac tccataagtg caaaaggtga ttgcagaaca gcaacataat  49200
ttactaaatt cctactatat tttagggact atattaagca acttacattg gtgattgtaa  49260
tactgcttgc ttttagaatt gcttgctata tatatgaatg taatccattt gggaaacatt  49320
tccagaaaag aggtggaaac tatgcattgg tgattgcaag aaaggtgcaa atgtaaacac  49380
tctagttatt tgaataaacc atttaaataa gtaaattagg tgacttatgt aaaggaaatt  49440
tcagtgtaag aggaatgatt cccatttgtt gagatattat tgatgtagac tttaacattt  49500
tttattacca taagaagtta tttttagtat taaaacttaa acctaaaagg aaatttgagg  49560
aaaacatgtt ttatagtagt gactagatta agaatattta tatataaatg catttatgaa  49620
atttcaattg cttttgaaac tagggtatat agacttttta agtatgcaca tatatatgta  49680
aatacagaaa gtagtggcaa tatgcttagt tgattttgtt taggcaagtt tagtcatttt  49740
atttcttaaa actttttac atgtattaat gtaaacattt atgaagaaaa aagaaataga  49800
aaccttatag tatcaaacac agatcgtaaa cttgctcatt ttgtaattag gaagtgaaaa  49860
```

```
tgtgcctttc tcaatctcta aatgtattaa atggttgagt accgtactct aacaaatcag  49920
caaaattaca aggaaacaaa tatctctgaa gagtcagtga aatgggagaa ttataaaatg  49980
accagtctac tttctcaata tgctttcatt tattaagcac ttgctatgtg taaggtccta  50040
ggaaccccag agacatgaca ccatgttcca tgctctacat agctgtggtg gcaggacatg  50100
caaaataacc tacatacact atgaaataag tagtaataca ctgggattcc atatcctatg  50160
gaggtagaga agcaattaaa gtaccgagca aagtattgaa gaaaacctag acactaccag  50220
agtataagag tcaggatggc atctctctaa ccatcactat tttcatctgt cagacaaggc  50280
caaggattgt gagtgtggat aagagtggaa gaagaaaata gatcttttaa cctctattcc  50340
atgcttaaga ttctatagtt ctgaccccac tggaaatcca gtggttgaaa acttaatggc  50400
agtttataga gaagaaaact tctcctaaca gaagagatga aacttcctct agggcagaaa  50460
gcaagtgtag gatatcagtt agtagagaag agggctttct tgcatggaac attacatgtg  50520
gtatgttgag gggctagtga attttgttga ttggtgtgga tttatgggga tgaaaaatat  50580
gatttcagag taacatatga tacagattaa gaagtcctgc atttaagaaa tttgacttag  50640
attttattag tggagtagtg aaaagccatg gatatattta ggatgttgct gaagtagaac  50700
aaaaagttag cccatcaaaa atgcatggcg tagctgagaa aacattactg gagtctgacc  50760
agctgaattt gattcctaat tctgccactt gctagccatg caccccagtt caagctacct  50820
aacttctgag cctctacttt ctcatatttg gtggagatgt tcacattcct cttaagatgg  50880
aatgagagtt cttgtgggag ttaaatgaca tactgaatat taaatcccta gccacataac  50940
tgtcacaaag tgtaaattca acaaatgggt ttcttccttc cctagtttct tctctttcta  51000
ttactggaga atctcttggc aaaactaatt actttgtaca aaaagtaaga acaaaggtta  51060
gattactctg aagggcagtt ggttcgtttc tggcctggtt atctaacaac acatttcact  51120
gagaacatta aagataaaat aatcaaaagg aatgcaagac taaagtagac caaacatgtc  51180
aatttcgttg aacataattt ggtcagactt taaggtgaag gcataaagaa atcaaataag  51240
agaaggactg aaaacaggaa tcaaccatca gtaatttcct aaaaatctag aacatgagta  51300
tagataattt ctttcaaata caaaggaaaa agttgtgggt ttttttttt ttacttcaaa  51360
aattcaacta gagaatgcta cagttaaagt gtacctgaaa ccaaatttgg tgaatttaat  51420
aaccaagtca tttgctgcaa gatgttccaa gagttacaag ttattactca ggcgataacc  51480
tcaaatgact cccaagagtt aaattataaa ttttcctcaa caatagagag aattgatcag  51540
ttgagaacag agtcctcaaa gagcgaaaaa tggtgttatg cagaccccag tgtgtttgaa  51600
ggtgatacag agtatgcaaa tcttgatttt gcatctctga tcatagtgtt ggctctggga  51660
ttagttaaaa gacagaaatt cctccctttg tgtaactgta ctgtttcact taggttaacg  51720
taggtccttt aagactttgc tagtatgcca ttttaaactt gattggctct tagcccctcc  51780
caccatattt ttttcctcct gtcccataga aaagggagca aggaagtgta aactaatggt  51840
cgtatagtga gaacacaaat gaattttttt tcttgatatt taccaagtgt gttcagcaaa  51900
cagttcttct gtgcctactt aattagtgcc agtcttaatc ctgggtacag agaggaaatc  51960
agatgtaatg tggtactagt gccttttttt tttttacagt gtggaccctg gacaagaagc  52020
ataggttgat atcacttgca agtttattac caatgccaac tcaggcttca ctcgagacct  52080
gctaattcag aatcagtatt tgaataaggt cccaggtgat ttgtacattg aagattttag  52140
aagtatacaa acagtaactc acagacatag taagatgaag agaaatccaa acagatgttt  52200
```

```
ggggctatgt cgtagatata gtataggcat aggaatccta aggagcagga catatttcag  52260
cctgaatatg acaaaaatcc cacttattac tctcctgaga gcttcaagtg cctatatgac  52320
ccaaaataca atggaaagcc tattggcgaa agtcatgggt tgattgatct aaccctgaga  52380
taaaatactt attaaaatat tatcttttaa tgggtttcag acaactgagg ctaagccctt  52440
taattacttt aaggaccatg ctcactgaag cttttaaaag gtattttcaa aagcttaatt  52500
gcccaagaaa ataatcagtg taagagtatt aggttaccca gcagaaaatg atgtcttcta  52560
catacctgtc tacatcacaa gaagggaggg gtaaaaaagg atcaagatct tattcttctg  52620
taagcctaca tgtgcatgag tgttatgatt ttgagactac tcttatatac atgtaatttg  52680
atcctcttat caaaacaata tagagaataa ctgagcccaa tctttttagt catctcttca  52740
acaaggggta aatcagtcag tttctaaaac tggtgggagg tctccataaa cctgataaca  52800
agatcccaaa atccaaactg attgactgag ttaattcctg atcatttggg ttgaacttaa  52860
gagttataca agaaaatggt aggggacgag gaggttgtat aaaggggaaa aaacaacaac  52920
tgcaaaaagc ccaagagcct gaatttagac caatctatca tcttcctcct cttaaaaaga  52980
aaacaattta aaagttttaa ataaaaaata aaggtcatgt ttttgttttg ccaagaatca  53040
aaagattttg ctgaaactac tgctgcaaaa tattttgttt caagccatct tagggcacct  53100
cagactaaaa atgaaaccat gatcaatttc tatcccctta ccacttctat gacaatcaca  53160
catggtaaat acaagctctg ctctagtact acaataaaac tgtagaacta gagtagacct  53220
tgtagtgatc atatattact acttctcctc ttgtcctatg tccatcttat ttcaatctaa  53280
actagaaatg acaaaattct tgttgggtcg aattgtcttt tgagtagttt tagagctttt  53340
tgttttcatt tctccaagat gatcttgttg catctgcagt tcgagttttt aaaatcaagt  53400
agaataatgt caaaagggga caatttatgt gagaaatcaa ctgacagtac atgattattt  53460
aaaatgaaag ttttaaagaa aattttcccc acaagggaat ctgtgtaaga ccagaaatct  53520
tatgattggc tagctactat ataaaatgct ctgtacacaa gaaatatttt ctattgtccc  53580
tagccagtaa aacaagaaca aactcgtacc aaacatgaac tacagtatat ttatactgct  53640
gtgctaaatg gtgtttgtgg gtatgttttt cttctctcta ggggagagta cggtttccat  53700
gaatatacag aggtcaaaac agtcacagtg aaaatctctc agaagaactc ataaagaaaa  53760
tacaagagtg gagagaagct cttcaatagc taagcatctc cttacagtca ctaatatagt  53820
agattttaaa gacaaaattt ttcttttctt gattttttta aacataagct aaatcatatt  53880
agtattaata ctacccatag aaaacttgac atgtagcttc ttctgaaaga attatttgcc  53940
ttctgaaatg tgacccccaa gtcctatcct aaataaaaaa agacaaattc ggatgtatga  54000
tctctctagc tttgtcatag ttatgtgatt ttcctttgta gctacttttg caggataata  54060
attttataga aaaggaacag ttgcatttag cttctttccc ttagtgactc ttgaagtact  54120
taacatacac gttaactgca gagtaaattg ctctgttccc agtagttata aagtccttgg  54180
actgttttga aaagtttcct aggatgtcat gtctgcttgt caaaagaaat aatccctgta  54240
atatttagct gtaaactgaa tataaagctt aataaaaaca accttgcatg attcttgtta  54300
cttttgaatt tttttaagta caagttttgg ttacagtgat ttcttcttgt cacttaaaaa  54360
cagtgttaaa ctgagcataa aggtacattt aaaagtaaaa gtctaatcca cctattctca  54420
aataggtaaa gaaacatgct gtattttcca aaagaattct caaaatcagt ggattttatc  54480
tgaaatagat ggcctcagtc cttcagtaag caattattga gttcctacaa agttttgggt  54540
atgtgttaag tgttgtagaa aagaggtgaa taatgaatgg tccattatct gaagatcttt  54600
```

```
aatttagtgg ttaataaaga cacaatccct gcaccacaga aaggaggggt cataaaaaaa  54660

atgaggattt tagaaacttg tagtgacttg cagaagtggt catgatgaag gctaactgag  54720

ggaatcagga atggcctcag gtaggaaatt tgactgaata taaaccttaa taatgggcaa  54780

atttgcaatg aataaagggg aaagaggttc tacaaaattt atcaggacat gttccattga  54840

aaaaacattc ggaaaaattc tatacaatat attttcctct cttggaattt cagattgcac  54900

atcggcagca tattataggt ttcgagaagt cctgcaacct tcttagtttt aatagagccc  54960

cccctttttt tttccaaatt agcagagact ttgtctcctc tccctcacct cctcagttac  55020

caccaattaa cattaagaaa cccatgctgg gctgaataca gtggctcact cctgtaatcc  55080

tagcactttg ggaggccaca gcaggtggat ctgttgagcc caggagtttg agaccagcct  55140

gggcaatggg caaaatccca cctttattta aaaaaaaaaa ttagccaggc ataggggcac  55200

aaacctgtgg tcccatctac atgagaggct gaggcaggag gatggcttga acctgggagg  55260

tcgaggctgc agtgagccat gatcatacta ctgcactcta gcctgggtga cagagtggga  55320

ccctgtttca aaaataaaaa taaaaataaa aacccttgct gtcctatgca atgagggaac  55380

ccttagagtt ctaaggagag atctgggaat caaaagagag cagctgaaaa aaatgtcctc  55440

cacatgaaac tacaccaagc t                                           55461
```

<210> SEQ ID NO 7
<211> LENGTH: 466
<212> TYPE: PRT
<213> ORGANISM: Homo sapiens
<220> FEATURE:
<223> OTHER INFORMATION: vimentin (VIM), epidiymis luminal protein 113
(HEL113), CTRCT30

<400> SEQUENCE: 7

```
Met Ser Thr Arg Ser Val Ser Ser Ser Ser Tyr Arg Arg Met Phe Gly
1               5                   10                  15

Gly Pro Gly Thr Ala Ser Arg Pro Ser Ser Ser Arg Ser Tyr Val Thr
            20                  25                  30

Thr Ser Thr Arg Thr Tyr Ser Leu Gly Ser Ala Leu Arg Pro Ser Thr
        35                  40                  45

Ser Arg Ser Leu Tyr Ala Ser Ser Pro Gly Gly Val Tyr Ala Thr Arg
    50                  55                  60

Ser Ser Ala Val Arg Leu Arg Ser Ser Val Pro Gly Val Arg Leu Leu
65                  70                  75                  80

Gln Asp Ser Val Asp Phe Ser Leu Ala Asp Ala Ile Asn Thr Glu Phe
                85                  90                  95

Lys Asn Thr Arg Thr Asn Glu Lys Val Glu Leu Gln Glu Leu Asn Asp
            100                 105                 110

Arg Phe Ala Asn Tyr Ile Asp Lys Val Arg Phe Leu Glu Gln Gln Asn
        115                 120                 125

Lys Ile Leu Leu Ala Glu Leu Glu Gln Leu Lys Gly Gln Gly Lys Ser
    130                 135                 140

Arg Leu Gly Asp Leu Tyr Glu Glu Glu Met Arg Glu Leu Arg Arg Gln
145                 150                 155                 160

Val Asp Gln Leu Thr Asn Asp Lys Ala Arg Val Glu Val Glu Arg Asp
                165                 170                 175

Asn Leu Ala Glu Asp Ile Met Arg Leu Arg Glu Lys Leu Gln Glu Glu
            180                 185                 190

Met Leu Gln Arg Glu Glu Ala Glu Asn Thr Leu Gln Ser Phe Arg Gln
```

```
        195                 200                 205

Asp Val Asp Asn Ala Ser Leu Ala Arg Leu Asp Leu Glu Arg Lys Val
    210                 215                 220

Glu Ser Leu Gln Glu Glu Ile Ala Phe Leu Lys Lys Leu His Glu Glu
225                 230                 235                 240

Glu Ile Gln Glu Leu Gln Ala Gln Ile Gln Glu Gln His Val Gln Ile
                245                 250                 255

Asp Val Asp Val Ser Lys Pro Asp Leu Thr Ala Ala Leu Arg Asp Val
            260                 265                 270

Arg Gln Gln Tyr Glu Ser Val Ala Ala Lys Asn Leu Gln Glu Ala Glu
        275                 280                 285

Glu Trp Tyr Lys Ser Lys Phe Ala Asp Leu Ser Glu Ala Ala Asn Arg
    290                 295                 300

Asn Asn Asp Ala Leu Arg Gln Ala Lys Gln Glu Ser Thr Glu Tyr Arg
305                 310                 315                 320

Arg Gln Val Gln Ser Leu Thr Cys Glu Val Asp Ala Leu Lys Gly Thr
                325                 330                 335

Asn Glu Ser Leu Glu Arg Gln Met Arg Glu Met Glu Glu Asn Phe Ala
            340                 345                 350

Val Glu Ala Ala Asn Tyr Gln Asp Thr Ile Gly Arg Leu Gln Asp Glu
        355                 360                 365

Ile Gln Asn Met Lys Glu Glu Met Ala Arg His Leu Arg Glu Tyr Gln
    370                 375                 380

Asp Leu Leu Asn Val Lys Met Ala Leu Asp Ile Glu Ile Ala Thr Tyr
385                 390                 395                 400

Arg Lys Leu Leu Glu Gly Glu Glu Ser Arg Ile Ser Leu Pro Leu Pro
                405                 410                 415

Asn Phe Ser Ser Leu Asn Leu Arg Glu Thr Asn Leu Asp Ser Leu Pro
            420                 425                 430

Leu Val Asp Thr His Ser Lys Arg Thr Leu Leu Ile Lys Thr Val Glu
        435                 440                 445

Thr Arg Asp Gly Gln Val Ile Asn Glu Thr Ser Gln His His Asp Asp
    450                 455                 460

Leu Glu
465


<210> SEQ ID NO 8
<211> LENGTH: 2151
<212> TYPE: DNA
<213> ORGANISM: Homo sapiens
<220> FEATURE:
<223> OTHER INFORMATION: vimentin (VIM), epidiymis luminal protein 113
      (HEL113), CTRCT30

<400> SEQUENCE: 8

gcctctccaa aggctgcaga agtttcttgc taacaaaaag tccgcacatt cgagcaaaga      60

caggctttag cgagttatta aaaacttagg ggcgctcttg tcccccacag ggcccgaccg     120

cacacagcaa ggcgatggcc cagctgtaag ttggtagcac tgagaactag cagcgcgcgc     180

ggagcccgct gagacttgaa tcaatctggt ctaacggttt cccctaaacc gctaggagcc     240

ctcaatcggc gggacagcag ggcgcgtcct ctgccactct cgctccgagg tccccgcgcc     300

agagacgcag ccgcgctccc accacccaca cccaccgcgc cctcgttcgc ctcttctccg     360

ggagccagtc cgcgccaccg ccgccgccca ggccatcgcc accctccgca gccatgtcca     420

ccaggtccgt gtcctcgtcc tcctaccgca ggatgttcgg cggcccgggc accgcgagcc     480
```

```
ggccgagctc cagccggagc tacgtgacta cgtccacccg cacctacagc ctgggcagcg    540

cgctgcgccc cagcaccagc cgcagcctct acgcctcgtc cccgggcggc gtgtatgcca    600

cgcgctcctc tgccgtgcgc ctgcggagca gcgtgcccgg ggtgcggctc ctgcaggact    660

cggtggactt ctcgctggcc gacgccatca acaccgagtt caagaacacc cgcaccaacg    720

agaaggtgga gctgcaggag ctgaatgacc gcttcgccaa ctacatcgac aaggtgcgct    780

tcctggagca gcagaataag atcctgctgg ccgagctcga gcagctcaag ggccaaggca    840

agtcgcgcct gggggacctc tacgaggagg agatgcggga gctgcgccgg caggtggacc    900

agctaaccaa cgacaaagcc cgcgtcgagg tggagcgcga caacctggcc gaggacatca    960

tgcgcctccg ggagaaattg caggaggaga tgcttcagag agaggaagcc gaaaacaccc   1020

tgcaatcttt cagacaggat gttgacaatg cgtctctggc acgtcttgac cttgaacgca   1080

aagtggaatc tttgcaagaa gagattgcct ttttgaagaa actccacgaa gaggaaatcc   1140

aggagctgca ggctcagatt caggaacagc atgtccaaat cgatgtggat gtttccaagc   1200

ctgacctcac ggctgccctg cgtgacgtac gtcagcaata tgaaagtgtg gctgccaaga   1260

acctgcagga ggcagaagaa tggtacaaat ccaagtttgc tgacctctct gaggctgcca   1320

accggaacaa tgacgccctg cgccaggcaa agcaggagtc cactgagtac cggagacagg   1380

tgcagtccct cacctgtgaa gtggatgccc ttaaaggaac caatgagtcc ctggaacgcc   1440

agatgcgtga aatggaagag aactttgccg ttgaagctgc taactaccaa gacactattg   1500

gccgcctgca ggatgagatt cagaatatga aggaggaaat ggctcgtcac cttcgtgaat   1560

accaagacct gctcaatgtt aagatggccc ttgacattga gattgccacc tacaggaagc   1620

tgctggaagg cgaggagagc aggatttctc tgcctcttcc aaacttttcc tccctgaacc   1680

tgagggaaac taatctggat tcactccctc tggttgatac ccactcaaaa aggacacttc   1740

tgattaagac ggttgaaact agagatggac aggttatcaa cgaaacttct cagcatcacg   1800

atgaccttga ataaaaattg cacacactca gtgcagcaat atattaccag caagaataaa   1860

aaagaaatcc atatcttaaa gaaacagctt tcaagtgcct ttctgcagtt tttcaggagc   1920

gcaagataga tttggaatag gaataagctc tagttcttaa caaccgacac tcctacaaga   1980

tttagaaaaa agtttacaac ataatctagt ttacagaaaa atcttgtgct agaatacttt   2040

ttaaaaggta ttttgaatac cattaaaact gctttttttt ttccagcaag tatccaacca   2100

acttggttct gcttcaataa atctttggaa aaactcaaaa aaaaaaaaaa a            2151
```

<210> SEQ ID NO 9
<211> LENGTH: 781
<212> TYPE: PRT
<213> ORGANISM: Homo sapiens
<220> FEATURE:
<223> OTHER INFORMATION: beta-catenin (CTNNB), catenin beta-1 (CTNNB1), cadherin-associated protein, armadillo homolog, MRD19

<400> SEQUENCE: 9

```
Met Ala Thr Gln Ala Asp Leu Met Glu Leu Asp Met Ala Met Glu Pro
1               5                   10                  15

Asp Arg Lys Ala Ala Val Ser His Trp Gln Gln Gln Ser Tyr Leu Asp
            20                  25                  30

Ser Gly Ile His Ser Gly Ala Thr Thr Thr Ala Pro Ser Leu Ser Gly
        35                  40                  45

Lys Gly Asn Pro Glu Glu Glu Asp Val Asp Thr Ser Gln Val Leu Tyr
    50                  55                  60
```

```
Glu Trp Glu Gln Gly Phe Ser Gln Ser Phe Thr Gln Glu Gln Val Ala
65                  70                  75                  80

Asp Ile Asp Gly Gln Tyr Ala Met Thr Arg Ala Gln Arg Val Arg Ala
                85                  90                  95

Ala Met Phe Pro Glu Thr Leu Asp Glu Gly Met Gln Ile Pro Ser Thr
            100                 105                 110

Gln Phe Asp Ala Ala His Pro Thr Asn Val Gln Arg Leu Ala Glu Pro
        115                 120                 125

Ser Gln Met Leu Lys His Ala Val Val Asn Leu Ile Asn Tyr Gln Asp
    130                 135                 140

Asp Ala Glu Leu Ala Thr Arg Ala Ile Pro Glu Leu Thr Lys Leu Leu
145                 150                 155                 160

Asn Asp Glu Asp Gln Val Val Val Asn Lys Ala Ala Val Met Val His
                165                 170                 175

Gln Leu Ser Lys Lys Glu Ala Ser Arg His Ala Ile Met Arg Ser Pro
            180                 185                 190

Gln Met Val Ser Ala Ile Val Arg Thr Met Gln Asn Thr Asn Asp Val
        195                 200                 205

Glu Thr Ala Arg Cys Thr Ala Gly Thr Leu His Asn Leu Ser His His
    210                 215                 220

Arg Glu Gly Leu Leu Ala Ile Phe Lys Ser Gly Gly Ile Pro Ala Leu
225                 230                 235                 240

Val Lys Met Leu Gly Ser Pro Val Asp Ser Val Leu Phe Tyr Ala Ile
                245                 250                 255

Thr Thr Leu His Asn Leu Leu Leu His Gln Glu Gly Ala Lys Met Ala
            260                 265                 270

Val Arg Leu Ala Gly Gly Leu Gln Lys Met Val Ala Leu Leu Asn Lys
        275                 280                 285

Thr Asn Val Lys Phe Leu Ala Ile Thr Thr Asp Cys Leu Gln Ile Leu
    290                 295                 300

Ala Tyr Gly Asn Gln Glu Ser Lys Leu Ile Ile Leu Ala Ser Gly Gly
305                 310                 315                 320

Pro Gln Ala Leu Val Asn Ile Met Arg Thr Tyr Thr Tyr Glu Lys Leu
                325                 330                 335

Leu Trp Thr Thr Ser Arg Val Leu Lys Val Leu Ser Val Cys Ser Ser
            340                 345                 350

Asn Lys Pro Ala Ile Val Glu Ala Gly Gly Met Gln Ala Leu Gly Leu
        355                 360                 365

His Leu Thr Asp Pro Ser Gln Arg Leu Val Gln Asn Cys Leu Trp Thr
    370                 375                 380

Leu Arg Asn Leu Ser Asp Ala Ala Thr Lys Gln Glu Gly Met Glu Gly
385                 390                 395                 400

Leu Leu Gly Thr Leu Val Gln Leu Leu Gly Ser Asp Asp Ile Asn Val
                405                 410                 415

Val Thr Cys Ala Ala Gly Ile Leu Ser Asn Leu Thr Cys Asn Asn Tyr
            420                 425                 430

Lys Asn Lys Met Met Val Cys Gln Val Gly Gly Ile Glu Ala Leu Val
        435                 440                 445

Arg Thr Val Leu Arg Ala Gly Asp Arg Glu Asp Ile Thr Glu Pro Ala
    450                 455                 460

Ile Cys Ala Leu Arg His Leu Thr Ser Arg His Gln Glu Ala Glu Met
465                 470                 475                 480
```

```
Ala Gln Asn Ala Val Arg Leu His Tyr Gly Leu Pro Val Val Val Lys
                485                 490                 495

Leu Leu His Pro Pro Ser His Trp Pro Leu Ile Lys Ala Thr Val Gly
            500                 505                 510

Leu Ile Arg Asn Leu Ala Leu Cys Pro Ala Asn His Ala Pro Leu Arg
        515                 520                 525

Glu Gln Gly Ala Ile Pro Arg Leu Val Gln Leu Leu Val Arg Ala His
    530                 535                 540

Gln Asp Thr Gln Arg Arg Thr Ser Met Gly Gly Thr Gln Gln Gln Phe
545                 550                 555                 560

Val Glu Gly Val Arg Met Glu Glu Ile Val Glu Gly Cys Thr Gly Ala
                565                 570                 575

Leu His Ile Leu Ala Arg Asp Val His Asn Arg Ile Val Ile Arg Gly
            580                 585                 590

Leu Asn Thr Ile Pro Leu Phe Val Gln Leu Leu Tyr Ser Pro Ile Glu
        595                 600                 605

Asn Ile Gln Arg Val Ala Ala Gly Val Leu Cys Glu Leu Ala Gln Asp
    610                 615                 620

Lys Glu Ala Ala Glu Ala Ile Glu Ala Glu Gly Ala Thr Ala Pro Leu
625                 630                 635                 640

Thr Glu Leu Leu His Ser Arg Asn Glu Gly Val Ala Thr Tyr Ala Ala
                645                 650                 655

Ala Val Leu Phe Arg Met Ser Glu Asp Lys Pro Gln Asp Tyr Lys Lys
            660                 665                 670

Arg Leu Ser Val Glu Leu Thr Ser Ser Leu Phe Arg Thr Glu Pro Met
        675                 680                 685

Ala Trp Asn Glu Thr Ala Asp Leu Gly Leu Asp Ile Gly Ala Gln Gly
    690                 695                 700

Glu Pro Leu Gly Tyr Arg Gln Asp Asp Pro Ser Tyr Arg Ser Phe His
705                 710                 715                 720

Ser Gly Gly Tyr Gly Gln Asp Ala Leu Gly Met Asp Pro Met Met Glu
                725                 730                 735

His Glu Met Gly Gly His His Pro Gly Ala Asp Tyr Pro Val Asp Gly
            740                 745                 750

Leu Pro Asp Leu Gly His Ala Gln Asp Leu Met Asp Gly Leu Pro Pro
        755                 760                 765

Gly Asp Ser Asn Gln Leu Ala Trp Phe Asp Thr Asp Leu
    770                 775                 780
```

<210> SEQ ID NO 10
<211> LENGTH: 3256
<212> TYPE: DNA
<213> ORGANISM: Homo sapiens
<220> FEATURE:
<223> OTHER INFORMATION: beta-catenin (CTNNB), catenin beta-1 (CTNNB1) transcript variant 3, cadherin-associated protein, armadillo homolog, MRD19

<400> SEQUENCE: 10

```
aggatacagc ggcttctgcg cgacttataa gagctccttg tgcggcgcca ttttaagcct     60

ctcggtctgt ggcagcagcg ttggcccggc cccgggagcg gagagcgagg ggaggcggag    120

acggaggaag gtctgaggag cagcttcagt ccccgccgag ccgccaccgc aggtcgagga    180

cggtcggact cccgcggcgg gaggagcctg ttcccctgag ggtatttgaa gtataccata    240

caactgtttt gaaaatccag cgtggacaat ggctactcaa gctgatttga tggagttgga    300
```

-continued

```
catggccatg gaaccagaca gaaaagcggc tgttagtcac tggcagcaac agtcttacct    360
ggactctgga atccattctg gtgccactac cacagctcct tctctgagtg gtaaaggcaa    420
tcctgaggaa gaggatgtgg atacctccca agtcctgtat gagtgggaac agggattttc    480
tcagtccttc actcaagaac aagtagctga tattgatgga cagtatgcaa tgactcgagc    540
tcagagggta cgagctgcta tgttccctga gacattagat gagggcatgc agatcccatc    600
tacacagttt gatgctgctc atcccactaa tgtccagcgt ttggctgaac catcacagat    660
gctgaaacat gcagttgtaa acttgattaa ctatcaagat gatgcagaac ttgccacacg    720
tgcaatccct gaactgacaa aactgctaaa tgacgaggac caggtggtgg ttaataaggc    780
tgcagttatg gtccatcagc tttctaaaaa ggaagcttcc agacacgcta tcatgcgttc    840
tcctcagatg gtgtctgcta ttgtacgtac catgcagaat acaaatgatg tagaaacagc    900
tcgttgtacc gctgggacct tgcataacct ttcccatcat cgtgagggct tactggccat    960
ctttaagtct ggaggcattc ctgccctggt gaaaatgctt ggttcaccag tggattctgt   1020
gttgttttat gccattacaa ctctccacaa ccttttatta catcaagaag gagctaaaat   1080
ggcagtgcgt ttagctggtg ggctgcagaa aatggttgcc ttgctcaaca aaacaaatgt   1140
taaattcttg gctattacga cagactgcct tcaaatttta gcttatggca accaagaaag   1200
caagctcatc atactggcta gtggtggacc ccaagcttta gtaaatataa tgaggaccta   1260
tacttacgaa aaactactgt ggaccacaag cagagtgctg aaggtgctat ctgtctgctc   1320
tagtaataag ccggctattg tagaagctgg tggaatgcaa gctttaggac ttcacctgac   1380
agatccaagt caacgtcttg ttcagaactg tctttggact ctcaggaatc tttcagatgc   1440
tgcaactaaa caggaaggga tggaaggtct ccttgggact cttgttcagc ttctgggttc   1500
agatgatata aatgtggtca cctgtgcagc tggaattctt tctaacctca cttgcaataa   1560
ttataagaac aagatgatgg tctgccaagt gggtggtata gaggctcttg tgcgtactgt   1620
ccttcgggct ggtgacaggg aagacatcac tgagcctgcc atctgtgctc ttcgtcatct   1680
gaccagccga caccaagaag cagagatggc ccagaatgca gttcgccttc actatggact   1740
accagttgtg gttaagctct tacacccacc atcccactgg cctctgataa aggctactgt   1800
tggattgatt cgaaatcttg ccctttgtcc cgcaaatcat gcacctttgc gtgagcaggg   1860
tgccattcca cgactagttc agttgcttgt tcgtgcacat caggataccc agcgccgtac   1920
gtccatgggt gggacacagc agcaatttgt ggagggggtc cgcatggaag aaatagttga   1980
aggttgtacc ggagcccttc acatcctagc tcgggatgtt cacaaccgaa ttgttatcag   2040
aggactaaat accattccat tgtttgtgca gctgctttat tctcccattg aaaacatcca   2100
aagagtagct gcaggggtcc tctgtgaact tgctcaggac aaggaagctg cagaagctat   2160
tgaagctgag ggagccacag ctcctctgac agagttactt cactctagga atgaaggtgt   2220
ggcgacatat gcagctgctg ttttgttccg aatgtctgag gacaagccac aagattacaa   2280
gaaacggctt tcagttgagc tgaccagctc tctcttcaga acagagccaa tggcttggaa   2340
tgagactgct gatcttggac ttgatattgg tgcccaggga gaaccccttg gatatcgcca   2400
ggatgatcct agctatcgtt cttttcactc tggtggatat ggccaggatg ccttgggtat   2460
ggaccccatg atggaacatg agatgggtgg ccaccaccct ggtgctgact atccagttga   2520
tgggctgcca gatctggggc atgcccagga cctcatggat gggctgcctc caggtgacag   2580
caatcagctg gcctggtttg atactgacct gtaaatcatc ctttaggagt aacaatacaa   2640
atggattttg ggagtgactc aagaagtgaa gaatgcacaa gaatggatca caagatggaa   2700
```

```
tttatcaaac cctagccttg cttgttaaat tttttttttt ttttttttaa gaatatctgt   2760

aatggtactg actttgcttg ctttgaagta gctctttttt tttttttttt tttttttttg   2820

cagtaactgt tttttaagtc tctcgtagtg ttaagttata gtgaatactg ctacagcaat   2880

ttctaatttt taagaattga gtaatggtgt agaacactaa ttcataatca ctctaattaa   2940

ttgtaatctg aataaagtgt aacaattgtg tagccttttt gtataaaata gacaaataga   3000

aaatggtcca attagtttcc tttttaatat gcttaaaata agcaggtgga tctatttcat   3060

gtttttgatc aaaaactatt tgggatatgt atgggtaggg taaatcagta agaggtgtta   3120

tttggaacct tgttttggac agtttaccag ttgcctttta tcccaaagtt gttgtaacct   3180

gctgtgatac gatgcttcaa gagaaaatgc ggttataaaa aatggttcag aattaaactt   3240

ttaattcatt cgattg                                                   3256
```

<210> SEQ ID NO 11
<211> LENGTH: 387
<212> TYPE: PRT
<213> ORGANISM: Homo sapiens
<220> FEATURE:
<223> OTHER INFORMATION: milk fat globule-EGF factor 8 protein (MFGE8, MFG-E8), lactadherin isoform a preprotein, sperm associated antigen 10 (SPAG10), O-acetyl disialoganglioside synthase (OAcGD3S), medin, sperm surface protein hP47, breast epithelial antigen BA46

<400> SEQUENCE: 11

```
Met Pro Arg Pro Arg Leu Leu Ala Ala Leu Cys Gly Ala Leu Leu Cys
1               5                   10                  15

Ala Pro Ser Leu Leu Val Ala Leu Asp Ile Cys Ser Lys Asn Pro Cys
            20                  25                  30

His Asn Gly Gly Leu Cys Glu Glu Ile Ser Gln Glu Val Arg Gly Asp
        35                  40                  45

Val Phe Pro Ser Tyr Thr Cys Thr Cys Leu Lys Gly Tyr Ala Gly Asn
    50                  55                  60

His Cys Glu Thr Lys Cys Val Glu Pro Leu Gly Leu Glu Asn Gly Asn
65                  70                  75                  80

Ile Ala Asn Ser Gln Ile Ala Ala Ser Ser Val Arg Val Thr Phe Leu
                85                  90                  95

Gly Leu Gln His Trp Val Pro Glu Leu Ala Arg Leu Asn Arg Ala Gly
            100                 105                 110

Met Val Asn Ala Trp Thr Pro Ser Ser Asn Asp Asp Asn Pro Trp Ile
        115                 120                 125

Gln Val Asn Leu Leu Arg Arg Met Trp Val Thr Gly Val Val Thr Gln
    130                 135                 140

Gly Ala Ser Arg Leu Ala Ser His Glu Tyr Leu Lys Ala Phe Lys Val
145                 150                 155                 160

Ala Tyr Ser Leu Asn Gly His Glu Phe Asp Phe Ile His Asp Val Asn
                165                 170                 175

Lys Lys His Lys Glu Phe Val Gly Asn Trp Asn Lys Asn Ala Val His
            180                 185                 190

Val Asn Leu Phe Glu Thr Pro Val Glu Ala Gln Tyr Val Arg Leu Tyr
        195                 200                 205

Pro Thr Ser Cys His Thr Ala Cys Thr Leu Arg Phe Glu Leu Leu Gly
    210                 215                 220

Cys Glu Leu Asn Gly Cys Ala Asn Pro Leu Gly Leu Lys Asn Asn Ser
225                 230                 235                 240
```

```
Ile Pro Asp Lys Gln Ile Thr Ala Ser Ser Ser Tyr Lys Thr Trp Gly
                245                 250                 255

Leu His Leu Phe Ser Trp Asn Pro Ser Tyr Ala Arg Leu Asp Lys Gln
            260                 265                 270

Gly Asn Phe Asn Ala Trp Val Ala Gly Ser Tyr Gly Asn Asp Gln Trp
        275                 280                 285

Leu Gln Val Asp Leu Gly Ser Ser Lys Glu Val Thr Gly Ile Ile Thr
    290                 295                 300

Gln Gly Ala Arg Asn Phe Gly Ser Val Gln Phe Val Ala Ser Tyr Lys
305                 310                 315                 320

Val Ala Tyr Ser Asn Asp Ser Ala Asn Trp Thr Glu Tyr Gln Asp Pro
                325                 330                 335

Arg Thr Gly Ser Ser Lys Ile Phe Pro Gly Asn Trp Asp Asn His Ser
            340                 345                 350

His Lys Lys Asn Leu Phe Glu Thr Pro Ile Leu Ala Arg Tyr Val Arg
        355                 360                 365

Ile Leu Pro Val Ala Trp His Asn Arg Ile Ala Leu Arg Leu Glu Leu
    370                 375                 380

Leu Gly Cys
385
```

<210> SEQ ID NO 12
<211> LENGTH: 2005
<212> TYPE: DNA
<213> ORGANISM: Homo sapiens
<220> FEATURE:
<223> OTHER INFORMATION: milk fat globule-EGF factor 8 protein (MFGE8, MFG-E8), lactadherin transcript variant 1, sperm associated antigen 10 (SPAG10), O-acetyl disialoganglioside synthase (OAcGD3S), medin, sperm surface protein hP47, breast epithelial antigen BA46

<400> SEQUENCE: 12

```
agtgggaggt gctgagccgc ctgatttatt ccggtcccag aggagaaggc gccagaaccc     60

cgcggggtct gagcagccca gcgtgcccat tccagcgccc gcgtccccgc agcatgccgc    120

gcccccgcct gctggccgcg ctgtgcggcg cgctgctctg cgcccccagc ctcctcgtcg    180

ccctggatat ctgttccaaa aacccctgcc acaacggtgg tttatgcgag gagatttccc    240

aagaagtgcg aggagatgtc ttcccctcgt acacctgcac gtgccttaag ggctacgcgg    300

gcaaccactg tgagacgaaa tgtgtcgagc cactgggcct ggagaatggg aacattgcca    360

actcacagat cgccgcctcg tctgtgcgtg tgaccttctt gggtttgcag cattgggtcc    420

cggagctggc ccgcctgaac cgcgcaggca tggtcaatgc ctggacaccc agcagcaatg    480

acgataaccc ctggatccag gtgaacctgc tgcggaggat gtgggtaaca ggtgtggtga    540

cgcagggtgc cagccgcttg gccagtcatg agtacctgaa ggccttcaag gtggcctaca    600

gccttaatgg acacgaattc gatttcatcc atgatgttaa taaaaaacac aaggagtttg    660

tgggtaactg gaacaaaaac gcggtgcatg tcaacctgtt tgagacccct gtggaggctc    720

agtacgtgag attgtacccc acgagctgcc acacggcctg cactctgcgc tttgagctac    780

tgggctgtga gctgaacgga tgcgccaatc ccctgggcct gaagaataac agcatccctg    840

acaagcagat cacggcctcc agcagctaca agacctgggg cttgcatctc ttcagctgga    900

acccctccta tgcacggctg gacaagcagg gcaacttcaa cgcctgggtt gcggggagct    960

acggtaacga tcagtggctg caggtggacc tgggctcctc gaaggaggtg acaggcatca   1020
```

```
tcacccaggg ggcccgtaac tttggctctg tccagtttgt ggcatcctac aaggttgcct   1080

acagtaatga cagtgcgaac tggactgagt accaggaccc caggactggc agcagtaaga   1140

tcttccctgg caactgggac aaccactccc acaagaagaa cttgtttgag acgcccatcc   1200

tggctcgcta tgtgcgcatc ctgcctgtag cctggcacaa ccgcatcgcc ctgcgcctgg   1260

agctgctggg ctgttagtgg ccacctgcca cccccaggtc ttcctgcttt ccatgggccc   1320

gctgcctctt ggcttctcag cccctttaaa tcaccatagg gctggggact ggggaagggg   1380

agggtgttca gaggcagcac caccacacag tcacccctcc ctccctcttt cccaccctcc   1440

acctctcacg ggccctgccc cagcccctaa gccccgtccc ctaaccccca gtcctcactg   1500

tcctgttttc ttaggcactg agggatctga gtaggtctgg gatggacagg aaagggcaaa   1560

gtagggcgtg tggtttccct gcccctgtcc ggaccgccga tcccaggtgc gtgtgtctct   1620

gtctctccta gcccctctct cacacatcac attcccatgg tggcctcaag aaaggcccgg   1680

aagcgccagg ctggagataa cagcctcttg cccgtcggcc ctgcgtcggc cctggggtac   1740

catgtggcca caactgctgt ggccccctgt ccccaagaca cttccccttg tctccctggt   1800

tgcctctctt gccccttgtc ctgaagccca gcgacacaga agggggtggg gcgggtctat   1860

ggggagaaag ggagcgaggt cagaggaggg catgggttgg cagggtgggc gtttggggcc   1920

ctctatgctg gcttttcacc ccagaggaca caggcagctt ccaaaatata tttatcttct   1980

tcacgggaaa aaaaaaaaaa aaaaa                                          2005
```

```
<210> SEQ ID NO 13
<211> LENGTH: 354
<212> TYPE: PRT
<213> ORGANISM: Homo sapiens
<220> FEATURE:
<223> OTHER INFORMATION: macrophage antigen CD68, microsialin isoform A
      precursor, lysosomal/endosomal-associated membrane glycoprotein 4
      (LAMP4), scavenger receptor class D, member 1 (SCARD1), GP110

<400> SEQUENCE: 13

Met Arg Leu Ala Val Leu Phe Ser Gly Ala Leu Leu Gly Leu Leu Ala
1               5                   10                  15

Ala Gln Gly Thr Gly Asn Asp Cys Pro His Lys Lys Ser Ala Thr Leu
            20                  25                  30

Leu Pro Ser Phe Thr Val Thr Pro Thr Val Thr Glu Ser Thr Gly Thr
        35                  40                  45

Thr Ser His Arg Thr Thr Lys Ser His Lys Thr Thr Thr His Arg Thr
    50                  55                  60

Thr Thr Thr Gly Thr Thr Ser His Gly Pro Thr Thr Ala Thr His Asn
65                  70                  75                  80

Pro Thr Thr Thr Ser His Gly Asn Val Thr Val His Pro Thr Ser Asn
                85                  90                  95

Ser Thr Ala Thr Ser Gln Gly Pro Ser Thr Ala Thr His Ser Pro Ala
            100                 105                 110

Thr Thr Ser His Gly Asn Ala Thr Val His Pro Thr Ser Asn Ser Thr
        115                 120                 125

Ala Thr Ser Pro Gly Phe Thr Ser Ser Ala His Pro Glu Pro Pro Pro
    130                 135                 140

Pro Ser Pro Ser Pro Ser Pro Thr Ser Lys Glu Thr Ile Gly Asp Tyr
145                 150                 155                 160

Thr Trp Thr Asn Gly Ser Gln Pro Cys Val His Leu Gln Ala Gln Ile
                165                 170                 175
```

```
Gln Ile Arg Val Met Tyr Thr Thr Gln Gly Gly Gly Glu Ala Trp Gly
            180                 185                 190

Ile Ser Val Leu Asn Pro Asn Lys Thr Lys Val Gln Gly Ser Cys Glu
        195                 200                 205

Gly Ala His Pro His Leu Leu Leu Ser Phe Pro Tyr Gly His Leu Ser
    210                 215                 220

Phe Gly Phe Met Gln Asp Leu Gln Gln Lys Val Val Tyr Leu Ser Tyr
225                 230                 235                 240

Met Ala Val Glu Tyr Asn Val Ser Phe Pro His Ala Ala Gln Trp Thr
                245                 250                 255

Phe Ser Ala Gln Asn Ala Ser Leu Arg Asp Leu Gln Ala Pro Leu Gly
            260                 265                 270

Gln Ser Phe Ser Cys Ser Asn Ser Ser Ile Ile Leu Ser Pro Ala Val
        275                 280                 285

His Leu Asp Leu Leu Ser Leu Arg Leu Gln Ala Ala Gln Leu Pro His
    290                 295                 300

Thr Gly Val Phe Gly Gln Ser Phe Ser Cys Pro Ser Asp Arg Ser Ile
305                 310                 315                 320

Leu Leu Pro Leu Ile Ile Gly Leu Ile Leu Leu Gly Leu Leu Ala Leu
                325                 330                 335

Val Leu Ile Ala Phe Cys Ile Ile Arg Arg Arg Pro Ser Ala Tyr Gln
            340                 345                 350

Ala Leu


<210> SEQ ID NO 14
<211> LENGTH: 1872
<212> TYPE: DNA
<213> ORGANISM: Homo sapiens
<220> FEATURE:
<223> OTHER INFORMATION: macrophage antigen CD68, microsialin transcript
      variant 1, lysosomal/endosomal-associated membrane glycoprotein 4
      (LAMP4), scavenger receptor class D, member 1 (SCARD1), GP110

<400> SEQUENCE: 14

ttaattacaa aaactaatga ctaagagaga ggtggctaga gctgaggccc ctgagtcagg     60

ctgtgggtgg gatcatctcc agtacaggaa gtgagacttt catttcctcc tttccaagag    120

agggctgagg gagcagggtt gagcaactgg tgcagacagc ctagctggac tttgggtgag    180

gcggttcagc catgaggctg gctgtgcttt tctcgggggc cctgctgggg ctactggcag    240

cccaggggac agggaatgac tgtcctcaca aaaaatcagc tactttgctg ccatccttca    300

cggtgacacc cacggttaca gagagcactg gaacaaccag ccacaggact accaagagcc    360

acaaaaccac cactcacagg acaaccacca caggcaccac cagccacgga cccacgactg    420

ccactcacaa ccccaccacc accagccatg gaaacgtcac agttcatcca acaagcaata    480

gcactgccac cagccaggga ccctcaactg ccactcacag tcctgccacc actagtcatg    540

gaaatgccac ggttcatcca acaagcaaca gcactgccac cagcccagga ttcaccagtt    600

ctgcccaccc agaaccacct ccaccctctc cgagtcctag cccaacctcc aaggagacca    660

ttggagacta cacgtggacc aatggttccc agccctgtgt ccacctccaa gcccagattc    720

agattcgagt catgtacaca acccagggtg gaggagaggc ctggggcatc tctgtactga    780

accccaacaa aaccaaggtc cagggaagct gtgagggtgc ccatccccac ctgcttctct    840

cattccccta tggacacctc agctttggat tcatgcagga cctccagcag aaggttgtct    900

acctgagcta catggcggtg gagtacaatg tgtccttccc ccacgcagca cagtggacat    960
```

-continued

```
tctcggctca gaatgcatcc cttcgagatc tccaagcacc cctggggcag agcttcagtt   1020

gcagcaactc gagcatcatt ctttcaccag ctgtccacct cgacctgctc tccctgaggc   1080

tccaggctgc tcagctgccc cacacagggg tctttgggca aagtttctcc tgccccagtg   1140

accggtccat cttgctgcct ctcatcatcg gcctgatcct tcttggcctc ctcgccctgg   1200

tgcttattgc tttctgcatc atccggagac gcccatccgc ctaccaggcc ctctgagcat   1260

ttgcttcaaa ccccagggca ctgagggggt tggggtgtgg tggggggggta cccttatttc   1320

ctcgacacgc aactggctca aagacaatgt tattttcctt ccctttcttg aagaacaaaa   1380

agaaagccgg gcatgacggc tcatgcctgt aatcccagca ctttgggagg ctgaggcagg   1440

tggatcactg gaggtcagga gtttgagacc agcctggcca acatggtgaa accctgtctc   1500

tactaaaaat acaattagcc aggtgtggcg gcgtaatccc agctggcctg taatcccagc   1560

tacttgggag gctgaggcag aactgcttga acccaggagg tggaggttgc agtgagccgt   1620

catcgcgcca ctaagccaag atcgcgccac tgcactccag cctgggcgac agagccagac   1680

tgtctcaaat aaataaatat gagataatgc agtcgggaga agggagggag agaattttat   1740

taaatgtgac gaactgcccc cccccccccc ccagcaggag agcagcaaaa tttatgcaaa   1800

tctttgacgg ggtttccctt gtcctgccag gattaaaagc catgagtttc ttgtcaaaaa   1860

aaaaaaaaaa aa                                                       1872
```